(12) United States Patent
Zhang

(10) Patent No.: US 11,230,524 B2
(45) Date of Patent: Jan. 25, 2022

(54) MYOCYTE ENHANCER FACTOR 2 (MEF2) MODULATORS

(71) Applicant: STANDARD LLC, Los Angeles, CA (US)

(72) Inventor: Junhu Zhang, San Diego, CA (US)

(73) Assignee: STANDARD LLC, Los Angeles, CA (US)

( * ) Notice: Subject to any disclaimer, the term of this patent is extended or adjusted under 35 U.S.C. 154(b) by 0 days.

(21) Appl. No.: 15/999,268

(22) Filed: Aug. 17, 2018

(65) Prior Publication Data

US 2019/0241504 A1    Aug. 8, 2019

Related U.S. Application Data

(60) Provisional application No. 62/547,028, filed on Aug. 17, 2017.

(51) Int. Cl.

| | |
|---|---|
| *C07C 237/20* | (2006.01) |
| *C07D 213/30* | (2006.01) |
| *C07D 417/04* | (2006.01) |
| *C07D 263/48* | (2006.01) |
| *C07C 233/44* | (2006.01) |
| *C07C 259/06* | (2006.01) |
| *C07C 323/36* | (2006.01) |
| *C07D 215/38* | (2006.01) |
| *C07D 277/82* | (2006.01) |
| *C07D 305/08* | (2006.01) |
| *C07D 285/135* | (2006.01) |
| *C07D 271/113* | (2006.01) |
| *C07D 213/56* | (2006.01) |
| *C07D 209/14* | (2006.01) |
| *C07D 295/135* | (2006.01) |
| *C07D 213/74* | (2006.01) |
| *C07D 401/04* | (2006.01) |

(52) U.S. Cl.
CPC .......... *C07C 237/20* (2013.01); *C07C 233/44* (2013.01); *C07C 259/06* (2013.01); *C07C 323/36* (2013.01); *C07D 209/14* (2013.01); *C07D 213/30* (2013.01); *C07D 213/56* (2013.01); *C07D 213/74* (2013.01); *C07D 215/38* (2013.01); *C07D 263/48* (2013.01); *C07D 271/113* (2013.01); *C07D 277/82* (2013.01); *C07D 285/135* (2013.01); *C07D 295/135* (2013.01); *C07D 305/08* (2013.01); *C07D 401/04* (2013.01); *C07D 417/04* (2013.01); *C07C 2601/02* (2017.05); *C07C 2601/04* (2017.05); *C07C 2601/08* (2017.05)

(58) Field of Classification Search
None
See application file for complete search history.

(56) References Cited

U.S. PATENT DOCUMENTS

2016/0264518 A1* 9/2016 Bair .................... C07D 409/12

FOREIGN PATENT DOCUMENTS

| WO | WO 2003024448 | * | 3/2003 | |
|---|---|---|---|---|
| WO | WO-2010028193 A1 | * | 3/2010 | ............. A61K 31/00 |

OTHER PUBLICATIONS

Mai et al, Medicinal Chemistry (2005), 1(3), 245-254 (asbtract).*
Mahipal et al. Medicinal Chemistry (2010), 6(5), 277-285.*
Han, A., et al., "Sequence-Specific Recruitment of Transcriptional Co-Repressor Cabin 1 by Myocyte Enhancer Factor-2," Nature 422:730-734 (2003).
Han, A., et al., "Mechanism of Recruitment of Class II Histone Deacetylases by Myocyte Enhancer Factor-2," J. Mol. Biol. 345:91-102 (2005).
Jayathilaka, N., et al., "Inhibition of the Function of Class IIa HDACs by Blocking Their Interaction with MEF2," Nucleic Acids Res. 40(12):5378-5388 (2012).
Potthoff, M. J., et al., "MEF2: A Central Regulator of Diverse Developmental Programs," Development 134:4131-4140 (2007).
Wu, L., et al., "Multidrug-Resistant Phenotype of Disease-Oriented Panels of Human Tumor Cell Lines Used for Anticancer Drug Screening," Cancer Res. 52:3029-3034 (1992).

* cited by examiner

*Primary Examiner* — Ana Z Muresan

(74) *Attorney, Agent, or Firm* — Perkins Coie LLP

(57) ABSTRACT

The present disclosure provides novel compounds capable of functioning as Myocyte Enhancer Factor 2 (MEF2) modulators, as well as compositions, pharmaceutical formulations, methods of synthesis and kits.

6 Claims, No Drawings

MYOCYTE ENHANCER FACTOR 2 (MEF2) MODULATORS

PRIORITY CLAIM

This application claims priority to U.S. Provisional Application No. 62/547,028, filed Aug. 17, 2017, which is incorporated herein by reference.

BACKGROUND

Alterations of epigenetic regulation are a characteristic of many diseases. The myocyte enhancer factor 2 (MEF2) transcription factor plays a central role in the transmission of extracellular signals to the genome and in the activation of the genetic programs that control cell differentiation, proliferation, morphogenesis, survival, and apoptosis of a wide range of cell types (Potthoff et al., 2007). The spectrum of genes activated by MEF2 in different cell types depends on extracellular signaling and on co-factor interactions that modulate MEF2 activity. To drive the expression of MEF2 target genes, MEF2 relies on the recruitment of and cooperation with a number of transcription factors including, but not limited to, calcineurin binding protein 1, E1A binding protein P300, CREB binding protein, extracellular signal-regulated kinase 5, myoblast differentiation protein, Smad protein, nuclear factor of activated T cell, myocardin, class IIa histone deacetylases (HDAC IIa) and positive transcription elongation factor b.

SUMMARY

One aspect of the present disclosure relates to compounds comprising a structure selected from the group consisting of Structure I, Structure II, Structure III, Structure IV, and Table 5, including pharmaceutically acceptable solvates, pharmaceutically acceptable prodrugs, pharmaceutically acceptable salts and pharmaceutically acceptable stereoisomers thereof. Other aspects relate to compositions, pharmaceutical formulations, methods of synthesis, and kits comprising the compounds disclosed herein.

Another aspect of the present disclosure relates to a method of treating a subject for a condition regulatable by MEF2 and/or MEF2 cofactors by administering to the subject one or more of the compounds, compositions, or pharmaceutical formulations provided herein.

Another aspect of the present disclosure relates to the use of one or more of the compounds, compositions, or pharmaceutical formulations provided herein in the manufacture of a medicament for the treatment of a condition regulatable by MEF2 and/or MEF2 cofactors.

Another aspect of the present disclosure relates to kits comprising one or more of the compounds, compositions, or pharmaceutical formulations provided herein.

Another aspect of the present disclosure relates to the method of synthesizing the disclosed compounds.

DETAILED DESCRIPTION

Previously, Myocyte Enhancer Factor 2 (MEF2) was considered an "undruggable" target. Modulation of MEF2 activity could likely reverse the progression of deleterious diseases or prevent the onset of diseases that are affected by MEF2 transcription. Hence, there is a significant need for MEF2 modulators.

I. Compounds

One aspect of the present disclosure relates to compounds comprising a structure selected from the group consisting of Structure I, Structure II, Structure III, Structure IV, and Table 5, including pharmaceutically acceptable solvates, pharmaceutically acceptable prodrugs, pharmaceutically acceptable salts and pharmaceutically acceptable stereoisomers thereof.

In certain embodiments, the compounds provided herein are transcription factor modulators.

In certain embodiments, the compounds provided herein are Myocyte Enhancer Factor 2 (MEF2) modulators.

Structure I

In certain embodiments, the compounds provided herein comprise a structure of Structure I:

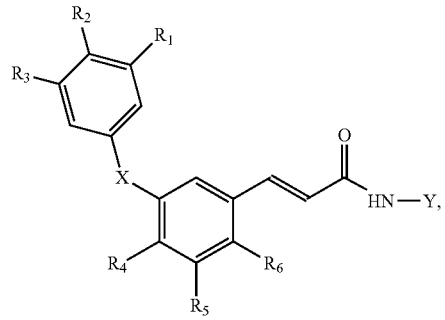

Structure I including pharmaceutically acceptable solvates, pharmaceutically acceptable prodrugs, pharmaceutically acceptable salts and pharmaceutically acceptable stereoisomers thereof, wherein:

Y is independently selected from the group consisting of 2-aminophenyl and hydroxyl;

X is independently selected from the group consisting of —NH—, —NH—(O=C)—(C=OPh)H—, —NHC(=O)—, —C(=O)NH—, —(CH$_2$)$_n$—NH—, —(CH$_2$)$_n$—NH—(CH$_2$)$_n$—, and —NH—(CH$_2$)$_n$—, where n is 1, 2, or 3;

R$_1$-R$_3$ are each independently selected from the group consisting of hydrogen, cyclopropyloxy, halogen, ethoxy, methoxy, methyl-mercaptan, ethoxy, ethyl, cyano, isopropyloxy, cyclobutyloxy, cyclopentyloxy, 3-oxetanyloxy, morpholinyl, 4-morpholinyl, dimethylamino, butyl, pyrrolidinyl, ethylmethylamino, piperidinyl, piperazinyl, diethylamino, dimethylaminomethyl, 3-oxetanyl, 2,2-difluoroethoxy, 1,1-difluoroethyl, methylsulfide, trifluoromethylsulfide, 2,2,2-trifluoroethoxy, and trifluoroethoxy, wherein at least one or two of R$_1$-R$_3$ are not hydrogen; and R$_4$-R$_6$ are each independently selected from the group consisting of hydrogen and halogen.

In certain embodiments, R$_4$ and R$_5$ are hydrogen and R$_6$ is a halogen.

In certain embodiments, R$_4$ and R$_6$ are hydrogen and R$_5$ is a halogen.

In certain embodiments, R$_5$ and R$_6$ are hydrogen and R$_4$ is a halogen.

In certain embodiments, R$_4$-R$_6$ are hydrogen.

In certain embodiments, at least two of R$_1$-R$_3$ are hydrogen.

In certain embodiments, X is independently selected from a group consisting of —(CH$_2$)$_2$—NH—(CH$_2$)$_1$—, —(CH$_2$)—NH—(CH$_2$)—, —NH—(CH$_2$)—, —(CH$_2$)—NH—, and —(CH$_2$)$_2$—NH—, where n is 1, 2, or 3.

In certain embodiments, X is independently selected from a group consisting of —(CH$_2$)$_2$—NH—(CH$_2$)$_1$—, —(CH$_2$)—NH—(CH$_2$)—, —NH—(CH$_2$)—, —(CH$_2$)—NH—, and —(CH$_2$)$_2$—NH—, where n is 1, 2, or 3; R$_4$-R$_6$ are hydrogen; and at least two of R$_1$-R$_3$ are hydrogen.

In certain embodiments, X is independently selected from a group consisting of —(CH$_2$)$_2$—NH—(CH$_2$)$_1$—, —(CH$_2$)—NH—(CH$_2$)—, —NH—(CH$_2$)—, —(CH$_2$)—NH—, and —(CH$_2$)$_2$—NH—, where n is 1, 2, or 3; wherein at least two of R$_1$-R$_3$ are hydrogen, and wherein further at least two of R$_4$-R$_6$ are hydrogen.

In certain embodiments, X is independently selected from a group consisting of —NH—, —NH—(O=C)—(C=OPh)H—, —NHC(=O)—, and —C(=O)NH—.

In certain embodiments, X is independently selected from a group consisting of —NH—, —NH—(O=C)—(C=OPh)H—, —NHC(=O)—, and —C(=O)NH—; R$_4$-R$_6$ are hydrogen; and at least two of R$_1$-R$_3$ are hydrogen.

In certain embodiments, X is independently selected from a group consisting of —NH—, —NH—(O=C)—(C=OPh)H—, —NHC(=O)—, and —C(=O)NH—; wherein at least two of R$_1$-R$_3$ are hydrogen, and wherein further at least two of R$_4$-R$_6$ are hydrogen.

In certain embodiments, the compounds are selected from the group consisting of ST Nos. 1~46 listed in Table 1 below (ST Nos. 30, 35, and 36 are excluded from Table 1), including pharmaceutically acceptable solvates, pharmaceutically acceptable prodrugs, pharmaceutically acceptable salts and pharmaceutically acceptable stereoisomers thereof.

TABLE 1

Compounds ST Nos. 1~46 (excluding 30, 35, and 36)

| ST Nos. | Compounds |
|---|---|
| ST1 | [chemical structure] |
| ST2 | [chemical structure] |
| ST3 | [chemical structure] |
| ST4 | [chemical structure] |
| ST5 | [chemical structure] |
| ST6 | [chemical structure] |

TABLE 1-continued

Compounds ST Nos. 1~46 (excluding 30, 35, and 36)

| ST Nos. | Compounds |
|---|---|
| ST7 | 3-cyclopropoxyphenyl-NH-CH2-(3-substituted phenyl)-CH=CH-C(=O)-NH-(2-aminophenyl) |
| ST8 | 3-morpholinophenyl-NH-CH2-(3-substituted phenyl)-CH=CH-C(=O)-NH-(2-aminophenyl) |
| ST9 | 3-(diethylamino)phenyl-NH-CH2-(3-substituted phenyl)-CH=CH-C(=O)-NH-(2-aminophenyl) |
| ST10 | 3-(pyrrolidin-1-yl)phenyl-NH-CH2-(3-substituted phenyl)-CH=CH-C(=O)-NH-(2-aminophenyl) |
| ST11 | phenyl-NH-CH2-(3-substituted-4-fluorophenyl)-CH=CH-C(=O)-NH-(2-aminophenyl) |
| ST12 | 3-methoxyphenyl-NH-CH2-(3-substituted-4-fluorophenyl)-CH=CH-C(=O)-NH-(2-aminophenyl) |
| ST13 | 3-cyclopropoxybenzyl-NH-CH2-(3-substituted phenyl)-CH=CH-C(=O)-NH-(2-aminophenyl) |
| ST14 | 3-cyclobutoxybenzyl-NH-CH2-(3-substituted phenyl)-CH=CH-C(=O)-NH-(2-aminophenyl) |

TABLE 1-continued

Compounds ST Nos. 1~46 (excluding 30, 35, and 36)

| ST Nos. | Compounds |
|---|---|
| ST15 | 3-((phenylamino)methyl)cinnamic acid hydroxyamide |
| ST16 | 3-(((3-cyclopropoxyphenyl)amino)methyl)cinnamic acid hydroxyamide |
| ST17 | 3-(((4-fluorophenyl)amino)methyl)cinnamic acid hydroxyamide |
| ST18 | 3-(((3-fluorophenyl)amino)methyl)cinnamic acid hydroxyamide |
| ST19 | 3-(((3-methoxyphenyl)amino)methyl)cinnamic acid hydroxyamide |
| ST20 | 3-(((3-(methylthio)phenyl)amino)methyl)cinnamic acid hydroxyamide |
| ST21 | 3-(((3-ethoxyphenyl)amino)methyl)cinnamic acid hydroxyamide |
| ST22 | 3-(((3-ethylphenyl)amino)methyl)cinnamic acid hydroxyamide |
| ST23 | 3-(((3-cyanophenyl)amino)methyl)cinnamic acid hydroxyamide |

TABLE 1-continued

Compounds ST Nos. 1~46 (excluding 30, 35, and 36)

| ST Nos. | Compounds |
|---|---|
| ST24 | 3,4-difluorophenyl-NH-CH2-(3-phenyl)-CH=CH-C(=O)-NH-OH |
| ST25 | 2,4-difluorophenyl-NH-CH2-(3-phenyl)-CH=CH-C(=O)-NH-OH |
| ST26 | 4-chlorophenyl-NH-CH2-(3-phenyl)-CH=CH-C(=O)-NH-OH |
| ST27 | 3-isopropoxyphenyl-NH-CH2-(3-phenyl)-CH=CH-C(=O)-NH-OH |
| ST28 | 3-cyclobutoxyphenyl-NH-CH2-(3-phenyl)-CH=CH-C(=O)-NH-OH |
| ST29 | 3-cyclopentyloxyphenyl-NH-CH2-(3-phenyl)-CH=CH-C(=O)-NH-OH |
| ST31 | 3-(oxetan-3-yloxy)phenyl-NH-CH2-(3-phenyl)-CH=CH-C(=O)-NH-OH |
| ST32 | 3-morpholinophenyl-NH-CH2-(3-phenyl)-CH=CH-C(=O)-NH-OH |

TABLE 1-continued
Compounds ST Nos. 1~46 (excluding 30, 35, and 36)
| ST Nos. | Compounds |
|---|---|
| ST33 | 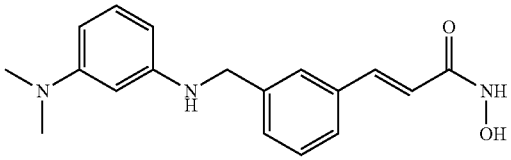 [SMILES: CN(C)c1cccc(NCc2cccc(/C=C/C(=O)NO)c2)c1] |
| ST34 | 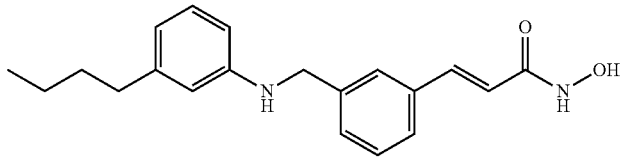 [SMILES: CCCCc1cccc(NCc2cccc(/C=C/C(=O)NO)c2)c1] |
| ST37 | 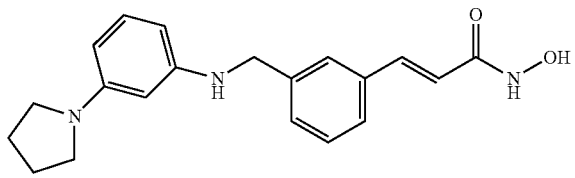 [SMILES: O=C(/C=C/c1cccc(CNc2cccc(N3CCCC3)c2)c1)NO] |
| ST38 | 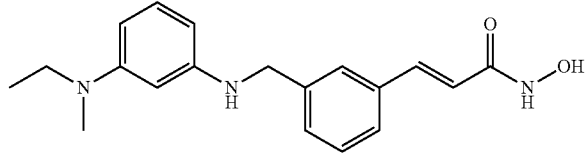 [SMILES: CCN(C)c1cccc(NCc2cccc(/C=C/C(=O)NO)c2)c1] |
| ST39 | 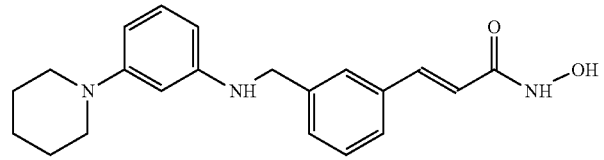 [SMILES: O=C(/C=C/c1cccc(CNc2cccc(N3CCCCC3)c2)c1)NO] |
| ST40 | 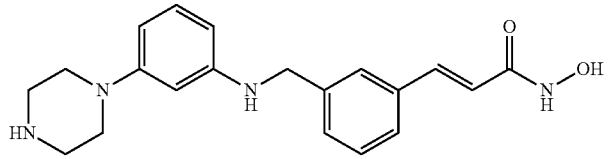 [SMILES: O=C(/C=C/c1cccc(CNc2cccc(N3CCNCC3)c2)c1)NO] |
| ST41 | 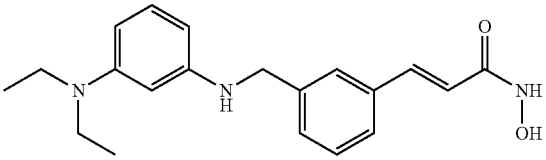 [SMILES: CCN(CC)c1cccc(NCc2cccc(/C=C/C(=O)NO)c2)c1] |
| ST42 | 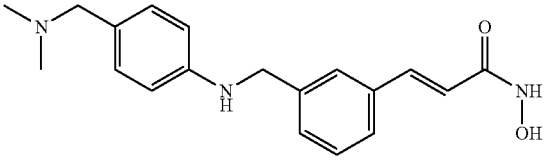 [SMILES: CN(C)Cc1ccc(NCc2cccc(/C=C/C(=O)NO)c2)cc1] |
| ST43 | 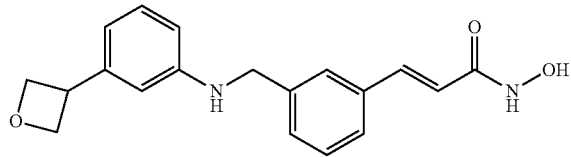 [SMILES: O=C(/C=C/c1cccc(CNc2cccc(C3COC3)c2)c1)NO] |

TABLE 1-continued

Compounds ST Nos. 1~46 (excluding 30, 35, and 36)

| ST Nos. | Compounds |
|---|---|
| ST44 | 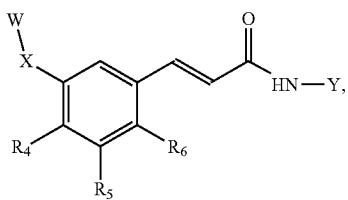 |
| ST45 | |
| ST46 | |

Structure II

In certain embodiments, the compounds provided herein comprise a structure of Structure II:

Structure II including pharmaceutically acceptable solvates, pharmaceutically acceptable prodrugs, pharmaceutically acceptable salts and pharmaceutically acceptable stereoisomers thereof, wherein:

Y, $R_4$-$R_6$, and X are defined the same as above as for Structure I; and

W is independently selected from the group consisting of cyclopropyl, benzene, 3-methoxy-pyridinyl, 4-(pyridin-4-yl)thiazolyl, 2-(2-Methyl-1H-indol-3-yl), pyridinyl, 3-ethoxy-pyridine, 5-methyl-1,3,4-thiadiazolyl, 5-(trifluoromethyl)-1,3,4-thiadiazolyl, 4-(trifluoromethyl)thiazolyl, 5-Methyl-1,3,4-oxadiazolyl, 4-methyloxazolyl, 4-methylthiazolyl, 4-(trifluoromethyl)oxazolyl, 4-(pyridin-3-yl)pyrimidinyl, benzo[d]thiazolyl, 4-(4-methoxyphenyl)thiazolyl, 4-(4-fluorophenyl)thiazolyl, 4-(pyridin-4-yl)thiazolyl, 2-Naphthalenyl, 6-Quinolinyl, 8-Quinolinyl, (E)-3-(pyridin-3-yl)acryloyl, pyridin-3-ylmethoxy, 3-Pyridinyl, and 5-methylthiazolyl.

In certain embodiments, $R_4$ and $R_5$ are hydrogen and $R_6$ is a halogen.

In certain embodiments, $R_4$ and $R_6$ are hydrogen and $R_5$ is a halogen.

In certain embodiments, $R_5$ and $R_6$ are hydrogen and $R_4$ is a halogen.

In certain embodiments, $R_4$-$R_6$ are hydrogen.

In certain embodiments, X is independently selected from a group consisting of —(CH$_2$)$_2$—NH—(CH$_2$)$_1$—, —(CH$_2$)—NH—(CH$_2$)—, —NH—(CH$_2$)—, —(CH$_2$)—NH—, and —(CH$_2$)$_2$—NH—, where n is 1, 2, or 3.

In certain embodiments, X is independently selected from a group consisting of —(CH$_2$)$_2$—NH—(CH$_2$)$_1$—, —(CH$_2$)—NH—(CH$_2$)—, —NH—(CH$_2$)—, —(CH$_2$)—NH—, and —(CH$_2$)$_2$—NH—, where n is 1, 2, or 3; and $R_4$-$R_6$ are hydrogen;

In certain embodiments, X is independently selected from a group consisting of —(CH$_2$)$_2$—NH—(CH$_2$)$_1$—, —(CH$_2$)—NH—(CH$_2$)—, —NH—(CH$_2$)—, —(CH$_2$)—NH—, and —(CH$_2$)$_2$—NH—, where n is 1, 2, or 3; and wherein at least two of $R_4$-$R_6$ are hydrogen.

In certain embodiments, X is independently selected from a group consisting of —NH—, —NH—(O=C)—(C=OPh)H—, —NHC(=O)—, and —C(=O)NH—.

In certain embodiments, X is independently selected from a group consisting of —NH—, —NH—(O=C)—(C=OPh)H—, —NHC(=O)—, and —C(=O)NH—; and $R_4$-$R_6$ are hydrogen.

In certain embodiments, X is independently selected from a group consisting of —NH—, —NH—(O=C)—(C=OPh)H—, —NHC(=O)—, and —C(=O)NH—; and wherein at least two of $R_4$-$R_6$ are hydrogen.

In certain embodiments, the compounds are selected from the group consisting of ST Nos. 47-79 listed in Table 2 below, including pharmaceutically acceptable solvates, pharmaceutically acceptable prodrugs, pharmaceutically acceptable salts and pharmaceutically acceptable stereoisomers thereof.

TABLE 2

Compounds ST Nos. 47~79

| ST Nos. | Compounds |
|---|---|
| ST47 | |
| ST48 | |
| ST49 | |
| ST50 | |
| ST51 | |
| ST52 | |
| ST53 | |
| ST54 | |

TABLE 2-continued
Compounds ST Nos. 47~79
| ST Nos. | Compounds |
|---|---|
| ST55 | 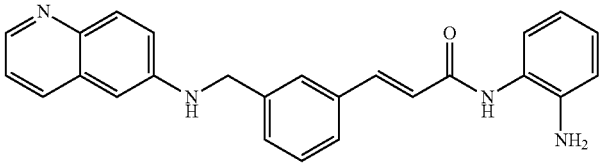 [SMILES: Nc1ccccc1NC(=O)/C=C/c1cccc(CNc2ccc3ncccc3c2)c1] |
| ST56 | 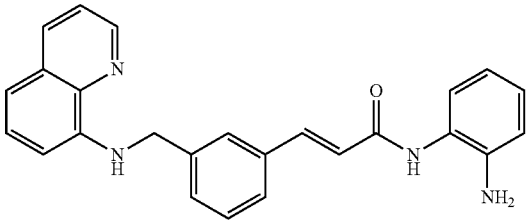 [SMILES: Nc1ccccc1NC(=O)/C=C/c1cccc(CNc2cccc3cccnc23)c1] |
| ST57 | 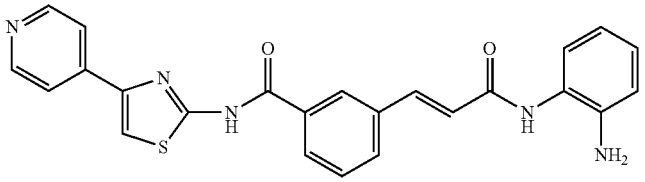 [SMILES: Nc1ccccc1NC(=O)/C=C/c1cccc(C(=O)Nc2nc(-c3ccncc3)cs2)c1] |
| ST58 | 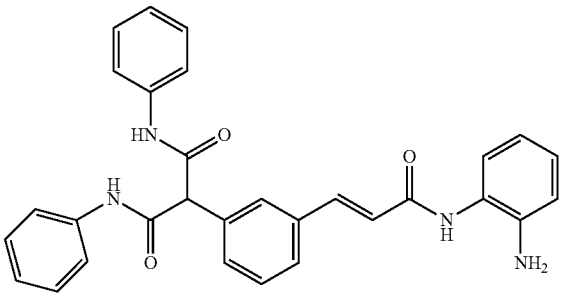 [SMILES: Nc1ccccc1NC(=O)/C=C/c1cccc(C(C(=O)Nc2ccccc2)C(=O)Nc2ccccc2)c1] |
| ST59 | 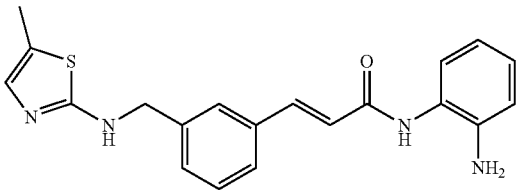 [SMILES: Cc1cnc(NCc2cccc(/C=C/C(=O)Nc3ccccc3N)c2)s1] |
| ST60 | 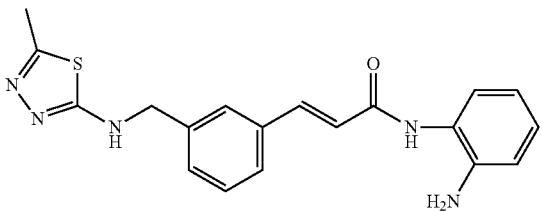 [SMILES: Cc1nnc(NCc2cccc(/C=C/C(=O)Nc3ccccc3N)c2)s1] |
| ST61 | 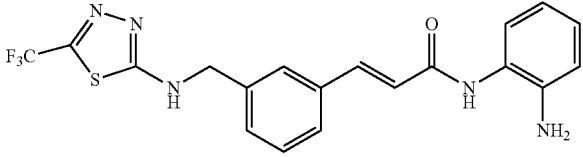 [SMILES: Nc1ccccc1NC(=O)/C=C/c1cccc(CNc2nnc(C(F)(F)F)s2)c1] |

TABLE 2-continued

Compounds ST Nos. 47~79

| ST Nos. | Compounds |
|---|---|
| ST62 | 4-(trifluoromethyl)thiazol-2-yl-aminomethyl connected to 3-substituted phenyl with (E)-acrylamide linked to 2-aminophenyl |
| ST63 | 4-(trifluoromethyl)oxazol-2-yl-aminomethyl connected to 3-substituted phenyl with (E)-acrylamide linked to 2-aminophenyl |
| ST64 | (E)-3-(pyridin-3-yl)acrylamide connected to 3-aminophenyl with (E)-acrylamide linked to 2-aminophenyl |
| ST65 | 5-methyl-1,3,4-oxadiazol-2-yl-aminomethyl connected to 3-substituted phenyl with (E)-acrylamide linked to 2-aminophenyl |
| ST66 | 4-methylthiazol-2-yl-aminomethyl connected to 3-substituted phenyl with (E)-acrylamide linked to 2-aminophenyl |
| ST67 | 4-methyloxazol-2-yl-aminomethyl connected to 3-substituted phenyl with (E)-acrylamide linked to 2-aminophenyl |
| ST68 | pyridin-3-ylmethyl carbamate of 3-aminophenyl with (E)-acrylamide linked to 2-aminophenyl |
| ST69 | 4-(pyridin-4-yl)thiazol-2-yl-amide of 3-substituted benzoyl with (E)-acrylohydroxamic acid |

TABLE 2-continued
Compounds ST Nos. 47~79
| ST Nos. | Compounds |
|---|---|
| ST70 | 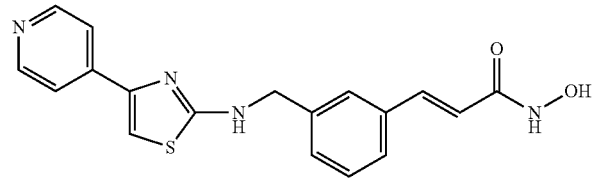 [SMILES: O=C(/C=C/c1cccc(CNc2nc(-c3ccncc3)cs2)c1)NO] |
| ST71 | 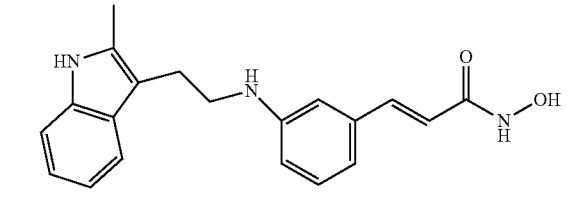 [SMILES: Cc1[nH]c2ccccc2c1CCNc1cccc(/C=C/C(=O)NO)c1] |
| ST72 | 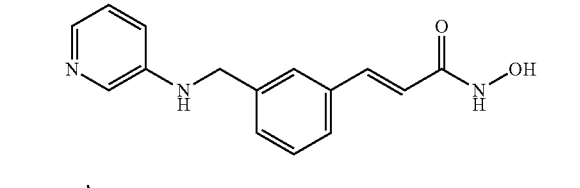 |
| ST73 | 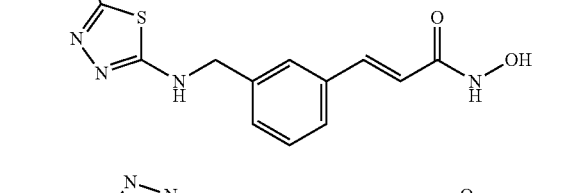 |
| ST74 | 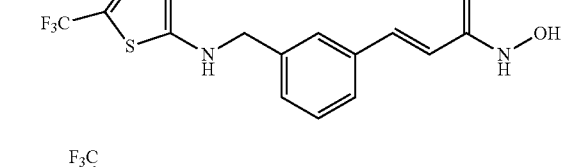 |
| ST75 | 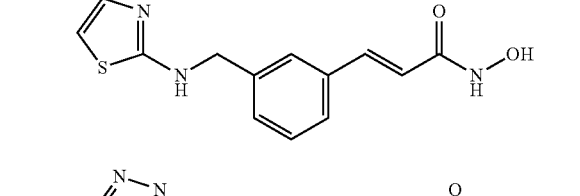 |
| ST76 | 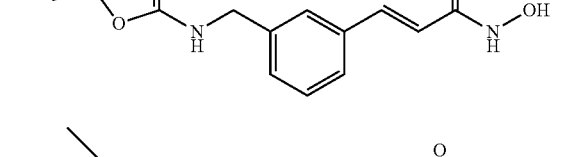 |
| ST77 | 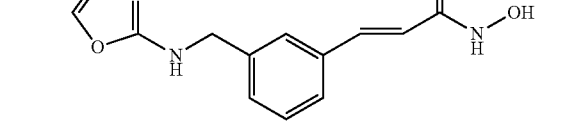 |

TABLE 2-continued

Compounds ST Nos. 47~79

| ST Nos. | Compounds |
|---|---|
| ST78 | |
| ST79 | |

Structure III

In certain embodiments, the compounds provided herein comprise a structure of Structure III:

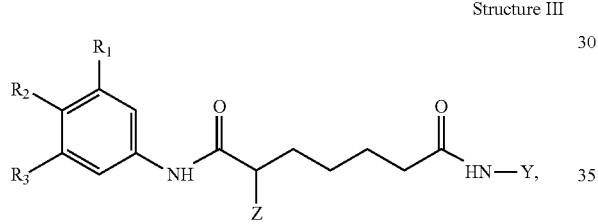

Structure III including pharmaceutically acceptable solvates, pharmaceutically acceptable prodrugs, pharmaceutically acceptable salts and pharmaceutically acceptable stereoisomers thereof, wherein:

Y is independently selected from the group consisting of 2-aminophenyl and hydroxyl;

$R_1$-$R_3$ are each independently selected from the group consisting of hydrogen, cyclopropyloxy, halogen, ethoxy, methoxy, methyl-mercaptan, ethoxy, ethyl, cyano, isopropyloxy, cyclobutyloxy, cyclopentyloxy, 3-oxetanyloxy, morpholinyl, 4-morpholinyl, dimethylamino, butyl, pyrrolidinyl, ethylmethylamino, piperidinyl, piperazinyl, diethylamino, dimethylaminomethyl, 3-oxetanyl, 2,2-difluoroethoxy, 1,1-difluoroethyl, methylsulfide, trifluoromethylsulfide, 2,2,2-trifluoroethoxy, and trifluoroethoxy, wherein at least one or two of $R_1$-$R_3$ are not hydrogen; and Z is independently selected from a group comprising, ethyl carbamate, methyl carbamate, amino, benzamide, pyridyl amide, n-butylamino, propionamide, butyramide, nicotinamide, 3-ethylimidazolidin-2-one, t-butylamino, picolinamide, 1-aminobutan-2-one, isopropyl carbamate, 2-cyclopropylacetamide, cyclopropylmethyl carbamate, and 3-methylbutanamide.

In certain embodiments, at least two of $R_1$-$R_3$ are hydrogen.

In certain embodiments, the compounds are selected from the group consisting of ST Nos. 80~114 listed in Table 3 below, including pharmaceutically acceptable solvates, pharmaceutically acceptable prodrugs, pharmaceutically acceptable salts and pharmaceutically acceptable stereoisomers thereof.

TABLE 3

Compounds ST Nos. 80~114

| ST Nos. | Compounds |
|---|---|
| ST80 | 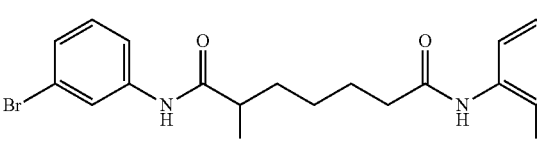 |

TABLE 3-continued
Compounds ST Nos. 80~114
| ST Nos. | Compounds |
|---|---|
| ST81 | 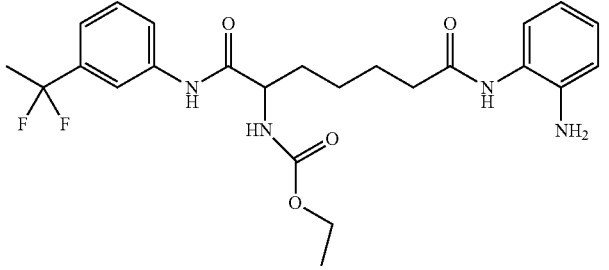 [SMILES: CCOC(=O)NC(CCCCC(=O)Nc1ccccc1N)C(=O)Nc1cccc(C(C)(F)F)c1] |
| ST82 | 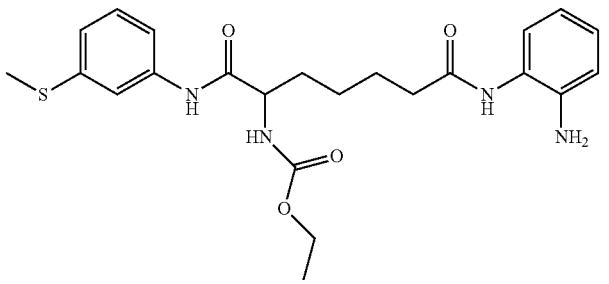 [SMILES: CCOC(=O)NC(CCCCC(=O)Nc1ccccc1N)C(=O)Nc1cccc(SC)c1] |
| ST83 | 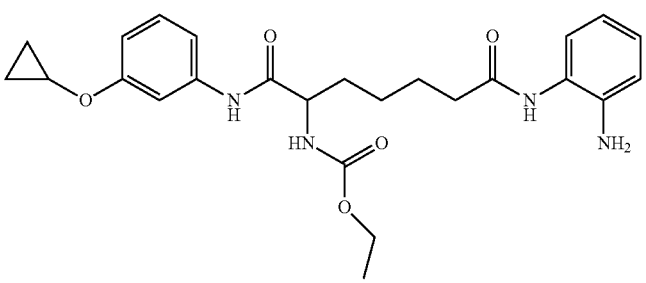 [SMILES: CCOC(=O)NC(CCCCC(=O)Nc1ccccc1N)C(=O)Nc1cccc(OC2CC2)c1] |
| ST84 | 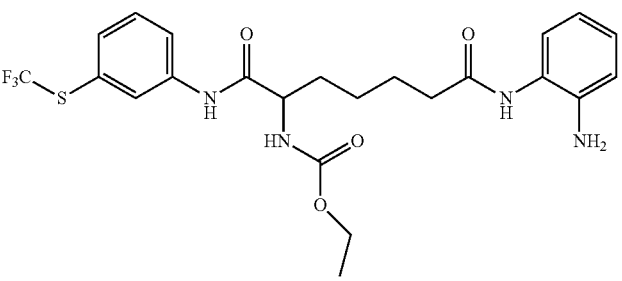 [SMILES: CCOC(=O)NC(CCCCC(=O)Nc1ccccc1N)C(=O)Nc1cccc(SC(F)(F)F)c1] |
| ST85 | 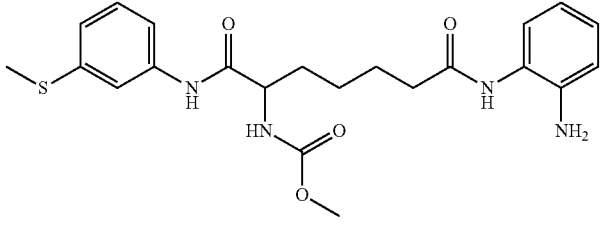 [SMILES: COC(=O)NC(CCCCC(=O)Nc1ccccc1N)C(=O)Nc1cccc(SC)c1] |

TABLE 3-continued

Compounds ST Nos. 80~114

| ST Nos. | Compounds |
|---|---|
| ST86 | (structure) |
| ST87 | (structure) |
| ST88 | (structure) |
| ST89 | (structure) |
| ST90 | (structure) |
| ST91 | (structure) |

TABLE 3-continued
Compounds ST Nos. 80~114
| ST Nos. | Compounds |
|---|---|
| ST92 | 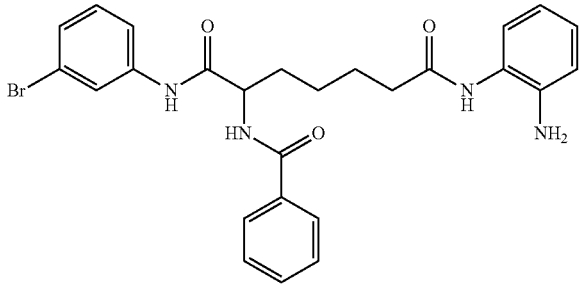 [SMILES: Nc1ccccc1NC(=O)CCCCC(NC(=O)c1ccccc1)C(=O)Nc1cccc(Br)c1] |
| ST93 | 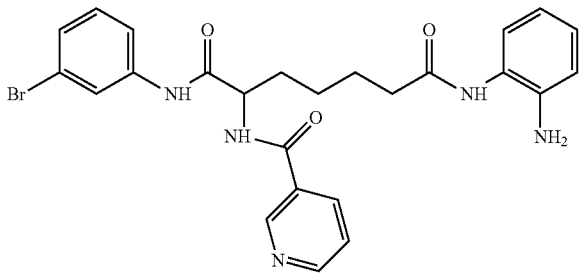 [SMILES: Nc1ccccc1NC(=O)CCCCC(NC(=O)c1cccnc1)C(=O)Nc1cccc(Br)c1] |
| ST94 | 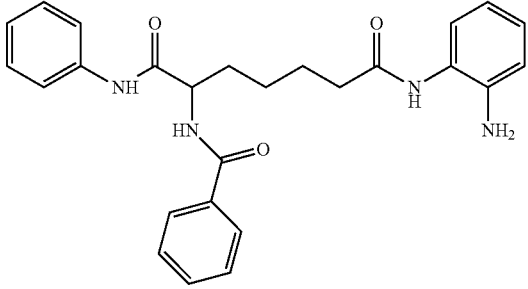 [SMILES: Nc1ccccc1NC(=O)CCCCC(NC(=O)c1ccccc1)C(=O)Nc1ccccc1] |
| ST95 | 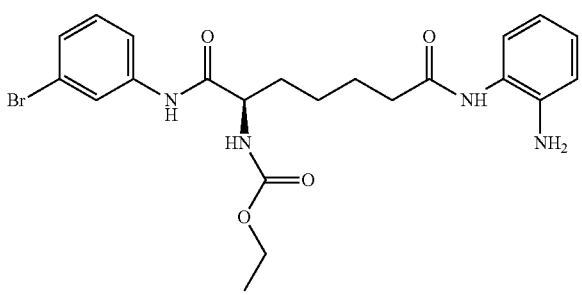 [SMILES: CCOC(=O)N[C@H](CCCCC(=O)Nc1ccccc1N)C(=O)Nc1cccc(Br)c1] |
| ST96 | 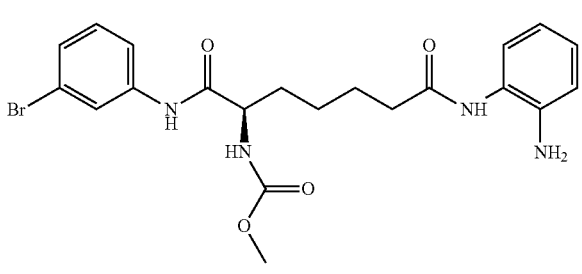 [SMILES: COC(=O)N[C@H](CCCCC(=O)Nc1ccccc1N)C(=O)Nc1cccc(Br)c1] |

TABLE 3-continued

Compounds ST Nos. 80~114

| ST Nos. | Compounds |
|---|---|
| ST97 | |
| ST98 | |
| ST99 | |
| ST100 | |
| ST101 | |
| ST102 | |

TABLE 3-continued
Compounds ST Nos. 80~114
| ST Nos. | Compounds |
|---|---|
| ST103 | 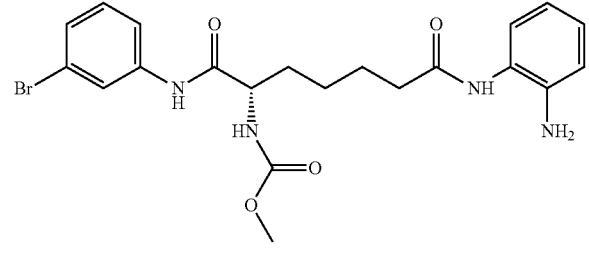 [SMILES: COC(=O)N[C@@H](CCCCC(=O)Nc1ccccc1N)C(=O)Nc1cccc(Br)c1] |
| ST104 | 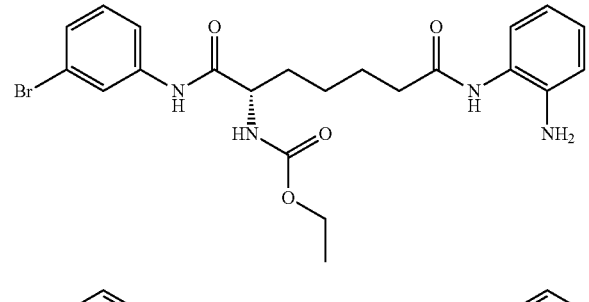 |
| ST105 | 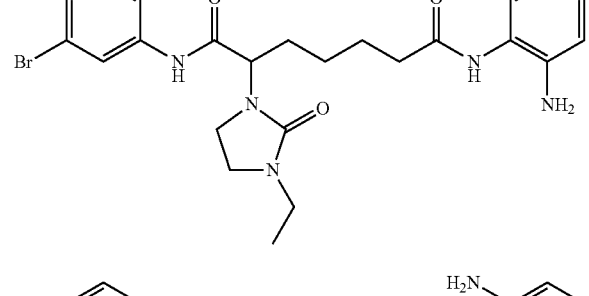 |
| ST106 | 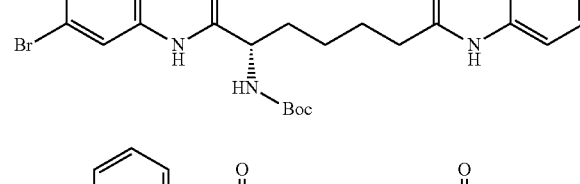 |
| ST107 | 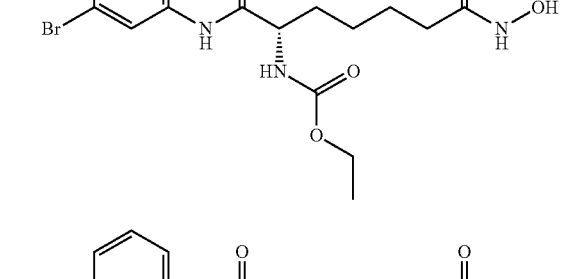 |
| ST108 | 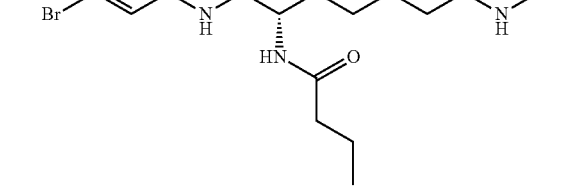 |

TABLE 3-continued
Compounds ST Nos. 80~114
| ST Nos. | Compounds |
|---|---|
| ST109 | 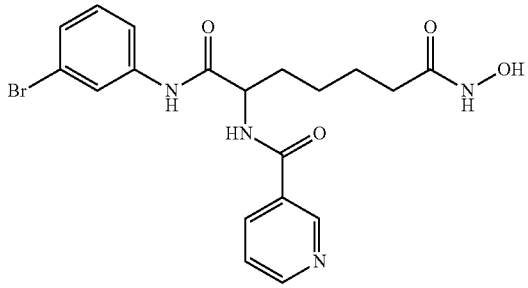 [SMILES: O=C(CCCCC(NC(=O)c1cccnc1)C(=O)Nc1cccc(Br)c1)NO] |
| ST110 | 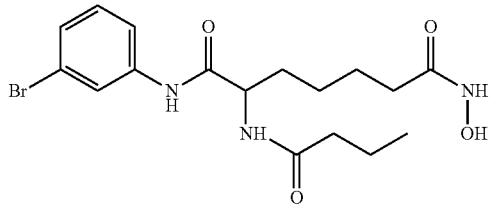 [SMILES: CCCC(=O)NC(CCCCC(=O)NO)C(=O)Nc1cccc(Br)c1] |
| ST111 | 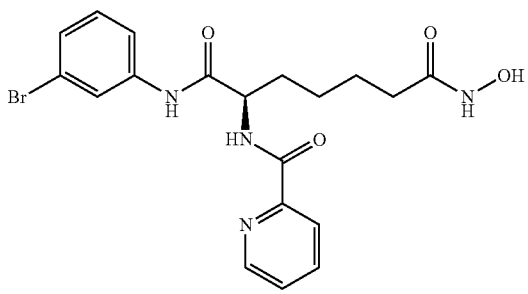 [SMILES: O=C(CCCC[C@@H](NC(=O)c1ccccn1)C(=O)Nc1cccc(Br)c1)NO] |
| ST112 | 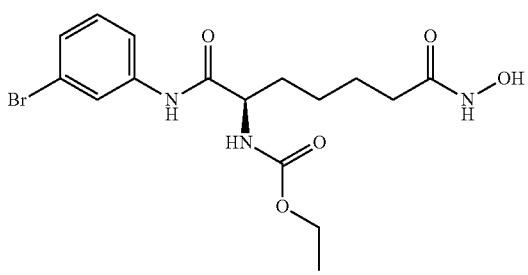 [SMILES: CCOC(=O)N[C@H](CCCCC(=O)NO)C(=O)Nc1cccc(Br)c1] |
| ST113 | 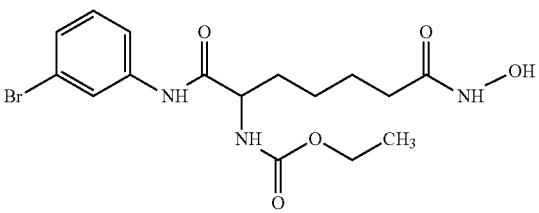 [SMILES: CCOC(=O)NC(CCCCC(=O)NO)C(=O)Nc1cccc(Br)c1] |

TABLE 3-continued

Compounds ST Nos. 80~114

| ST Nos. | Compounds |
|---|---|
| ST114 | 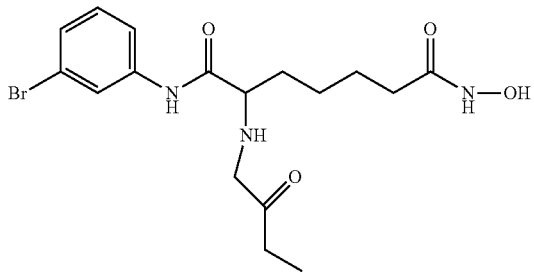 [SMILES: CCC(=O)CNC(CCCCC(=O)NO)C(=O)Nc1cccc(Br)c1] |

Structure IV

In certain embodiments, the compounds provided herein comprise a structure of Structure IV:

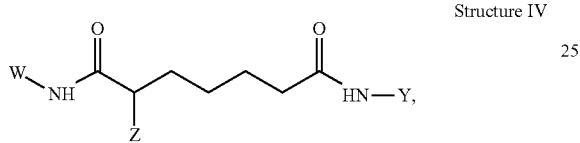

Structure IV including pharmaceutically acceptable solvates, pharmaceutically acceptable prodrugs, pharmaceutically acceptable salts and pharmaceutically acceptable stereoisomers thereof, wherein:

Y and Z are defined the same as above for Structure III; and

W is independently selected from the group consisting of cyclopropyl, benzene, 3-methoxy-pyridinyl, 4-(pyridin-4-yl)thiazolyl, 2-(2-Methyl-1H-indol-3-yl), pyridinyl, 3-ethoxy-pyridine, 5-methyl-1,3,4-thiadiazolyl, 5-(trifluoromethyl)-1,3,4-thiadiazolyl, 4-(trifluoromethyl)thiazolyl, 5-Methyl-1,3,4-oxadiazolyl, 4-methyloxazolyl, 4-methylthiazolyl, 4-(trifluoromethyl)oxazolyl, 4-(pyridin-3-yl)pyrimidinyl, benzo[d]thiazolyl, 4-(4-methoxyphenyl)thiazolyl, 4-(4-fluorophenyl)thiazolyl, 4-(pyridin-4-yl)thiazolyl, 2-Naphthalenyl, 6-Quinolinyl, 8-Quinolinyl, (E)-3-(pyridin-3-yl)acryloyl, pyridin-3-ylmethoxy, 3-Pyridinyl, and 5-methylthiazolyl.

In certain embodiments, the compounds are selected from the group consisting of ST Nos. 115~128 listed in Table 4 below, including pharmaceutically acceptable solvates, pharmaceutically acceptable prodrugs, pharmaceutically acceptable salts and pharmaceutically acceptable stereoisomers thereof.

TABLE 4

Compounds ST Nos. 115~128

| ST Nos. | Compounds |
|---|---|
| ST115 | 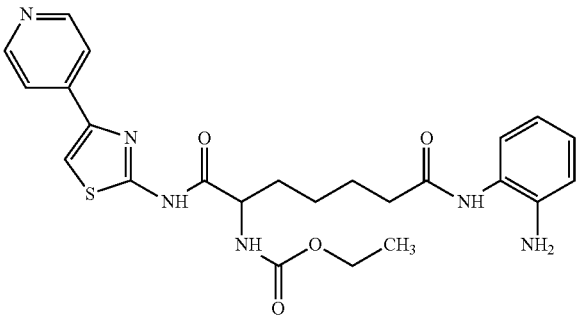 [SMILES: CCOC(=O)NC(CCCCC(=O)Nc1ccccc1N)C(=O)Nc1nc(-c2ccncc2)cs1] |

TABLE 4-continued

Compounds ST Nos. 115~128

| ST Nos. | Compounds |
| --- | --- |
| ST116 | |
| ST117 | |
| ST118 | |
| ST119 | |
| ST120 | |

TABLE 4-continued
Compounds ST Nos. 115~128
| ST Nos. | Compounds |
|---|---|
| ST121 | 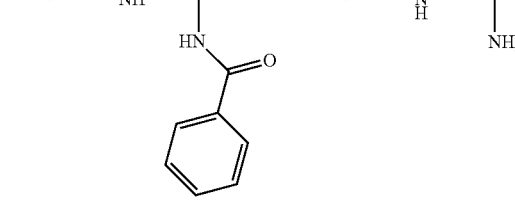 |
| ST122 | 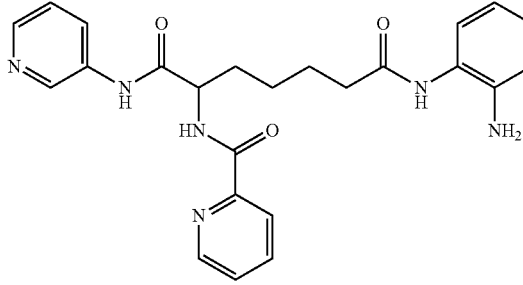 |
| ST123 | 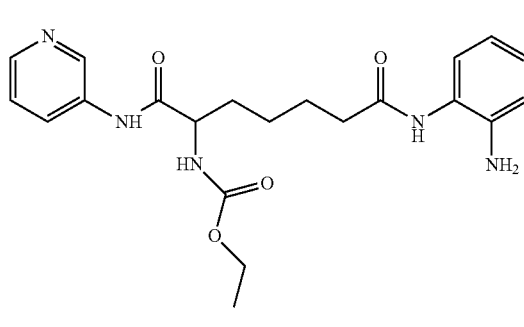 |
| ST124 | 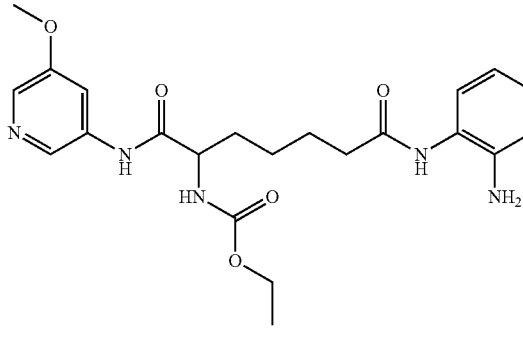 |
| ST125 | 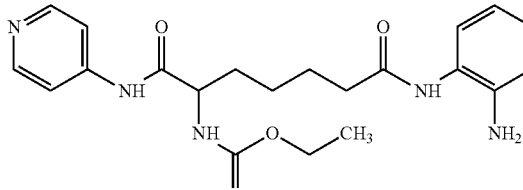 |

TABLE 4-continued

| Compounds ST Nos. 115~128 | |
|---|---|
| ST Nos. | Compounds |
| ST126 | 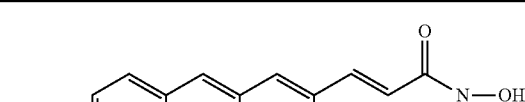 |
| ST127 | |
| ST128 | |

In certain embodiments, the compounds provided herein are selected from the group consisting of ST Nos. 30, 35, 36, and 129 listed below in Table 5, including pharmaceutically acceptable solvates, pharmaceutically acceptable prodrugs, pharmaceutically acceptable salts and pharmaceutically acceptable stereoisomers thereof.

TABLE 5

| Compounds ST Nos. 30, 35, and 36 | |
|---|---|
| ST Nos. | Compounds |
| ST30 |  |
| ST35 | |

TABLE 5-continued

Compounds ST Nos. 30, 35, and 36

| ST Nos. | Compounds |
|---|---|
| ST36 | *(structure: 4-methoxyphenyl-NH-CH2-cyclohexenyl-CH=CH-C(O)-NH-OH)* |
| ST129 | *(structure: bis(5-ethoxypyridin-3-yl-methyl) diamide with central ethoxycarbonylamino-substituted chain)* |

In certain embodiments, the compounds provided herein are MEF2 modulators.

In certain embodiments, the compounds provided herein increase MEF2 transcription.

In certain embodiments, the compounds provided herein decrease MEF2 transcription.

In certain embodiments, the compounds provided herein disrupt MEF2 and p300 interactions.

In certain embodiments, the compounds provided herein disrupt MEF2 and HDAC class IIa interactions.

As used herein, the term "modulate" (as in "modulator") means to act on as an activator, an inhibitor, or both.

As used herein, the term "halogen" or "halo" refers to fluorine (F), chlorine (Cl), bromine (Br) or iodine (I).

As used herein, the term "alkoxy" refers to an alkyl group wherein one or more hydrogen and/or carbon atoms are substituted with oxygen or hydroxyl group.

As used herein, the term "alkylamino" refers to an alkyl group wherein one or more hydrogen and/or carbon atoms are substituted with nitrogen or amino group.

As used herein, the term "haloalkyl" refers to an alkyl group wherein one or more hydrogen and/or carbon atoms are substituted with halogen atom.

As used herein, the term "substituted" refers to substitution(s) on one or more atoms, wherein each atom may be substituted with one or more substituents described above. Further examples of substitutions include, without limitation, halogen, alkoxy, alkylamino, haloalkyl, 3-methoxypyridinyl, 4-(pyridin-4-yl)thiazolyl, 2-(2-Methyl-1H-indol-3-yl), and alkylcarbonyl.

Unless otherwise specified, all substituents intend to include optionally substituted substituents, i.e. further substituted or not. For example, an alkyl group may be an unsubstituted alkyl group, or a substituted alkyl group as defined supra.

As used herein, a compound or a composition that is "pharmaceutically acceptable" is suitable for use in contact with the tissue or organ of a biological subject without excessive toxicity, irritation, allergic response, immunogenicity, or other problems or complications, commensurate with a reasonable benefit/risk ratio. If said compound or composition is to be used with other ingredients, said compound or composition is also compatible with said other ingredients.

As used herein, the term "solvate" refers to a complex of variable stoichiometry formed by a solute (e.g., compounds provided herein) and a solvent. Such solvents for the purpose of the disclosure may not interfere with the biological activity of the solute. Examples of suitable solvents include, but are not limited to, water, aqueous solution (e.g. buffer), methanol, ethanol and acetic acid. Preferably, the solvent used is a pharmaceutically acceptable solvent. Examples of suitable pharmaceutically acceptable solvents include, without limitation, water, aqueous solution (e.g. buffer), ethanol and acetic acid. Most preferably, the solvent used is water or aqueous solution (e.g. buffer). Examples for suitable solvates are the mono- or dihydrates or alcoholates of the compound according to the disclosure.

As used herein, pharmaceutically acceptable salts of a compound refers to any pharmaceutically acceptable acid and/or base additive salt of the compound (e.g., compounds provided herein). Suitable acids include organic and inorganic acids. Suitable bases include organic and inorganic bases. Examples of suitable inorganic acids include, but are not limited to: hydrochloric acid, hydrofluoric acid, hydrobromic acid, hydroiodic acid, sulfuric acid and boric acid. Examples of suitable organic acids include but are not limited to: acetic acid, trifluoroacetic acid, formic acid, oxalic acid, malonic acid, succinic acid, tartaric acid, maleic acid, fumaric acid, methanesulfonic acid, trifluoromethanesulfonic acid, benzoic acid, glycolic acid, lactic acid, citric acid and mandelic acid. Examples of suitable inorganic bases include, but are not limited to: ammonia, hydroxyethylamine and hydrazine. Examples of suitable organic bases include, but are not limited to, methylamine, ethylamine, trimethylamine, triethylamine, ethylenediamine, hydroxyethylamine, morpholine, piperazine and guanidine. The disclosure further provides for the hydrates and polymorphs of all of the compounds described herein.

According to some embodiments provided herein, a kit is provided that comprises one or more compounds disclosed herein or compositions or formulations thereof. In one embodiment, the kit may be used as a research tool to investigate the effect of transcription activity for MEF2, HDAC class IIa, or p300, by one or more compounds disclosed herein. In another embodiment, the kit may be used as a research tool to investigate the effect on the cellular processes of which MEF2, p300, and HDAC class IIa proteins are involved. In some embodiments, the cellular processes may include, but are not limited to, the transmission of extracellular signals to the genome and/or the activation of certain genetic programs in a cell. In some embodiments, the genetic programs may include, but are not limited to, genetic programs that control cell differentiation, proliferation, morphogenesis, survival and/or apoptosis.

II. Compositions

Provided herein in certain embodiments are compositions comprising one or more of the compounds provided herein. The compounds provided herein may contain one or more chiral atoms, or may otherwise be capable of existing as two or more stereoisomers, which are usually enantiomers and/or diastereomers. Accordingly, the compositions provided herein include mixtures of stereoisomers or mixtures of enantiomers, as well as purified stereoisomers, purified enantiomers, stereoisomerically enriched mixtures, or enantiomerically enriched mixtures. The compositions provided herein also include the individual isomers of the compound represented by the structures described above as well as any wholly or partially equilibrated mixtures thereof. The compositions provided herein also include the individual isomers of the compounds represented by the structures described above as mixtures with isomers thereof in which one or more chiral centers are inverted. Also, it is understood that all tautomers and mixtures of tautomers of the structures described above are included within the scope of the structures and preferably the structures corresponding thereto.

Racemates can be resolved into the isomers mechanically or chemically by methods known per se. Diastereomers are preferably formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid or the various optically active camphorsulfonic acids, such as camphorsulfonic acid. Also advantageous is enantiomer resolution with the aid of a column filled with an optically active resolving agent. The diastereomer resolution can also be carried out by standard purification processes, such as, for example, chromatography or fractional crystallization.

It is also possible to obtain optically active compounds comprising the structure of the compounds disclosed herein by the methods described above by using starting materials which are already optically active.

III. Pharmaceutical Formulations

As used herein, a pharmaceutical formulation comprises a therapeutically effective amount of one or more of the compounds or compositions provided herein. In certain embodiments, the pharmaceutical formulation further comprises a pharmaceutically acceptable carrier.

As used herein, a "therapeutically effective amount," "therapeutically effective concentration" or "therapeutically effective dose" is an amount which, as compared to a corresponding subject who has not received such amount, results in improved treatment, healing, prevention, or amelioration of a disease, disorder, or side effect, or a decrease in the rate of advancement of a disease or disorder.

This amount will vary depending upon a variety of factors, including but not limited to the characteristics of the compounds, compositions, or pharmaceutical formulations thereof (including activity, pharmacokinetics, pharmacodynamics, and bioavailability thereof), the physiological condition of the subject treated (including age, sex, disease type and stage, general physical condition, responsiveness to a given dosage, and type of medication) or cells, the nature of the pharmaceutically acceptable carrier or carriers in the formulation, and the route of administration. One skilled in the clinical and pharmacological arts will be able to determine an effective amount or therapeutically effective amount through routine experimentation, namely by monitoring a cell's or subject's response to administration of the one or more compounds disclosed herein or the pharmaceutical formulation thereof and adjusting the dosage accordingly. A typical dosage may range from about 0.1 mg/kg to about 100 mg/kg or more, depending on the factors mentioned above. In other embodiments, the dosage may range from about 0.1 mg/kg to about 100 mg/kg; or about 1 mg/kg to about 100 mg/kg; or about 5 mg/kg up to about 100 mg/kg. For additional guidance, see Remington: The Science and Practice of Pharmacy, 21st Edition, Univ. of Sciences in Philadelphia (USIP), Lippincott Williams & Wilkins, Philadelphia, Pa., 2005, which is hereby incorporated by reference as if fully set forth herein for additional guidance for determining a therapeutically effective amount.

As used herein, the term "about" refers to ±10%, ±5%, or ±1%, of the value following "about."

A "pharmaceutically acceptable carrier" is a pharmaceutically-acceptable material, composition or vehicle, such as a liquid or solid filler, diluent, excipient, solvent or encapsulating material, involved in carrying or transporting an active ingredient from one location, body fluid, tissue, organ (interior or exterior), or portion of the body, to another location, body fluid, tissue, organ, or portion of the body. Each carrier is "pharmaceutically acceptable" in the sense of being compatible with the other ingredients, e.g., the compounds or compositions described herein or other ingredients, of the formulation and suitable for use in contact with the tissue or organ of a biological subject without excessive toxicity, irritation, allergic response, immunogenicity, or other problems or complications, commensurate with a reasonable benefit/risk ratio.

Pharmaceutically acceptable carriers are well known in the art and include, without limitation, (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations.

The pharmaceutical formulations disclosed herein may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of the one or more compounds or compositions thereof in the pharmaceutical formulations provided herein can vary widely, and will be selected primarily based on fluid volumes, viscosities, body weight and the like in accordance with the particular mode of administration selected and the biological subject's needs. For example, the concentration of the one or more compounds disclosed herein can be about 0.0001% to about 100%, about 0.001% to about 50%, about 0.01% to about 30%, about 0.1% to about 20%, about 1% to about 10% wt.

A suitable pharmaceutically acceptable carrier may be selected taking into account the chosen mode of administration, and the physical and chemical properties of the compounds.

One skilled in the art will recognize that a pharmaceutical formulation containing the one or more compounds provided herein or compositions thereof can be administered to a subject by various routes including, without limitation, orally or parenterally, such as intravenously. The composition may also be administered through subcutaneous injection, subcutaneous embedding, intragastric, topical, and/or vaginal administration. The composition may also be administered by injection or intubation.

In one embodiment, the pharmaceutical carrier may be a liquid and the pharmaceutical formulation would be in the form of a solution. In another embodiment, the pharmaceutically acceptable carrier is a solid and the pharmaceutical formulation is in the form of a powder, tablet, pill, or capsules. In another embodiment, the pharmaceutical carrier is a gel and the pharmaceutical formulation is in the form of a suppository or cream.

A solid carrier can include one or more substances which may also act as flavoring agents, lubricants, solubilizers, suspending agents, fillers, glidants, compression aids, binders or table-disintegrating agents, it can also be an encapsulating material. In powders, the carrier is a finely divided solid that is in admixture with the finely divided active ingredient. In tablets, the active-ingredient is mixed with a carrier having the necessary compression properties in suitable proportions and compacted in the shape and size desired. The powders and tablets preferably contain up to about 99% of the one or more compounds disclosed herein. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Besides containing an effective amount of the one or more compounds provided herein or compositions thereof, the pharmaceutical formulations may also include suitable diluents, preservatives, solubilizers, emulsifiers, adjuvant and/or carriers.

The pharmaceutical formulation can be administered in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

Additional pharmaceutical formulations will be evident to those skilled in the art, including formulations involving binding agent molecules in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, PCT/US93/0082948 which is incorporated herein by reference as if fully set forth herein for the techniques of controlled release of porous polymeric microparticles for the delivery of pharmaceutical formulations. Additional examples of sustained-release preparations include semipermeable polymer matrices in the form of shaped articles, e.g. films, or microcapsules. Sustained release matrices may include polyesters, hydrogels, polylactides, copolymers of L-glutamic acid and gamma ethyl-L-glutamate, poly (2-hydroxyethyl-methacrylate), ethylene vinyl acetate or poly-D (−)-3-hydroxybutyric acid. Sustained-release compositions also include liposomes, which can be prepared by any of several methods known in the art.

IV. Methods of preparation

Another aspect of the disclosure relates to the preparation of the compounds disclosed herein.

In one embodiment, one or more compounds disclosed herein are synthesized according the synthesis schemes (methods) disclosed herein in Examples 1-18.

In one embodiment, one or more compounds disclosed herein are synthesized according to the synthesis schemes (methods) presented below in the two Examples of 1 and 15.

EXAMPLES

As used herein, "DIPEA" is N,N-Diisopropylethylamine; "PE" is Petroleum ether; "EA" is Ethyl Acetate; "CDMT" is 2-Chloro-4,6-dimethoxy-1,3,5-triazine; "NMM" is N-methylmorpholine; "HBTU" is (2-(1H-benzotriazol-1-yl)-1,1,3,3-tetramethyluronium hexafluorophosphate); "DCC" is N,N'-Dicyclohexylcarbodiimide; "DCE" is 1,2-Dichloroethane; "DCM" is Dichloromethane; "ACN" is Acetonitrile; "TEA" is Triethylamine; "TFA" is Trifluoroacetic acid; "DMF" is Dimethylformamide: "DMAP" is 4-Dimethylaminopyridine; "ON" is over night; and "r.t." is room temperature.

Example 1

Synthesis of ST7 [(E)-N-(2-aminophenyl)-3-(3-(((3-cyclopropoxyphenyl)amino)methyl)phenyl)acrylamide]

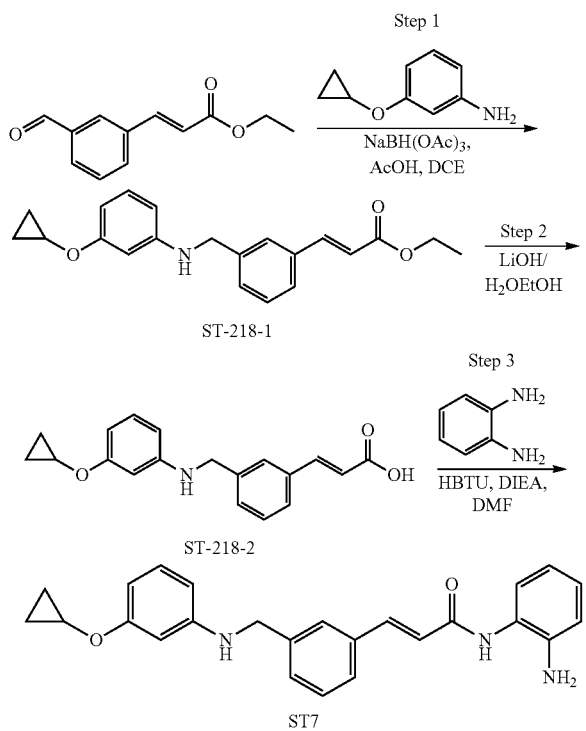

Step 1. The Synthesis of ST-218-1 [ethyl (E)-3-(3-(((3-cyclopropoxyphenyl)amino)methyl)phenyl)acrylate]

Step 3. The Synthesis of ST7 [(E)-N-(2-aminophenyl)-3-(3-(((3-cyclopropoxyphenyl)amino)methyl)phenyl)acrylamide]

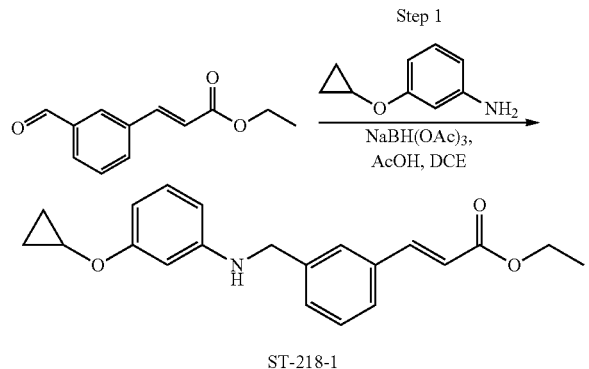

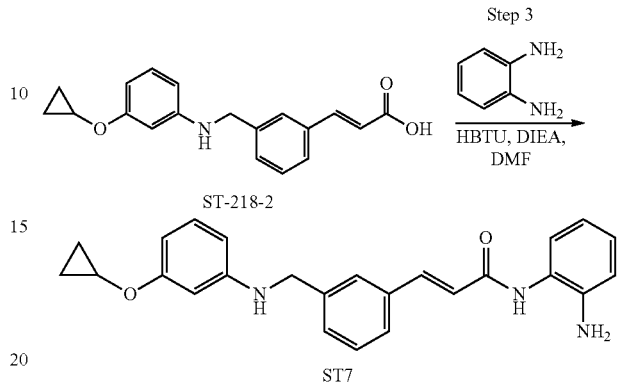

NaBH(OAc)$_3$ (583 mg, 2.682 mmol) was added to a mixture solution of 3-cyclopropoxyaniline (200 mg, 1.341 mmol), (E)-ethyl 3-(3-formylphenyl)acrylate (280 mg, 1.341 mmol) and acetic acid (1 drop) in DCE (5 mL) and stirred at room temperature overnight. The solvent was diluted with water (20 mL) and extracted with EA (10 mL×3). The combined organic phase was dried, concentrated and the residue was purified by flash column chromatography to give ST-218-1 (250 mg, Yield: 55.3%).

Step 2. The Synthesis of ST-218-2 [(E)-3-(3-(((3-cyclopropoxyphenyl)amino)methyl)phenyl)acrylic acid]

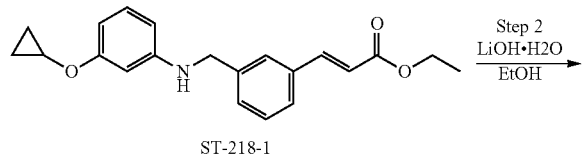

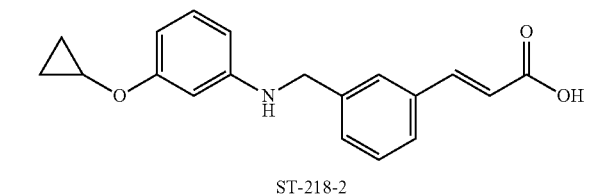

To a solution of ST-218-1 (250 mg, 0.741 mmol) in EtOH (5 mL), LiOH.H$_2$O (156 mg, 3.705 mmol) was added. The solution was stirred at room temperature overnight. When the reaction was completed, the organic phase was removed, and the residue was re-dissolved in water (10 mL). The solution was adjusted to pH=4-6 with HCl (1 M) at room temperature. The suspension solution was filtered. The desired product ST-218-2 was isolated (200 mg, Yield: 87.2%).

To a solution of ST-218-2 (200 mg, 0.646 mmol) in DMF (5 mL), HBTU (336 mg, 0.877 mmol) and DIEA (110 mg, 0.877 mmol) were added. The solution was stirred for 30 min at room temperature. The benzene-1, 2-diamine (97 mg, 0.887 mmol) was added. The mixture was stirred at room temperature overnight. When the reaction was completed, the reaction mixture was poured into ice-water (20 mL) and then the mixture was extracted with EA (20 mL×2). The organic layer was combined, washed with brine, and dried over anhydrous Na$_2$SO$_4$. The mixture was purified by column chromatography and prep-HPLC to give ST7 (15 mg, Yield: 5.8%).

j LC-MS: m/z=400.2020 ([M+H]$^+$).

$^1$H NMR (500 MHz, DMSO-d$_6$) δ 0.56 (m, 2H), 0.67 (m, 2H), 3.66 (m, 1H), 4.27 (d, J=5.8 Hz, 2H), 4.94 (s, 2H), 6.24 (m, 3H), 6.32 (m, 1H), 6.57 (m, 1H), 6.75 (d, J=7.9 Hz, 1H), 6.84-6.98 (m, 3H), 7.30-7.43 (m, 3H), 7.45-7.57 (m, 2H), 7.61 (s, 1H), 9.38 (s, 1H).

Example 2

Synthesis of ST119 [methyl (7-((2-aminophenyl)amino)-1,7-dioxo-1-(quinolin-8-ylamino)heptan-2-yl)carbamate]

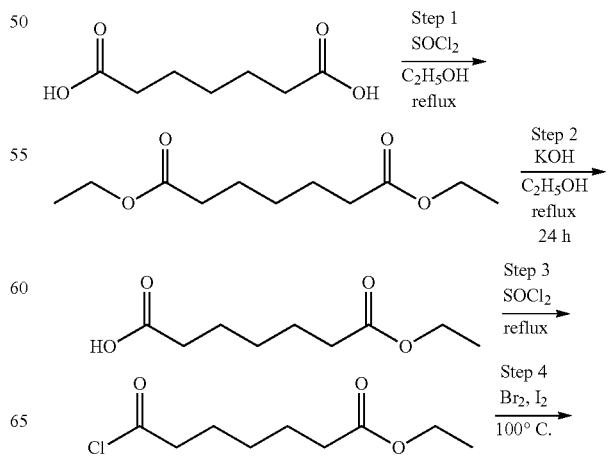

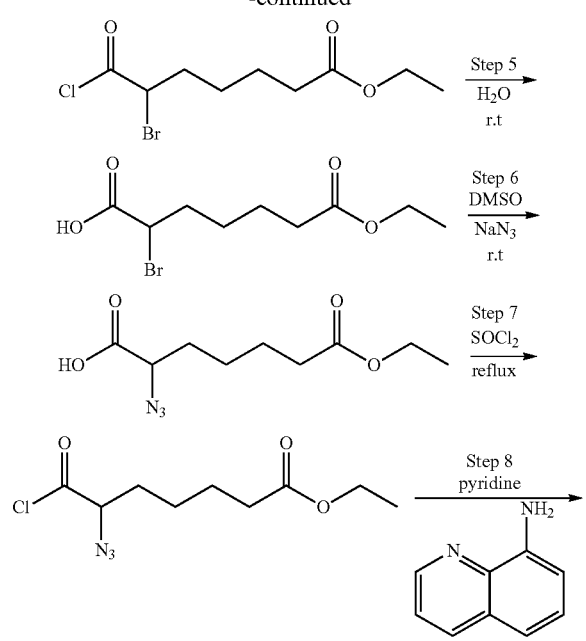

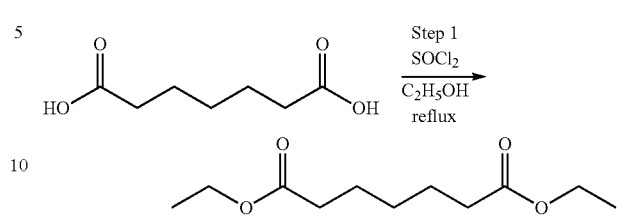

Step 1. Synthesis of Diethyl Heptanedioate

To a solution of heptanedioic acid (150 g, 0.94 mol) in 300 mL ethanol, thionyl chloride (50 ml) was added dropwise at 0° C. over 0.5 hour, then the reaction mixture was stirred at 85° C. for 10 hours. When the reaction was completed, the mixture was concentrated under reduced pressure. The resulting mixture was poured into water and extracted with EtOAc (250 mL×3). The organic layers were washed with saturated aqueous solution of $Na_2CO_3$, dried over anhydrous $Na_2SO_4$ and concentrated to give the desired compound (202 g, yield: 99%).

Step 2. Synthesis of 7-ethoxy-7-oxoheptanoic acid

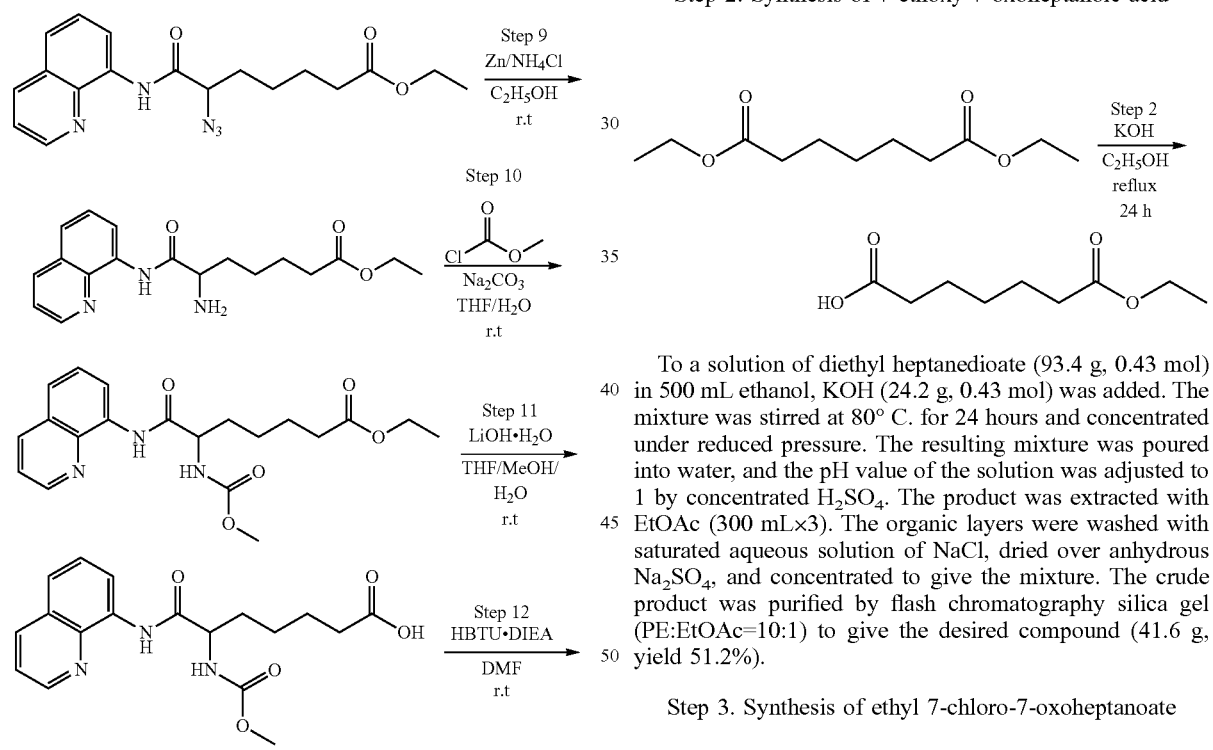

To a solution of diethyl heptanedioate (93.4 g, 0.43 mol) in 500 mL ethanol, KOH (24.2 g, 0.43 mol) was added. The mixture was stirred at 80° C. for 24 hours and concentrated under reduced pressure. The resulting mixture was poured into water, and the pH value of the solution was adjusted to 1 by concentrated $H_2SO_4$. The product was extracted with EtOAc (300 mL×3). The organic layers were washed with saturated aqueous solution of NaCl, dried over anhydrous $Na_2SO_4$, and concentrated to give the mixture. The crude product was purified by flash chromatography silica gel (PE:EtOAc=10:1) to give the desired compound (41.6 g, yield 51.2%).

Step 3. Synthesis of ethyl 7-chloro-7-oxoheptanoate

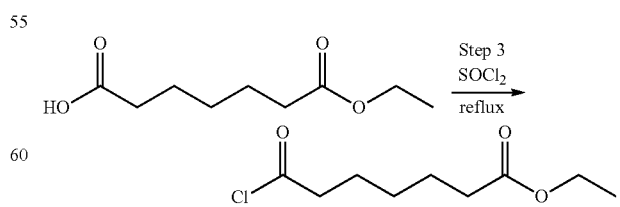

7-ethoxy-7-oxoheptanoic acid (41.6 g, 0.22 mol) was added into 80 mL thionyl chloride, then the mixture was heated to reflux for 3 hours. When the reaction was completed, the mixture was concentrated under reduced pressure. The crude product was used for next step without further purified (45.6 g, yield: 99%).

Step 4. Synthesis of ethyl 6-bromo-7-chloro-7-oxoheptanoate

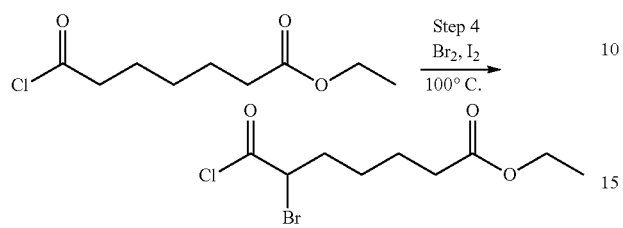

To a solution of I$_2$ (5.63 g, 0.022 mol) in 7-chloro-7-oxoheptanoate (45.6 g, 0.22 mol), Br$_2$ (35.4 g, 0.22 mol) was added at 100° C. When the reaction was completed, the mixture was allowed to cold to room temperature. The crude product was used for next step without further purified.

Step 5. Synthesis of 2-bromo-7-ethoxy-7-oxoheptanoic acid

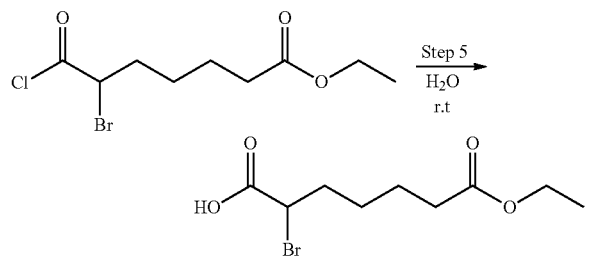

Ethyl 6-bromo-7-chloro-7-oxoheptanoate (crude) was added to water (200 mL), and then the mixture solution was stirred at room temperature overnight. When the reaction was completed, the solution was extracted with EtOAc (100 mL×3). The organic layers were combined, washed with saturated aqueous solution of NaCl, dried over anhydrous Na$_2$SO$_4$ and concentrated to give the residue. The crude product was purified by flash chromatography silica gel (PE:EtOAc=8:1) to give the desired compound (23.8 g, yield: 40.1%).

Step 6. Synthesis of 2-azido-7-ethoxy-7-oxoheptanoic acid

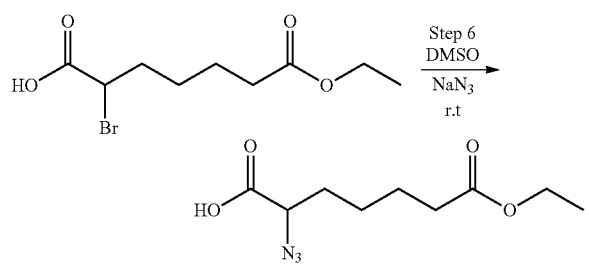

To a solution of 2-bromo-7-ethoxy-7-oxoheptanoic acid (23.8 g, 0.089 mol) in 30 mL DMSO, NaN$_3$ (8.69 g, 0.134 mol) and Na$_2$CO$_3$ (14.2 g, 0.134 mol) were added at room temperature. The solution was stirred at room temperature overnight. When the reaction was completed, the solution was adjusted to pH=5 by concentrated HCl. The solution was extracted with EtOAc (100 mL×3). The organic layer was combined, washed with brine, dried over Na$_2$SO$_4$ and concentrated under reduced pressure. The product was used for next step without further purified (20.4 g, crude).

Step 7. Synthesis of ethyl 6-azido-7-chloro-7-oxoheptanoate

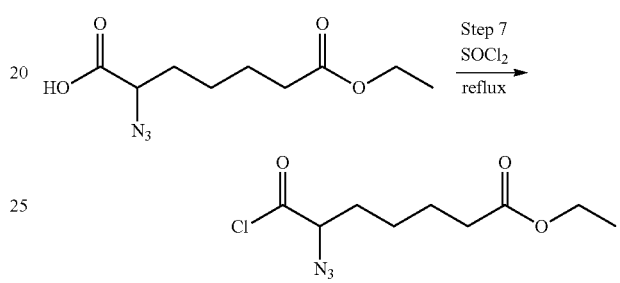

2-azido-7-ethoxy-7-oxoheptanoic acid (12.0 g, 0.052 mol) was added in 30 mL thionyl chloride. The mixture was stirred at 85° C. for 3 hours. When the reaction was completed, the mixture was concentrated under reduced pressure. The crude product was used for next step without further purified (13.0 g, yield: 99%).

Step 8. Synthesis of ethyl 6-azido-7-oxo-7-(quinolin-8-ylamino)heptanoate

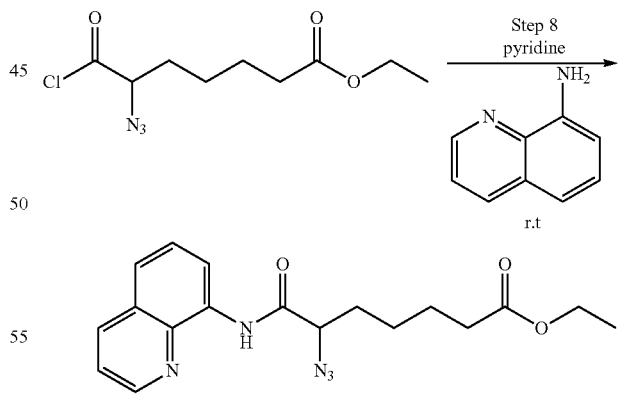

To a solution of quinolin-8-amine (7.55 g, 0.052 mmol) in 30 mL pyridine, ethyl 6-azido-7-chloro-7-oxoheptanoate (13.0 g, 0.052 mmol) was added dropwise at 0° C. The solution was stirred at room temperature overnight. When the reaction was completed, the solution was concentrated and purified by column chromatography on silica gel (Pet:EtOAc=4:1) to give the desired compound as brown oil (10.8 g, yield: 58.4%).

Step 9. Synthesis of ethyl 6-amino-7-oxo-7-(quinolin-8-ylamino)heptanoate

Step 11. Synthesis of 6-((methoxycarbonyl)amino)-7-oxo-7-(quinolin-8-ylamino)heptanoic acid

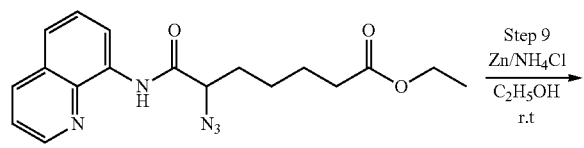

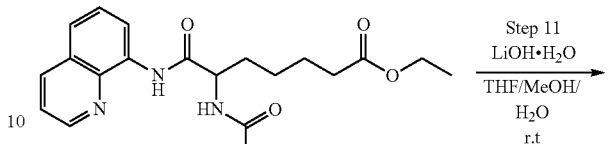

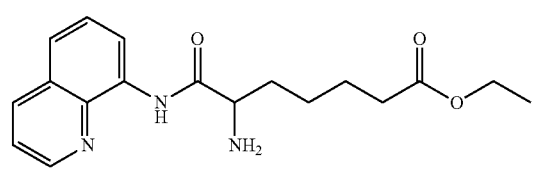

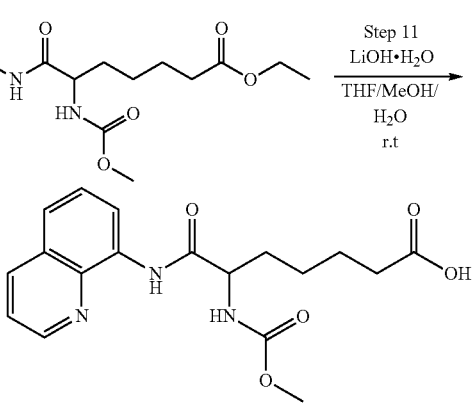

To a solution of ethyl 6-azido-7-oxo-7-(quinolin-8-ylamino)heptanoate (10.8 g, 0.028 mol) in 100 mL ethanol, zinc (5.5 g, 0.084 mol) and saturated aqueous solution of $NH_4Cl$ (50 mL) were added at room temperature. When the reaction was completed, the mixture was concentrated under reduced pressure. The product was purified by column chromatography on silica gel (EtOH:EtOAc=1:10) to give the desired compound as brown oil (9.0 g, yield: 97.5%).

To a solution of ethyl 6-((methoxycarbonyl)amino)-7-oxo-7-(quinolin-8-ylamino)heptanoate (11.6 g, 0.3 mol) in THF/MeOH/$H_2O$ (40/40/10 mL), LiOH·$H_2O$ (6.3 g, 0.15 mol) was added at room temperature. The solution was stirred at room temperature for 3 hours. When the reaction was completed, the mixture was adjusted to pH=5 by HCl solution. The mixture was extracted with $CH_2Cl_2$ (100 mL×3). The organic layers were combined, washed with brine, dried over $Na_2SO_4$ and concentrated under reduced pressure to give the desired compound as colorless oil without further purification (9.0 g, yield: 83.4%).

Step 10. Synthesis of ethyl 6-((methoxycarbonyl)amino)-7-oxo-7-(quinolin-8-ylamino)heptanoate

Step 12. Synthesis of ST119 [methyl (7-((2-aminophenyl)amino)-1,7-dioxo-1-(quinolin-8-ylamino)heptan-2-yl)carbamate]

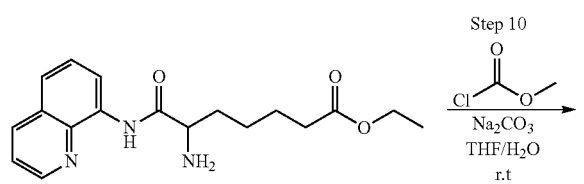

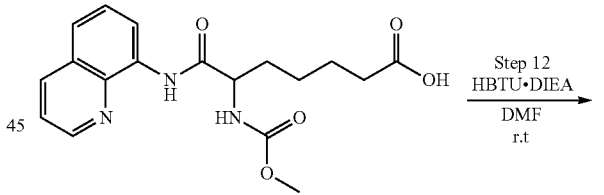

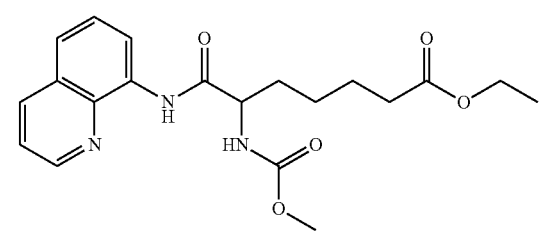

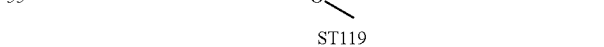

ST119

To a solution of ethyl 6-amino-7-oxo-7-(quinolin-8-ylamino)heptanoate (9.0 g, 0.027 mol) in THF/$H_2O$ (50/10 mL), $Na_2CO_3$ (3.2 g, 0.03 mol) and methyl carbonochloridate (4.2 g, 0.045 mol) were added at 0° C. The mixture was stirred at room temperature for 2 hours. When the reaction was completed, the solution was concentrated under reduced pressure. The solution was extracted with $CH_2Cl_2$ (100 mL×3). The organic layers were combined, washed with brine and concentrated for next step without further purification (11.6 g).

To a solution of 6-((methoxycarbonyl) amino)-7-oxo-7-(quinolin-8-ylamino)heptanoic acid (9.0 g, 0.025 mol) in 50 mL DMF, HBTU (10.4 g, 0.028 mol), DIEA (9.7 g, 0.075 mol) and benzene-1,2-diamine (8.1 g, 0.075 mol) were added at room temperature. The mixture was stirred at room temperature overnight. When the reaction was completed, the mixture was poured into water (1 L) and extracted with $CH_2Cl_2$ (200 mL×2). The organic layers were combined, washed with brine, dried over $Na_2SO_4$, concentrated and purified by column chromatography on silica gel (CH$_2$Cl$_2$:MeOH=100:1) to give the desired compound as a yellow solid, ST119 (5.8 g, yield: 80.1%).

Purity: 98.4% (LC-MS, 254 nm)

$^1$H NMR (400 MHz, DMSO-d$_6$) δ 1.40-1.51 (m, 2H), 1.63 (m, 2H), 1.72 (m, 1H), 1.89 (m, 1H), 2.32 (t, J=7.3 Hz, 2H), 3.60 (s, 3H), 4.25 (t, J=10.7 Hz, 1H), 4.80 (s, 2H), 6.51 (m, 1H), 6.71 (dd, J=8.0, 1.2 Hz, 1H), 6.90 (m, 1H), 7.13 (dd, J=8.3, 1.1 Hz, 1H), 7.59 (t, J=8.0 Hz, 1H), 7.65 (dd, J=8.3, 4.2 Hz, 1H), 7.69 (dd, J=8.3, 1.1 Hz, 1H), 7.93 (d, J=7.1 Hz, 1H), 8.43 (dd, J=8.3, 1.6 Hz, 1H), 8.64 (dd, J=8.3, 1.1 Hz, 1H), 8.92 (dd, J=4.2, 1.6 Hz, 1H), 9.07 (s, 1H), 10.43 (s, 1H).

LC-MS: m/z=450.2 ([M+H]$^+$).

Example 3

Synthesis of ST100

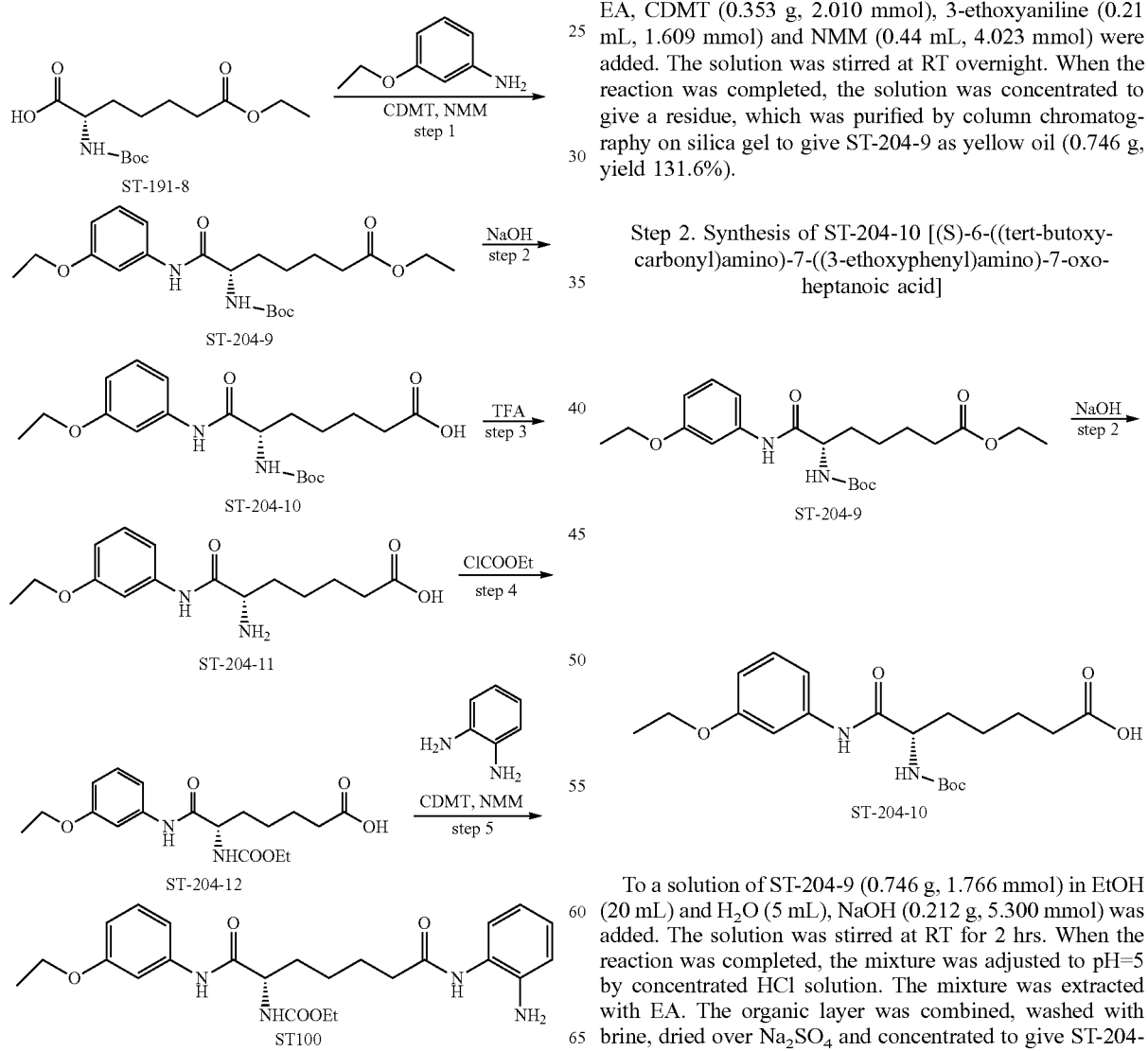

Step 1. Synthesis of ST-204-9 [(S)-ethyl 6-((tert-butoxycarbonyl)amino)-7-((3-ethoxyphenyl)amino)-7-oxoheptanoate]

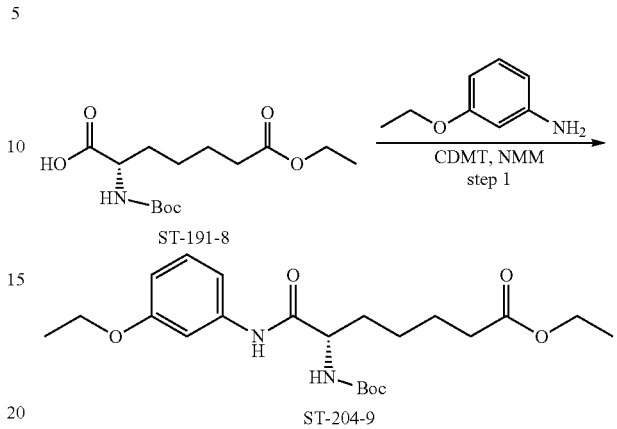

To a solution of ST-191-8 (0.407 g, 1.341 mmol) in 30 mL EA, CDMT (0.353 g, 2.010 mmol), 3-ethoxyaniline (0.21 mL, 1.609 mmol) and NMM (0.44 mL, 4.023 mmol) were added. The solution was stirred at RT overnight. When the reaction was completed, the solution was concentrated to give a residue, which was purified by column chromatography on silica gel to give ST-204-9 as yellow oil (0.746 g, yield 131.6%).

Step 2. Synthesis of ST-204-10 [(S)-6-((tert-butoxycarbonyl)amino)-7-((3-ethoxyphenyl)amino)-7-oxo-heptanoic acid]

To a solution of ST-204-9 (0.746 g, 1.766 mmol) in EtOH (20 mL) and H$_2$O (5 mL), NaOH (0.212 g, 5.300 mmol) was added. The solution was stirred at RT for 2 hrs. When the reaction was completed, the mixture was adjusted to pH=5 by concentrated HCl solution. The mixture was extracted with EA. The organic layer was combined, washed with brine, dried over Na$_2$SO$_4$ and concentrated to give ST-204-10 as yellow oil without further purification. (0.526 g, yield 75.5%)

Step 3. Synthesis of ST-204-11 [(S)-6-amino-7-((3-ethoxyphenyl)amino)-7-oxoheptanoic acid]

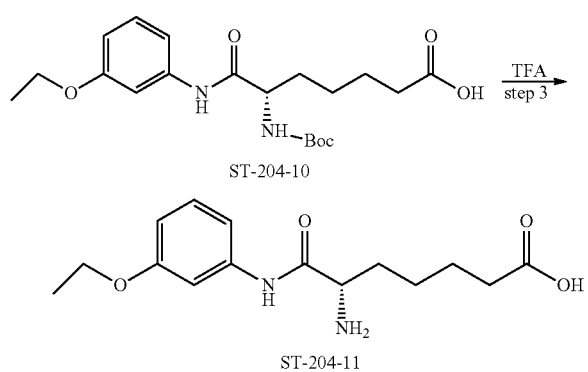

TFA (0.20 mL, 2.666 mmol) was added to a solution of ST-204-10 (0.526 g, 1.333 mmol) in 20 mL CH$_2$Cl$_2$ at 0° C. The solution was stirred at RT overnight. When the reaction was completed, the mixture was concentrated to give ST-204-11 as yellow oil without further purification (0.392 g, yield 100%).

Step 4. Synthesis of ST-204-12 [(S)-6-((ethoxycarbonyl)amino)-7-((3-ethoxyphenyl)amino)-7-oxoheptanoic acid]

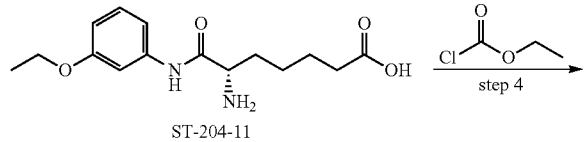

Na$_2$CO$_3$ (0.707 g, 6.670 mmol) and ethyl carbonochloridate (0.15 mL, 1.600 mmol) were added to a solution of ST-204-11 (0.392 g, 1.332 mmol) in 1, 4-dioxane (30 mL). The mixture was stirred at RT overnight. When the reaction was completed, the solution was concentrated and 30 mL water was added. Then the mixture was adjusted to pH=5 by HCl solution and extracted with EA. The organic layer was combined, washed with brine, dried over Na$_2$SO$_4$ and concentrated to give the crude product of ST-204-12 as yellow oil without further purification (0.712 g, yield 145.9%).

Step 5. Synthesis of ST100 [(S)-ethyl (7-((2-aminophenyl)amino)-1-((3-ethoxyphenyl)amino)-1,7-dioxoheptan-2-yl)carbamate]

CDMT (0.512 g, 2.916 mmol), benzene-1,2-diamine (0.630 g, 5.828 mmol) and NMM (0.64 mL, 5.828 mmol) were added to a solution of ST-204-12 (0.712 g, 1.943 mmol) in 30 mL EA. The solution was stirred at RT overnight. When the reaction was completed, the solution was concentrated to give a residue, which was purified by column chromatography on silica gel to give ST100 as a yellow solid (0.411 g, yield 46.3%).

Purity: 97.8% (LC-MS, 254 nm)

$^1$H NMR (500 MHz, DMSO-d$_6$): δ 1.16 (t, J=7.0 Hz, 3H), 1.31 (t, J=7.0 Hz, 3H), 1.35-1.46 (m, 2H), 1.56-1.72 (m, 4H), 2.31 (t, J=7.2 Hz, 2H), 3.96-4.01 (m, 4H), 4.08-4.13 (m, 1H), 4.80 (s, 2H), 6.50-6.53 (m, 1H), 6.60-6.62 (m, 1H), 6.71 (dd, J=8.0, 1.5 Hz, 1H), 6.86-6.90 (m, 1H), 7.10-7.20 (m, 3H), 7.30-7.36 (m, 2H), 9.06 (s, 1H), 9.97 (s, 1H).

LC-MS: m/z=457.3 ([M+H]$^+$).

Example 4

Synthesis of ST63

63

-continued

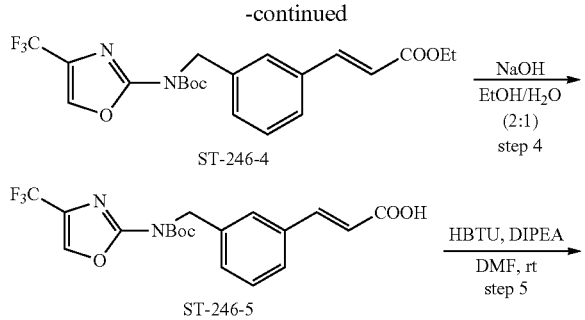

64

Step 1. Synthesis of ST-246-2 [tert-butyl 4-(trifluoromethyl)oxazol-2-ylcarbamate]

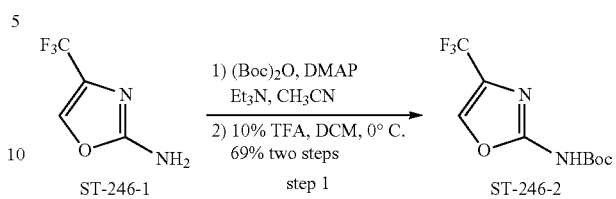

To a solution of ST-246-1, 4-(trifluoromethyl)oxazol-2-amine (1.3 g, 8.55 mmol), in 17 mL anhydrous $CH_3CN$ was added $Boc_2O$ (5.6 g, 25.7 mmol), $Et_3N$ (3.6 ml, 25.7 mmol) and DMAP (209 mg, 1.71 mmol). The solution was stirred at 40° C. for 2 hrs. When the reaction was completed, the mixture of reaction was concentrated in vacuo to remove the solvent. The resulting residue was then diluted with $H_2O$ and extracted with EtOAc. The combined organic extracts were dried with $Na_2SO_4$, concentrated to give a residue and the residue was purified by column chromatography on silica gel (PE:EtOAc=25:1) to give the intermediate as colorless wax solid (2.3 g, 77%). To a stirred solution of the intermediate (220 mg, 0.63 mmol) in DCM (6 mL) at 0° C. was added dropwise TFA (600 μL). The reaction mixture was stirred at 0° C. for 1 h and sat. $NaHCO_3$ was added to basify the solution. The organic layer was separated, and the aqueous phase was further extracted with DCM. The combined organic extracts were dried with $Na_2SO_4$, concentrated and purified by column chromatography on silica gel (PE:EtOAc=25:1 to 5:1) to give tert-butyl 4-(trifluoromethyl)oxazol-2-ylcarbamate (ST-246-2) as white solid (142 mg, 90%).

Step 2. Synthesis of ST-246-3 [tert-butyl 3-bromobenzyl(4-(trifluoromethyl)oxazol-2-yl)carbamate]

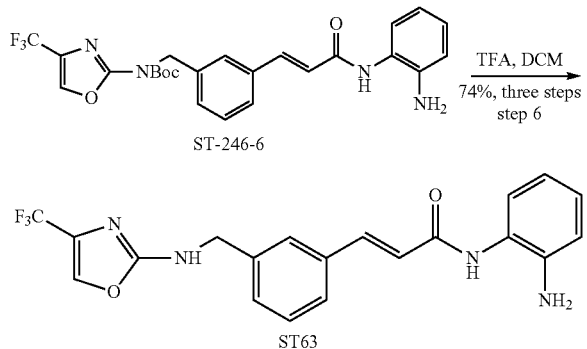

Step 0. Synthesis of ST-246-1 [4-(trifluoromethyl)oxazol-2-amine]

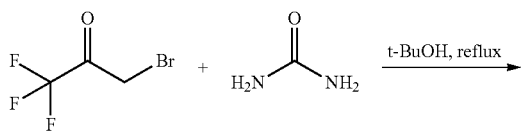

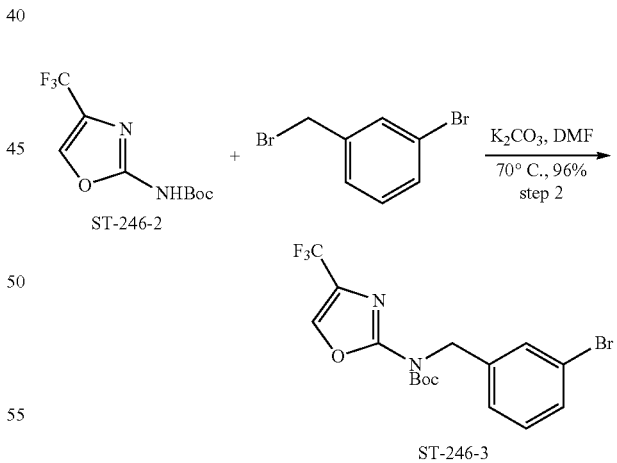

To a solution of 3-bromo-1, 1, 1-trifluoroacetone (2.19 g, 11.53 mmol) in 25 mL t-BuOH was added urea (2.77 g, 46.1 mmol). The solution was refluxed for 7 hours. Then the mixture of reaction was cooled to room temperature, concentrated in vacuo to remove the solvent. The white solid obtained was dissolved in DCM and to the mixture was added sat. $NaHCO_3$ to adjust pH value to 8.0. The water layer was extracted with DCM for three times. The organic layer was combined, washed with brine, dried over $Na_2SO_4$, concentrated and purified by column chromatography on silica gel (PE:EtOAc=3:1) to give ST-246-1 [4-(trifluoromethyl)oxazol-2-amine] as white wax solid (1.1 g, 63%).

To a mixture of ST-246-2, tert-butyl 4-(trifluoromethyl)oxazol-2-ylcarbamate (1.5 g, 5.95 mmol), and potassium carbonate (986 mg, 7.14 mmol) in DMF (30 mL) was added 3-bromobenzyl bromide (1.79 g, 7.14 mmol). The mixture was heated at 70° C. for 2.5 hrs, then quenched with saturated aqueous $NH_4Cl$ and diluted with EtOAc. The organic layer was separated, and the aqueous phase was further extracted twice with EtOAc. The combined organic phases were washed three times with water, dried over Na$_2$SO$_4$ and concentrated to give a residue, which was purification by column chromatography on silica gel (PE:EtOAc=25:1) afforded tert-butyl 3-bromobenzyl(4-(trifluoromethyl)oxazol-2-yl)carbamate (ST-246-3) as white solid (2.39 g, 96%).

Step 3. Synthesis of ST-246-4 [(E)-ethyl 3-(3-((tert-butoxycarbonyl(4-(trifluoromethyl)oxazol-2-yl)amino)methyl)phenyl)acrylate]

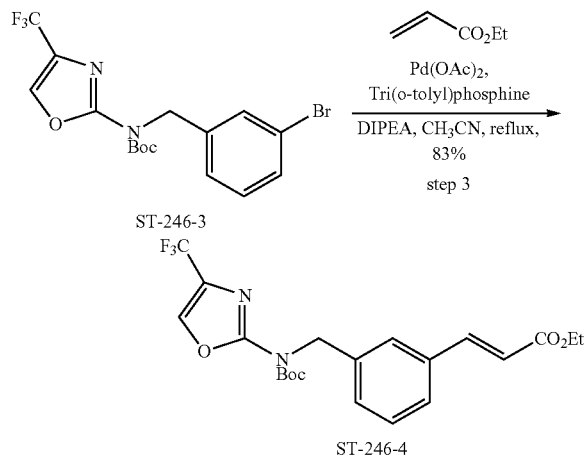

To a solution of ST-246-3, tert-butyl 3-bromobenzyl(4-(trifluoromethyl)oxazol-2-yl) carbamate (160 mg, 0.38 mmol), in anhydrous CH$_3$CN (3 mL) was added ethyl acrylate (203 μL, 1.9 mmol), Tri(o-tolyl)phosphine (46.2 mg, 0.152 mmol) and DIPEA (199 μL, 1.14 mmol). The mixture of reaction was degassed for three times. Pd(OAc)$_2$ (17 mg, 0.076 mmol) was added to the reaction, and the resulting reaction mixture was refluxed for 17 h under nitrogen atmosphere. After cooled to RT, the solvent was removed. The residue was dissolved in EtOAc and sat. NH$_4$Cl was added. The aqueous phase was extracted twice with EtOAc. The combined organic phases were washed with brine, dried over Na$_2$SO$_4$ and concentrated to give a residue, which was purification by column chromatography on silica gel (PE:EtOAc:NH$_3$=10:1:0.01) afforded (E)-ethyl-3-(3-((tert-butoxycarbonyl(4-(trifluoromethyl)oxazol-2-yl)amino)methyl)phenyl)acrylate (ST-246-4) as light yellow oil (139 mg, 83%).

Step 4. Synthesis of ST-246-5 [(E)-3-(3-((tert-butoxycarbonyl(4-(trifluoromethyl)oxazol-2-yl)amino)methyl)phenyl)acrylic acid]

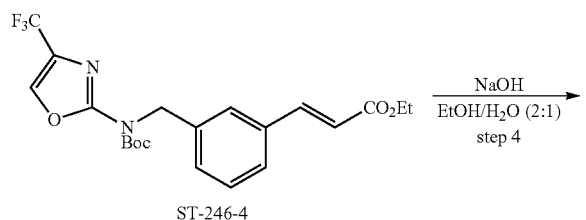

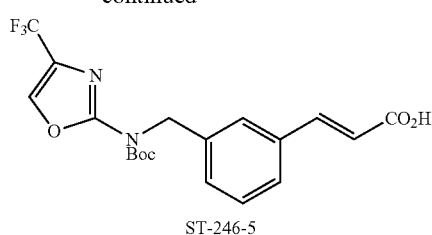

To a solution of ST-246-4, (E)-ethyl 3-(3-((tert-butoxycarbonyl(4-(trifluoromethyl)oxazol-2-yl)amino)methyl)phenyl)acrylate (130 mg, 0.38 mmol), in a solvent mixture of anhydrous ethanol (2 mL) and water (1 mL) was added NaOH (46 mg, 1.15 mmol). The solution was stirred at r.t. for 1.5 hrs. When the reaction was completed, the solution was concentrated under reduced pressure and diluted with water (10 mL). The mixture was acidified to pH=5 with 2 N HCl and extracted twice with EtOAc. The organic layer was combined, washed with brine, dried over Na$_2$SO$_4$ and concentrated to give (E)-3-(3-((tert-butoxycarbonyl(4-(trifluoromethyl)oxazol-2-yl)amino)methyl)phenyl)-acrylic acid (ST-246-5) as yellow oil without further purification (120 mg, 99%).

Step 5. Synthesis of ST-246-6 [(E)-tert-butyl 3-(3-(2-aminophenylamino)-3-oxoprop-1-enyl)benzyl(4-(trifluoromethyl)oxazol-2-yl)carbamate]

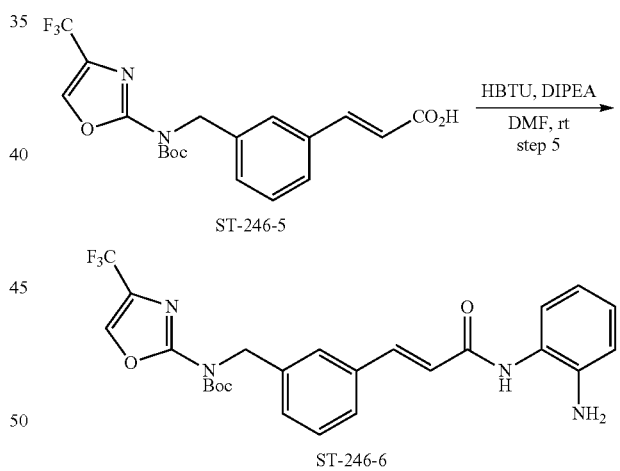

To a solution of ST-246-5, (E)-3-(3-((tert-butoxycarbonyl (4-(trifluoromethyl)oxazol-2-yl) amino)methyl)phenyl) acrylic acid (120 mg, 0.29 mmol), in 2 mL DMF were added HBTU (144 mg, 0.38 mmol) and DIPEA (76 μL, 0.44 mmol). The reaction mixture was stirred for 0.5 h. Then 1,2-diaminobenzene (41 mg, 0.38 mmol) was added. The reaction was stirred for further 2 hrs and to the mixture was added sat. NaHCO$_3$. The mixture was extracted twice with EtOAc. The organic layer was combined, washed with brine tree times, dried over Na$_2$SO$_4$, and concentrated to give (E)-tert-butyl 3-(3-(2-aminophenylamino)-3-oxoprop-1-enyl)benzyl(4-(trifluoromethyl)oxazol-2-yl)carbamate (ST-246-6), which was deprotected without further purification.

Step 6. Synthesis of ST63 [(E)-N-(2-aminophenyl)-3-(3-((4-(trifluoromethyl)oxazol-2-ylamino)methyl)phenyl)acrylamide]

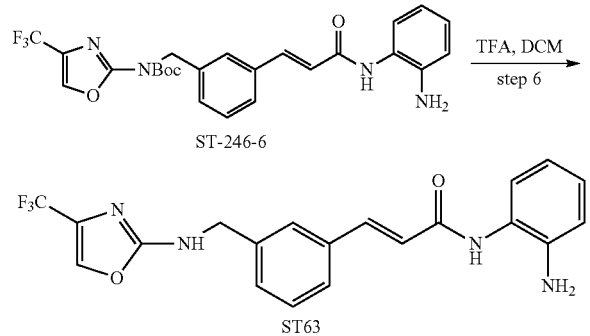

To a stirred solution of ST-246-6, (E)-tert-butyl 3-(3-(2-aminophenylamino)-3-oxoprop-1-enyl)benzyl(4-(trifluoromethyl)oxazol-2-yl)carbamate, in DCM (3 mL) at 0° C. was added TFA (900 μL) dropwise. The reaction mixture was stirred at 0° C. for 0.5 h, then warmed to r.t. for 0.5 h. Sat. NaHCO$_3$ was added to basify the solution. The organic layer was separated, and the aqueous phase was further extracted with DCM. The combined organic extracts were washed with brine and dried with Na$_2$SO$_4$, concentrated and purified by column chromatography on silica gel (PE:EtOAc=1:1) to afford preliminarily purified product. The product was solved in DCM, and then poured into cold n-hexane. White precipitate was formed, filtering and washing with n-hexane to give (E)-N-(2-aminophenyl)-3-(3-((4-(trifluoromethyl)oxazol-2-ylamino)methyl)phenyl) acrylamide (ST63) as white solid (88 mg, 75%, two steps).

$^1$H NMR (400 MHz, CDCl$_3$) δ 7.72 (d, J=12.0 Hz, 1H), 7.53 (s, 1H), 7.45-7.48 (m, 2H), 7.30-7.37 (m, 3H), 7.08 (s, 1H), 6.83 (s, 1H), 6.82 (s, 1H), 6.61 (d, J=12.0 Hz, 1H), 5.34 (s, 1H), 4.55 (s, 2H), 3.93 (brs, 2H). LCMS (ESI) m/z calcd for C$_{20}$H$_{18}$F$_3$N$_4$O$_2$ (M+H)$^+$ 403; found 403. HPLC (254 nm, 96.0%).

Example 5

Synthesis of ST66

Step 1. The Synthesis of 3-bromobenzoyl chloride (ST-232-2)

The mixture solution of ST-232-1 (1.5 g, 7.50 mmol) in SOCl$_2$ (15 mL) was stirred at 85° C. for 2 hours. The solution was concentrated under vacuum. The product ST-232-2 was obtained as a yellow oil (1.5 g, crude).

Step 2. The synthesis of 3-bromo-N-(4-methylthiazol-2-yl)benzamide (ST-232-3)

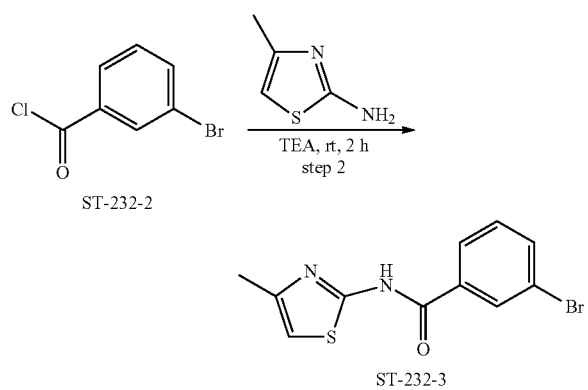

To a solution of 4-methylthiazol-2-amine (863 mg, 7.57 mmol) in DCM (20 mL) was added dropwise TEA (2.09 g, 20.64 mmol) and ST-232-2 (1.5 g, 6.88 mmol), the mixture solution was stirred at room temperature for 2 hours. The reaction was diluted with DCM (20 mL), washed with sodium carbonate (aq.) (20 mL×3). The extract was dried and concentrated under vacuum. The residue was applied on a silica gel column and eluted with EA:PE (1/5 to 1/2). The product ST-232-3 was obtained as a yellow solid (1.57 g, Yield: 77%).

Step 3. The synthesis of (E)-ethyl 3-(3-((4-(((dimethylamino)methyl)phenylamino)methyl)-phenyl)acrylate (ST-232-4)

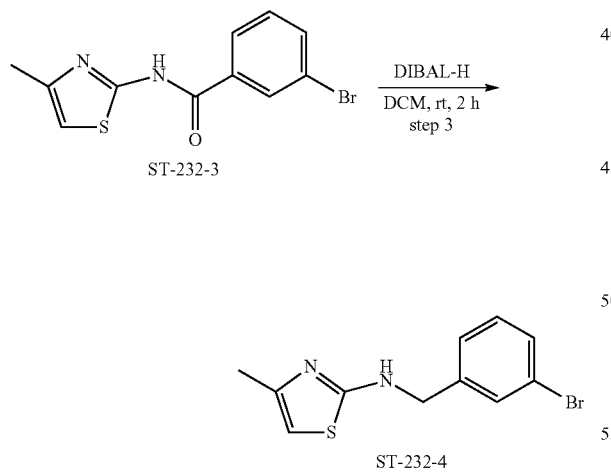

To a solution of ST-232-3 (1.4 g, 4.73 mmol) in DCM (20 mL) was added dropwise DIBAL-H (28.4 mL, 28.38 mmol, 1 mol/L in THF) at 0° C., the mixture solution was stirred at 0° C. for 2 hours. The reaction was then quenched by the addition of 10 mL of NH₄Cl (aq.), and extracted with DCM (20 mL×3). The solid was filtered out. The filtrate was concentrated and purified by flash column chromatography (EA:PE=0 to 50%). The product ST-232-4 was obtained as a yellow solid (840 mg, 2.98 mmol, Yield: 63%).

Step 4. The synthesis of (E)-ethyl 3-(3-((4-methylthiazol-2-ylamino)methyl)phenyl)acrylate (ST-232-5)

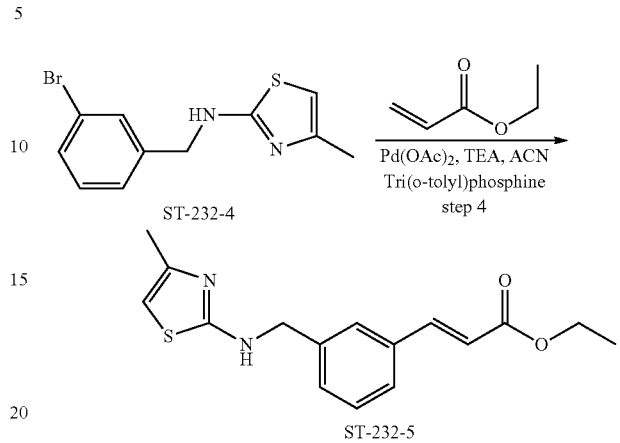

To a solution of ST-232-4 (740 mg, 2.62 mmol) in ACN (10 mL) was added sequentially palladium acetate (59 mg, 0.26 mmol), tris(2-methylphenyl)phosphine (160 mg, 0.52 mmol), triethylamine (795 mg, 7.87 mmol) and ethyl acrylate (787 mg, 7.87 mmol), the mixture solution was stirred at 85° C. overnight, LC-MS showed completion of the reaction. The reaction was diluted with EA (20 mL), washed with sodium carbonate (aq.) (30 mL×3), dried and concentrated under vacuum. The residue was purified by flash column chromatography (EA:PE=0 to 40%). The product ST-232-5 was obtained as a yellow solid (580 mg, 1.92 mmol, Yield: 73%).

Step 5. The synthesis of (E)-3-(3-((4-methylthiazol-2-ylamino)methyl)phenyl)acrylic acid (ST-232-6)

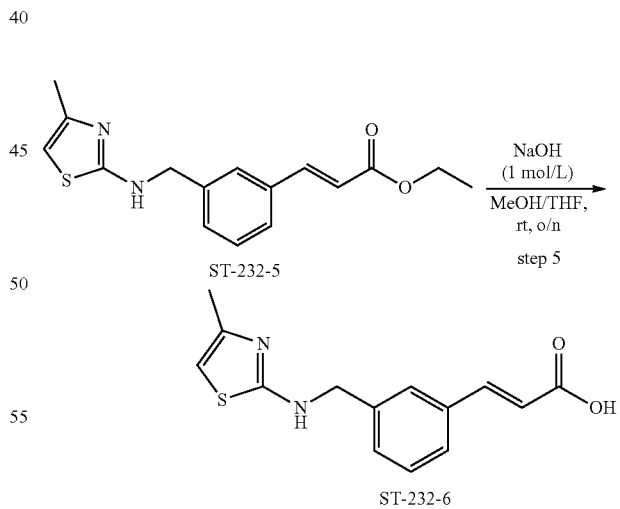

To a solution of ST-232-5 (580 mg, 1.92 mmol) in MeOH/THF (12 mL, 5:1) was added sodium hydroxide (10 mL, 1 mol/L), the mixture solution was stirred at room temperature overnight, LC-MS showed completion of the reaction. The organic phase was removed, and the residue was re-dissolved in water (10 mL). The aqueous solution was acidified with 1M HCl until no more solid formed. The suspension solution was filtered and dried. The desired product ST-232-6 was isolated as a yellow solid (500 mg, crude).

Step 6. The synthesis of ST66 [(E)-N-(2-aminophenyl)-3-(3-((4-methylthiazol-2-ylamino)methyl)phenyl)acrylamide]

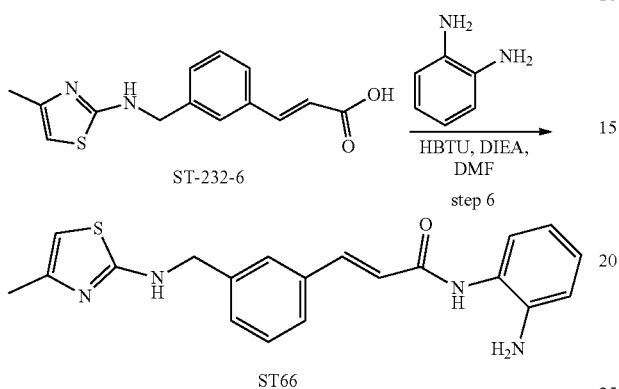

To a solution of ST-232-6 (200 mg, 0.73 mmol) in DMF (5 mL) was added HBTU (415 mg, 1.09 mmol), DIEA (287 mg, 2.19 mmol), and benzene-1,2-diamine (236 mg, 2.19 mmol). The mixture was stirred at room temperature for 2 hours. The reaction was diluted with 15 mL of brine. The suspension solution was filtered; the crude product was recrystallized from MeOH/water in the ratio of 1:5. The product ST66 was isolated as a yellow solid (240 mg, 0.66 mmol, Yield: 90%).

Purity: 97% (LC-MS, 254 nm)

$^{1}$H NMR (400 MHz, DMSO-$d_6$) δ 2.09 (s, 3H), 4.45 (d, J=5.7 Hz, 2H), 4.95 (s, 2H), 6.17 (s, 1H), 6.57 (t, J=7.6 Hz, 1H), 6.75 (d, J=7.9 Hz, 1H), 6.88-6.92 (m, 2H), 7.36-7.41 (m, 3H), 7.51-7.59 (m, 3H), 7.96 (t, J=5.7 Hz, 1H), 9.40 (s, 1H). LC-MS: m/z=365.2 ([M+H]$^{+}$).

Example 6

Synthesis of ST92

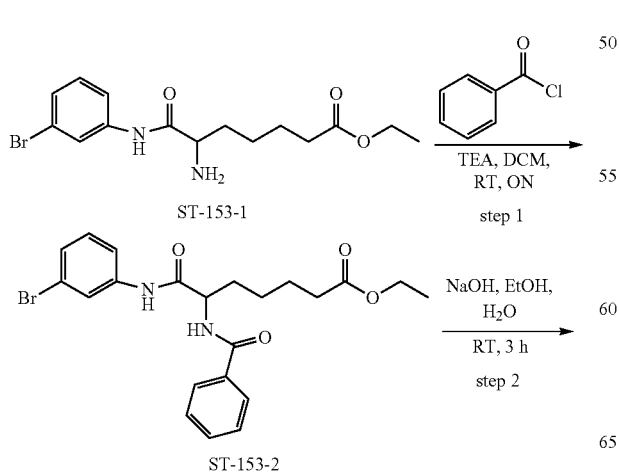

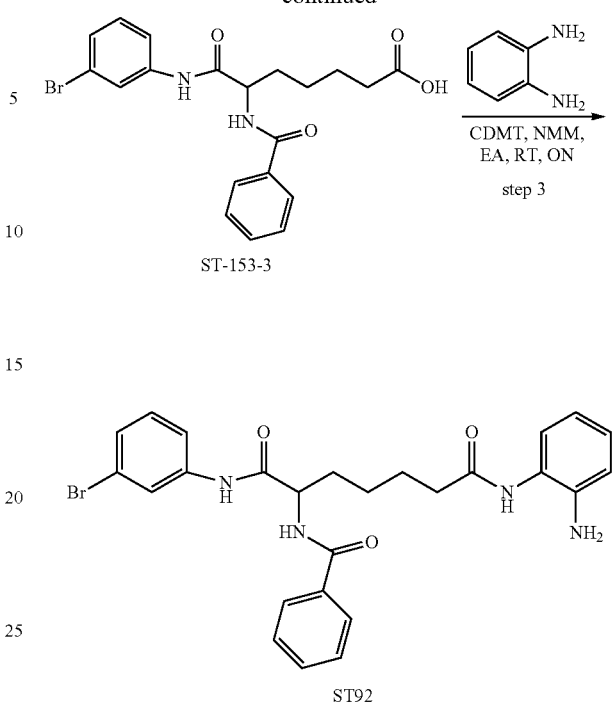

Step 1. Synthesis of ethyl 6-(3-bromophenylcarbamoyl)-6-(benzamido)hexanoate (ST-153-2)

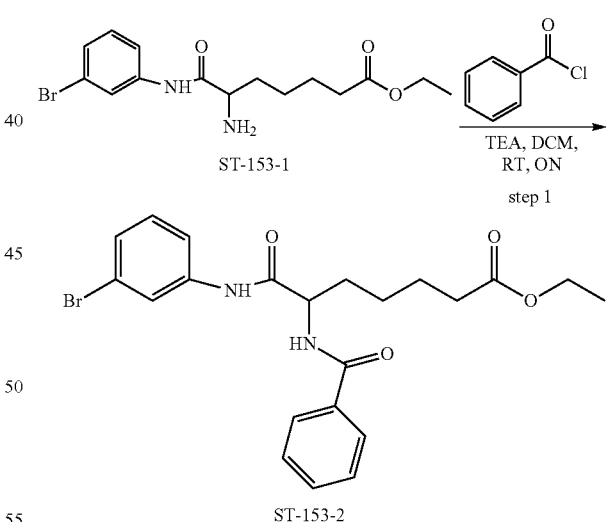

To a solution of ST-153-1 (0.200 g, 0.560 mmol) in 8 mL DCM was added benzoyl chloride (0.087 g, 0.616 mmol) and TEA (0.170 mL, 1.680 mmol). The solution was stirred at RT overnight. LC-MS showed the reaction was completed. The solution was quenched with 20 mL water and extracted with DCM. The organic layer was combined, dried over Na$_2$SO$_4$, concentrated and purified by column chromatography on silica gel to give the ST-153-2 as a yellow solid (0.235 g, yield: 91.0%).

Step 2. Synthesis of 6-(3-bromophenylcarbamoyl)-6-(benzamido)hexanoic acid (ST-153-3)

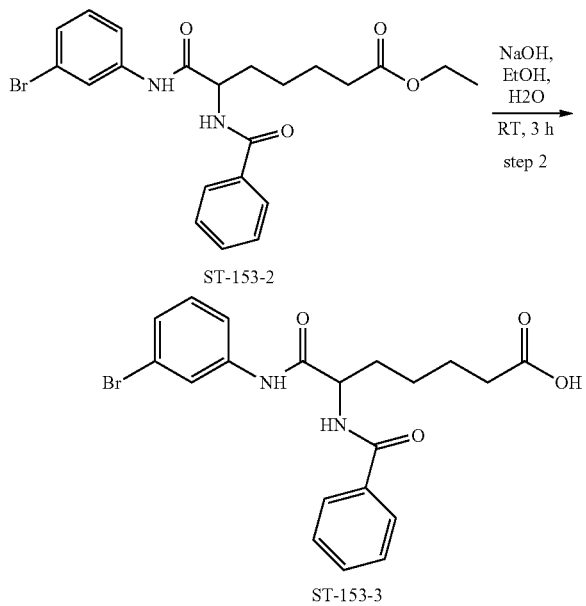

To a solution of ST-153-2 (0.235 g, 0.509 mmol) in 5 mL EtOH and 5 mL water was added NaOH (0.102 g, 2.547 mmol). The mixture was stirred at RT 3 hours. LC-MS showed that the reaction was completed. The solution was adjust pH=6 by 3N HCl. The mixture was concentrated and 10 mL water was added. Then the mixture was extracted with EA. The organic layer was combined, dried over Na$_2$SO$_4$, concentrated to give the ST-153-3 as a pale yellow solid (0.200 g, yield: 90.5%).

Step 3. Synthesis of N$^7$-(2-aminophenyl)-2-benzamido-N$^1$-(3-bromophenyl)heptanediamide (ST92)

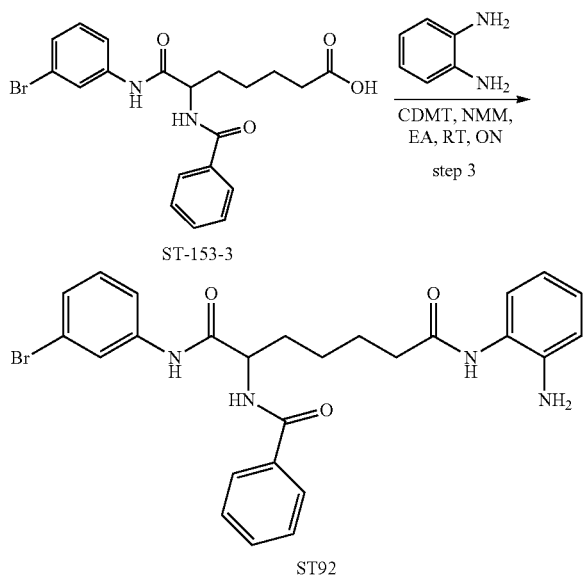

To a solution of ST-153-3 (0.200 g, 0.462 mmol) in 10 mL EA was added CDMT (0.090 g, 0.510 mmol) and benzene-1,2-diamine (0.150 mL, 1.386 mmol). Then NMM (0.070 g, 0.693 mmol) was added. The solution was stirred at RT overnight. LC-MS showed that the reaction was completed. The solution was quenched with 20 mL water and extracted with EA. The organic layer was combined, dried over Na$_2$SO$_4$, concentrated and purified by column chromatography on silica gel to give the product ST92 as a pale yellow solid (0.133 g, yield: 55.1%).

Purity: 94.9% (LC-MS, 254 nm)

1H NMR (400 MHz, DMSO-d$_6$): δ 1.58-1.34 (m, 2H), 1.66 (m, 2H), 1.94-1.77 (m, 2H), 2.33 (t, J=7.3 Hz, 2H), 4.55 (dd, J=14.6, 7.3 Hz, 1H), 4.82 (s, 2H), 6.51 (t, J=7.2 Hz, 1H), 6.70 (d, J=7.9 Hz, 1H), 6.88 (t, J=7.1 Hz, 1H), 7.12 (d, J=7.6 Hz, 1H), 7.34-7.20 (m, 2H), 7.47 (t, J=7.4 Hz, 2H), 7.54 (d, J=7.5 Hz, 2H), 7.92 (d, J=7.3 Hz, 2H), 7.99 (s, 1H), 8.63 (d, J=7.4 Hz, 1H), 9.08 (s, 1H), 10.32 (s, 1H).

LC-MS: m/z=525.1730 ([M+H]$^+$).

Example 7

Synthesis of ST94

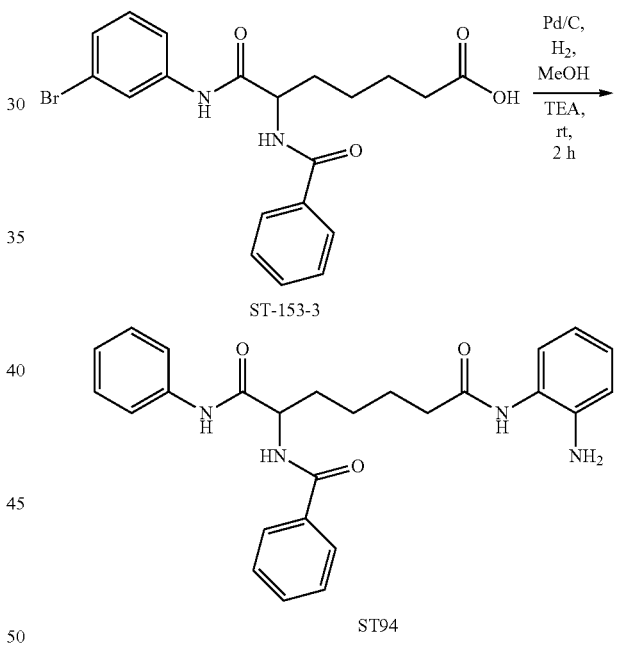

To a solution of ST-153-3 (0.050 g, 0.956 mmol) in MeOH (5 mL) were added Pd/C (5 mg) and TEA (2 mL, 1.434 mmol) at RT. The mixture was stirred under H$_2$ at RT for 2 hours. LC-MS showed that the reaction was completed. The solution was filtered and concentrated, then H$_2$O (20 mL) was added. The solution was extracted with EtOAc, and the organic layer was combined, dried over Na$_2$SO$_4$, concentrated to give the ST94 as a pale yellow solid (33 mg, yield: 78.5%).

Purity: 94.6% (LC-MS, 254 nm)

$^1$H NMR: (400 MHz, d$_6$-DMSO): δ 1.45-1.51 (m, 2H), 1.66-1.68 (m, 2H), 1.85-1.87 (m, 2H), 2.34 (t, J=7.3 Hz, 2H), 4.60 (d, J=14.6, 7.3 Hz, 1H), 4.81 (s, 2H), 6.51 (t, J=7.2 Hz, 1H), 6.71 (d, J=7.9 Hz, 1H), 6.88 (t, J=7.1 Hz, 1H), 7.05 (t, J=8.0 Hz, 1H), 7.12 (d, J=8.0 Hz, 1H), 7.31 (t, J=7.3 Hz, 2H), 7.47 (t, J=7.3 Hz, 2H), 7.54 (d, J=7.3 Hz, 1H), 7.63 (d,

J=7.9 Hz, 2H), 7.93 (d, J=7.2 Hz, 2H), 8.63 (d, J=8.0 Hz, 1H), 9.08 (s, 1H), 10.32 (s, 1H).

LC-MS: m/z=446.24 ([M+H]$^+$).

Example 8

Synthesis of ST85

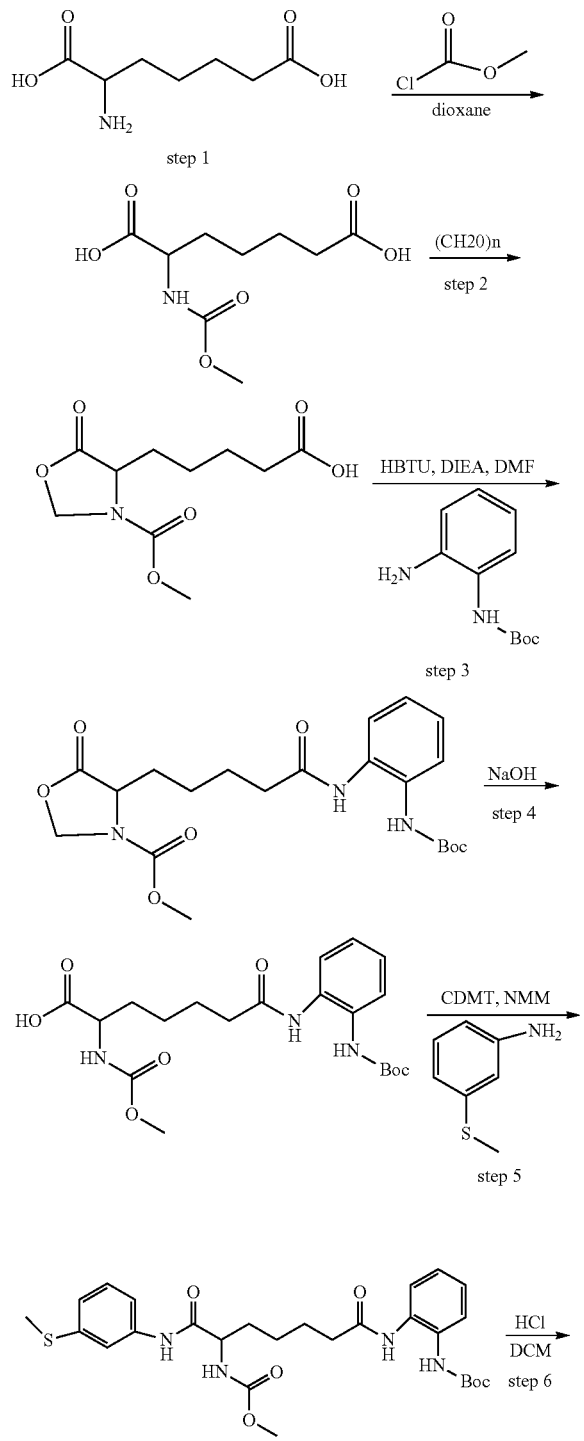

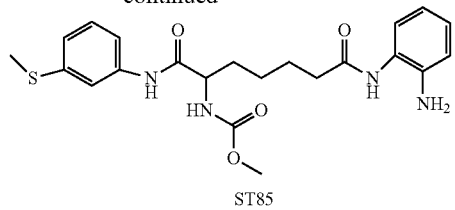

ST85

Step 1. The Preparation of 2-((methoxycarbonyl)amino)heptanedioic acid

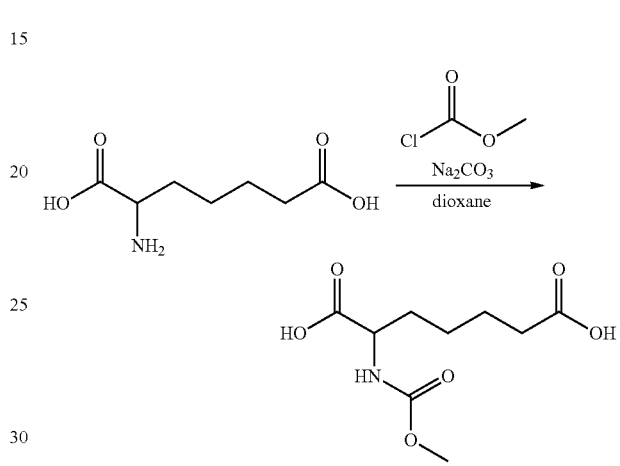

To a solution of 2-aminoheptanedioic acid (1.00 g, 5.71 mmol) in 20 mL 1,4-dioxane was added Na$_2$CO$_3$ (1.82 g, 17.13 mmol). Then the methyl carbonochloridate (809 mg, 8.57 mmol) was added dropwise at 0° C. The solution was stirred at RT overnight. When the reaction was completed, the solution was concentrated and 50 mL water was added. The solution was extracted with EA. The organic layer was combined, washed with brine, dried over Na$_2$SO$_4$. The solvent was removed by rotary evaporation and the product dried under high vacuum. The final compound was obtained in form of a colorless to slightly yellow oil (1.30 g, yield 97.6%).

Step 2. The Preparation of 5-(3-(methoxycarbonyl)-5-oxooxazolidin-4-yl)pentanoic acid

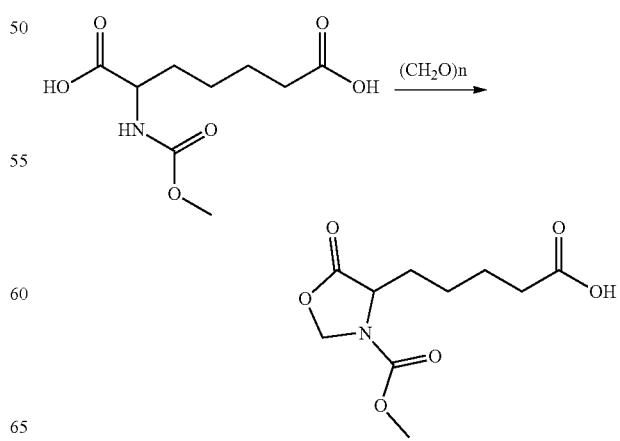

To a solution of 2-((methoxycarbonyl)amino)heptanedioic acid (1.30 g, 5.57 mmol) in 20 mL toluene was added 4-methylbenzenesulfonic acid (0.067 g, 0.389 mmol) and paraformaldehyde (0.648 g). The mixture was refluxed overnight. When the reaction was completed, the mixture was filtered and the filtrate was concentrated to give a yellow oil (1.00 g, yield 73%).

Step 3. The Preparation of methyl 4-(5-((2-((tert-butoxycarbonyl)amino)phenyl)amino)-5-oxopentyl)-5-oxooxazolidine-3-carboxylate

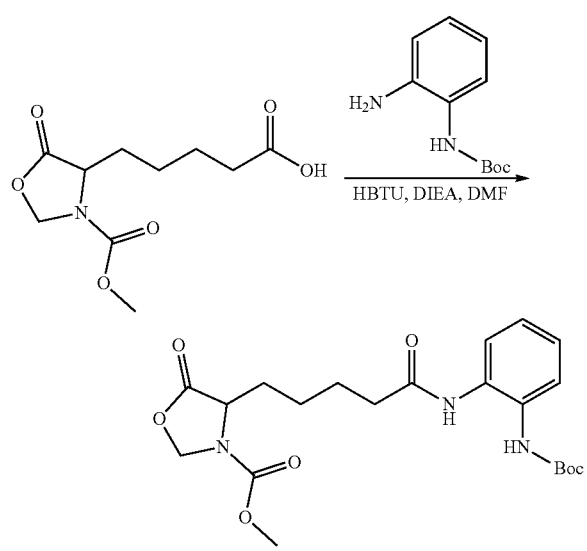

To a solution of 5-(3-(methoxycarbonyl)-5-oxooxazolidin-4-yl)pentanoic acid (1.00 g, 4.08 mmol) in DMF (10 mL) was added HBTU (2.32 g, 6.12 mmol) and DIEA (1.01 mL, 6.12 mmol). Then the tert-butyl (2-aminophenyl)carbamate (1.02 g, 4.90 mmol) was added after 0.5 h. The solution was stirred at RT overnight. When the reaction was completed, the solution was quenched with 50 mL water and extracted with EA. The organic layer was combined, washed with brine, dried with anhydrous sodium sulfate and concentrated under reduced pressure. The residue was purified by silica gel chromatography column with ethyl acetate to obtain the product as a yellow semisolid (1.00 g, yield 58.3%).

Step 4. The preparation of 7-((2-((tert-butoxycarbonyl)oxy)phenyl)amino)-2-((methoxycarbonyl)amino)-7-oxoheptanoic acid

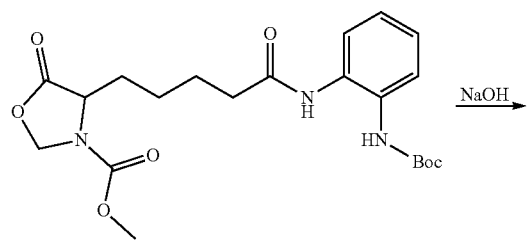

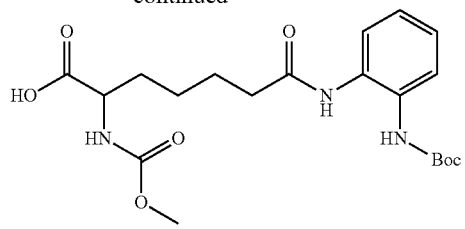

To a solution of methyl 4-(5-((2-((tert-butoxycarbonyl)amino)phenyl)amino)-5-oxopentyl)-5-oxooxazolidine-3-carboxylate (1.00 g, 2.30 mmol) in MeOH (20 mL) and $NH_3 \cdot H_2O$ (5 mL) was added NaOH (184 mg, 4.60 mmol). The solution was stirred at RT for overnight. When the reaction was completed, the solution was concentrated and added 50 mL water. The mixture was adjusted to pH=5 by HCl solution. The mixture was extracted with EA. The organic layer was combined, washed with brine, dried over $Na_2SO_4$ and concentrated to give a yellow semisolid (800 mg, yield 79%).

Step 5: The Preparation of methyl (7-((2-((tert-butoxycarbonyl)amino)phenyl)amino)-1-((3-(methylthio)phenyl)amino)-1,7-dioxoheptan-2-yl)carbamate

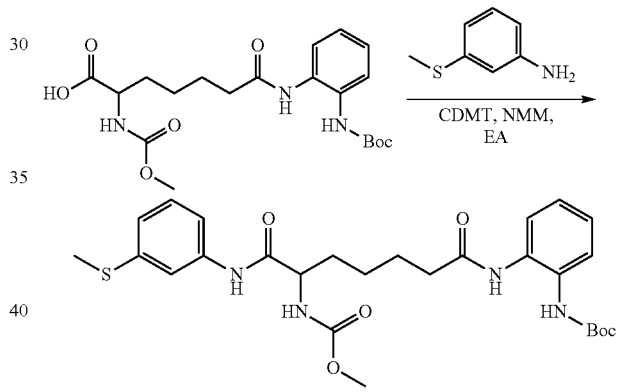

To a solution of 7-((2-((tert-butoxycarbonyl)amino)phenyl)amino)-2-((methoxycarbonyl)amino)-7-oxoheptanoic acid 100 mg, 0.236 mmol) in 5 mL EA were added CDMT (84 mg, 0.354 mmol) and 3-(methylthio)aniline (66 mg, 0.472 mmol). Then NMM (0.093 mL, 0.850 mmol) was added. The solution was stirred at RT overnight. When the reaction was completed, the solution was concentrated and purified by column chromatography on silica gel to give a yellow semisolid (80 mg, yield 62%).

Step 6. The preparation of methyl (7-((2-aminophenyl)amino)-1-((3-(methylthio)phenyl)amino)-1,7-dioxoheptan-2-yl)carbamate (ST85)

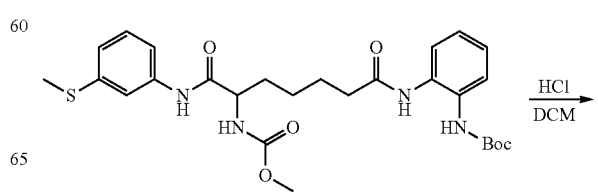

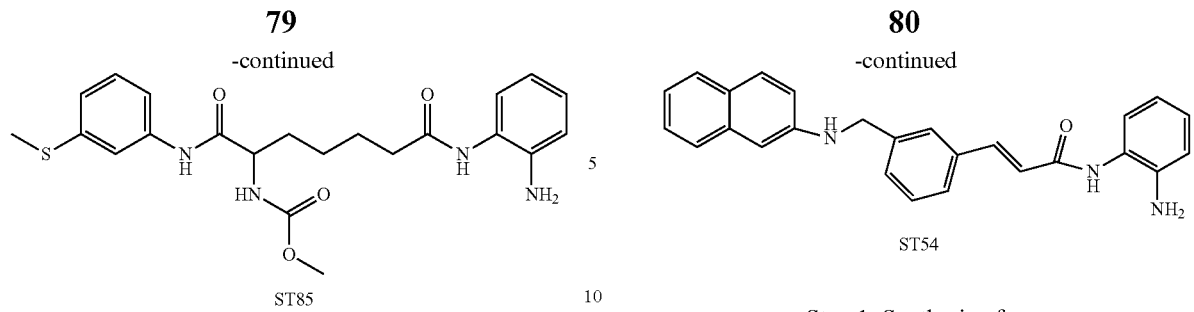

ST85

To a solution of methyl (7-((2-((tert-butoxycarbonyl)amino)phenyl)amino)-1-((3-(methylthio)phenyl)amino)-1,7-dioxoheptan-2-yl)carbamate (80 mg, 0.147 mmol) in 10 mL DCM was saturated HCl (g) for 0.5 h at 0° C. When the reaction was completed, the saturated NaHCO₃ solution was added to adjusted pH=8. The mixture was extracted with EA for three times. The organic layer was combined, dried over $Na_2SO_4$, concentrated and purified by column chromatography on silica gel to give a light yellow solid (50 mg, yield 76.6%).

$^1$H NMR (500 MHz, DMSO-$d_6$) δ 1.30-1.48 (m, 2H), 1.64 (dtd, J=32.1, 14.1, 8.1 Hz, 4H), 2.31 (t, J=7.4 Hz, 2H), 2.45 (s, 3H), 3.54 (s, 3H), 4.11 (td, J=8.6, 5.2 Hz, 1H), 4.80 (s, 2H), 6.52 (td, J=7.6, 1.4 Hz, 1H), 6.70 (dd, J=7.9, 1.4 Hz, 1H), 6.88 (td, J=7.6, 1.5 Hz, 1H), 6.94 (ddd, J=7.8, 1.9, 1.0 Hz, 1H), 7.13 (dd, J=7.9, 1.5 Hz, 1H), 7.24 (t, J=8.0 Hz, 1H), 7.31-7.38 (m, 1H), 7.44 (d, J=7.9 Hz, 1H), 7.60 (t, J=2.0 Hz, 1H), 9.06 (s, 1H), 10.05 (s, 1H).

LCMS: [M+H]⁺=445.1887

Example 9

Synthesis of ST54

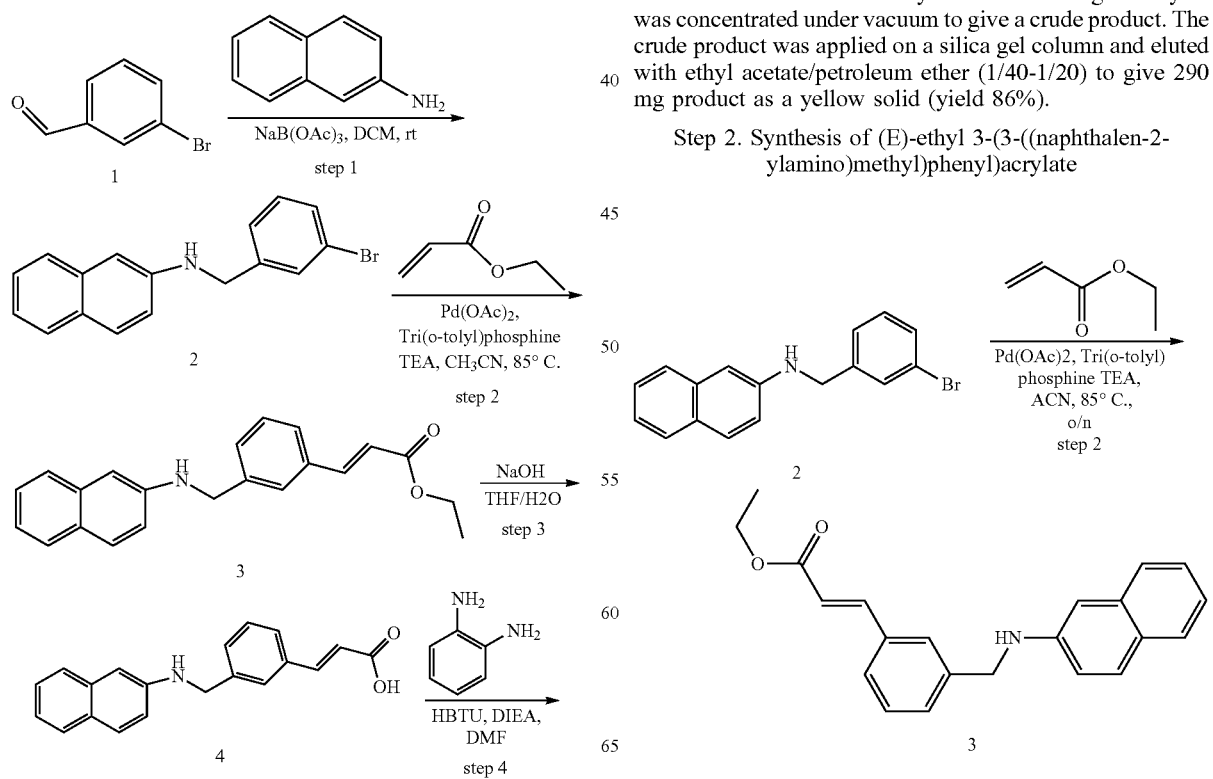

ST54

Step 1. Synthesis of N-(3-bromobenzyl)naphthalen-2-amine

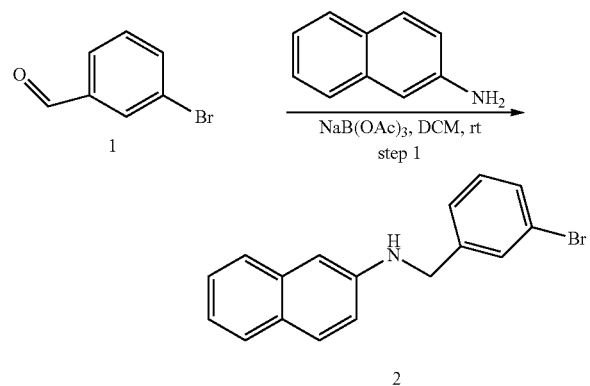

To a solution of 3-bromobenzaldehyde (200 mg, 1.09 mmol) in DCM (10 mL) was added naphthalen-2-amine (187 mg, 1.30 mmol), followed by sodium Triacetoxyborohyride (688 mg, 3.26 mmol). The mixture solution was stirred at room temperature for overnight, then diluted with water and extracted with ethyl acetate. The organic layers was concentrated under vacuum to give a crude product. The crude product was applied on a silica gel column and eluted with ethyl acetate/petroleum ether (1/40-1/20) to give 290 mg product as a yellow solid (yield 86%).

Step 2. Synthesis of (E)-ethyl 3-(3-((naphthalen-2-ylamino)methyl)phenyl)acrylate To a solution of N-(3-bromobenzyl)naphthalen-2-amine (290 mg, 0.93 mmol) in acetonitrile (5 ml) were added diacetoxypalladium (21 mg, 0.09 mmol), tris(2-methylphenyl)phosphine (57 mg, 0.19 mmol), TEA (361 mg, 2.80 mmol) and ethyl acrylate (280 mg, 2.80 mmol). The mixture was stirred at 85° C. for overnight, then cooled down to room temperature and concentrated under vacuum to give a residue. The residue was applied on a silica gel column and eluted with ethyl acetate/petroleum ether (1/50~1/10) to give 170 mg product as a yellow solid (yield 59%).

Step 3. Synthesis of (E)-3-(3-((naphthalen-2-ylamino)methyl)phenyl)acrylic acid

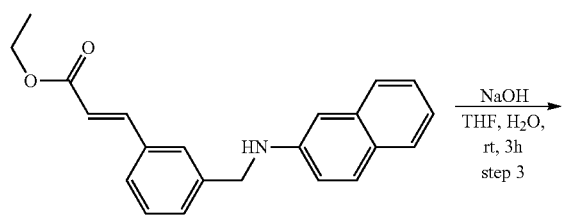

3

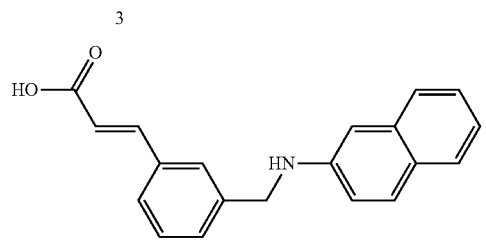

4

To a solution of (E)-ethyl 3-(3-((naphthalen-2-ylamino)methyl)phenyl)acrylate (170 mg, 0.51 mmol) in EtOH (5 mL) was added NaOH (5 mL, 1 mol/L). The mixture solution was stirred at room temperature for overnight, then diluted with water (5 mL). The mixture was concentrated under vacuum and the pH value of the solution was adjusted to 6-7 with HCl (1 mol/L). The solid formed was collected by filtration and washed with water, dried under infrared light to give 140 mg crude product as a yellow solid.

Step 4. Synthesis of (E)-N-(2-aminophenyl)-3-(3-((naphthalen-2-ylamino)methyl)phenyl) Acrylamide (ST54)

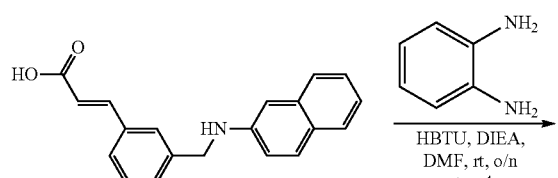

4

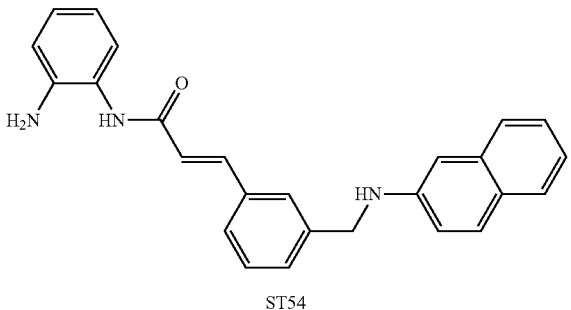

ST54

To a solution of (E)-3-(3-((naphthalen-2-ylamino)methyl)phenyl)acrylic acid (140 mg, 0.46 mmol) in DMF (5 mL) were added HBTU (263 mg, 0.69 mmol) and DIEA (179 mg, 1.39 mmol). The mixture solution was stirred at 0° C. for 20 min. To the mixture was added benzene-1,2-diamine (150 mg, 1.39 mmol) and the resulting solution was stirred at room temperature for overnight. The mixture was diluted with water (20 mL). The solid formed was collected by filtration and washed with water. The solid was collected by filtration and dried under infrared light to give 167 mg product as a white solid (yield 92%).

$^1$H NMR (400 MHz, DMSO-$d_6$): δ 4.42 (d, J=4 Hz, 2H), 4.94 (s, 2H), 6.56-6.60 (m, 2H), 6.71-6.75 (m, 2H), 6.88-6.92 (m, 2H), 7.06-7.11 (m, 2H), 7.25-7.29 (m, 1H), 7.33-7.35 (m, 1H), 7.40-7.43 (m, 1H), 7.45-7.46 (m, 1H), 7.49-7.51 (m, 2H), 7.52-7.57 (m, 1H), 7.60-7.64 (m, 2H), 7.68 (s, 1H), 9.38 (s, 1H).

LCMS found 493.1869 [M+H]$^+$, HPLC (254 nm, 94%).

Example 10

Synthesis of ST93

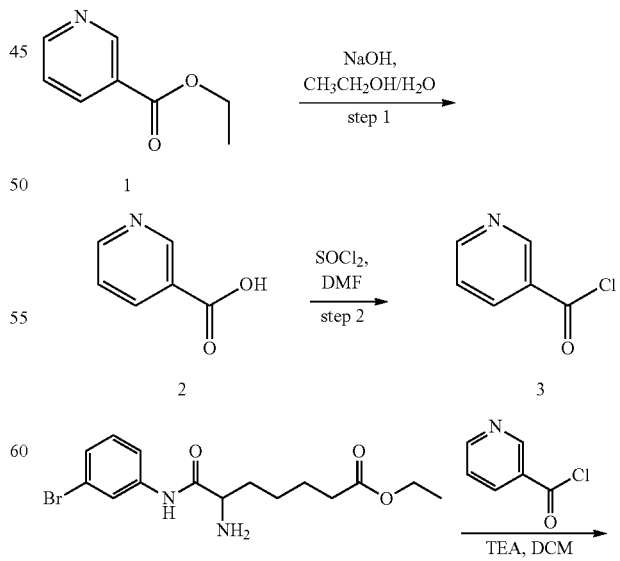

83
-continued

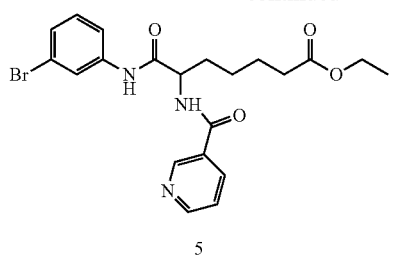
5

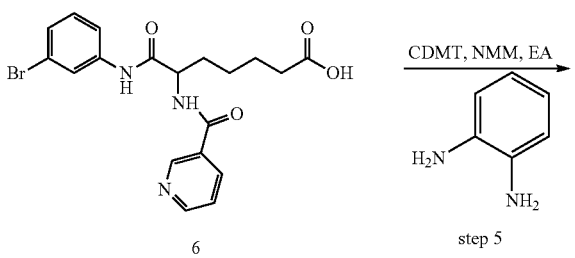
6

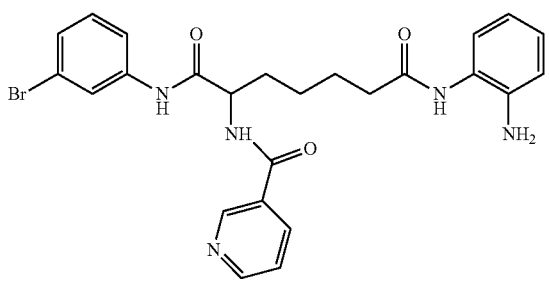
ST93

Step 1. Synthesis of Nicotinic Acid

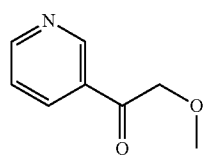
1

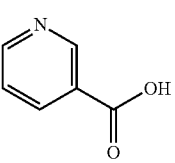
2

To a solution of ethyl nicotinate (compound 1, 5.000 g, 40.7 mmol) in 40 mL anhydrous ethanol and 5 mL water was added NaOH (3.260 g, 81.4 mmol). The solution was stirred at RT overnight. When the reaction was completed, the solution was concentrated and added 20 mL water. The mixture was adjusted to pH=5 by HCl solution. The mixture was filtered and the filter cake was dried to give the nicotinic acid 3.330 g (compound 2, yield 81.8%) without further purification.

84
Step 2. Synthesis of Nicotinoyl Chloride

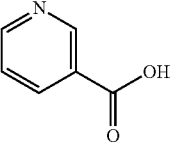
2

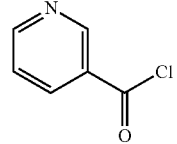
3

To a solution of nicotinic acid (compound 2, 0.200 g, 1.63 mmol) in 10 mL SOCl$_2$ was added 1-2 drop DMF. The mixture was refluxed overnight. When the reaction was completed, the solution was concentrated to give nicotinoyl chloride 0.210 g without further purification (compound 3, yield 91.6%).

Step 3. Synthesis of ethyl 7-(3-bromophenylamino)-6-(nicotinamido)-7-oxoheptanoate

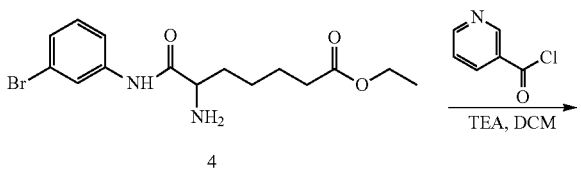
4

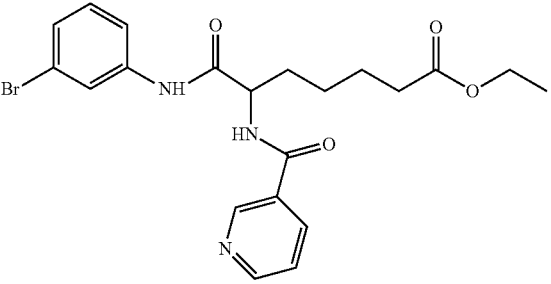
5

To a solution of ethyl 6-amino-7-(3-bromophenylamino)-7-oxoheptanoate (compound 4, 0.300 g, 0.843 mmol) in 10 mL DCM was added nicotinoyl chloride (compound 3, 0.143 g, 1.01 mmol). Then the triethylamine (0.256 g, 2.53 mmol) was added. The solution was stirred at RT overnight. When the reaction was completed, the solution was quenched with 50 mL water and extracted with DCM. The organic layer was combined, washed with brine, dried over Na$_2$SO$_4$, concentrated and purified by column chromatography on silica gel to give the crude product of ethyl 7-(3-bromophenylamino)-6-(nicotinamido)-7-oxoheptanoate 0.236 g. (compound 5, yield 60.7%).

Step 4. Synthesis of 7-(3-bromophenylamino)-6-(nicotinamido)-7-oxoheptanoic acid

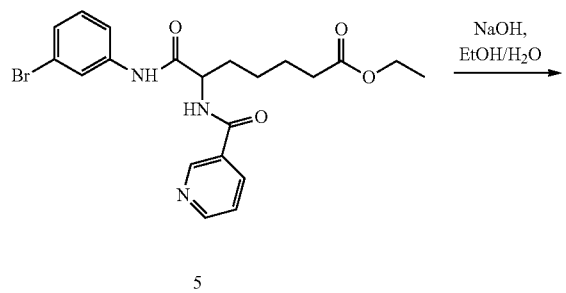

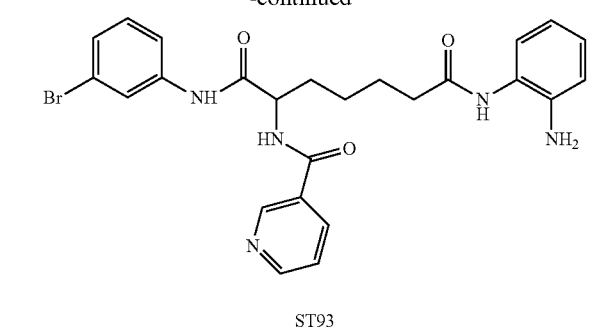

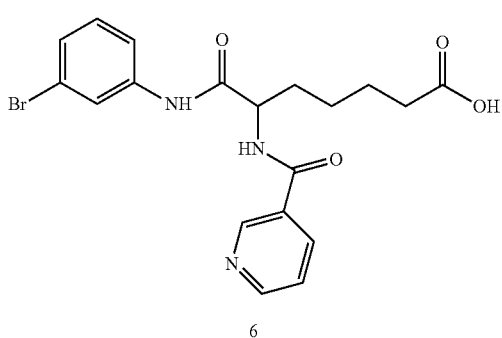

To a solution of ethyl 7-(3-bromophenylamino)-6-(nicotinamido)-7-oxoheptanoate (compound 5, 0.236 g, 0.512 mmol) in 15 mL anhydrous ethanol and 3 mL water was added NaOH (0.041 mg, 1.02 mmol). The solution was stirred at RT for 3 h. When the reaction was completed, the solution was concentrated and to the mixture was added 20 mL water. The mixture was adjusted to pH=5 by HCl solution. The mixture was extracted with EA. The organic layer was combined, washed with brine, dried over $Na_2SO_4$ and concentrated to give 7-(3-bromophenylamino)-6-(nicotinamido)-7-oxoheptanoic acid 0.174 g without further purification. (compound 6, yield 78.5%).

Step 5. Synthesis of ST93

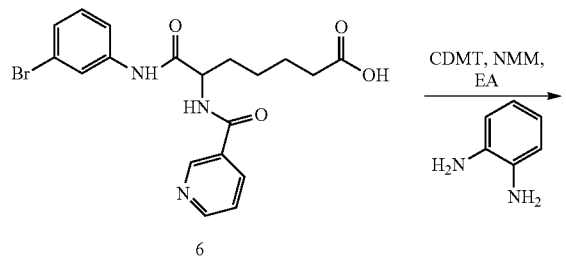

To a solution of 7-(3-bromophenylamino)-6-(nicotinamido)-7-oxoheptanoic acid (compound 6, 0.174 g, 0.402 mmol) in 20 mL EA was added CDMT (0.106 g, 0.603 mmol) and NMM (0.081 g, 0.804 mmol). Then the benzene-1,2-diamine (0.217 g, 2.01 mmol) was added after 5-10 min. When the reaction was completed, the mixture was concentrated and purified by column chromatography on silica gel to give $N^7$-(2-aminophenyl)-$N^1$-(3-bromophenyl)-2-(nicotinamido)heptanediamide 0.097 g (ST93), yield 46.2%).

$^1$H NMR (500 MHz, DMSO-$d_6$): 1.39-1.72 (m, 4H), 1.84-1.89 (m, 2H), 2.34 (t, J=9.0 Hz, 2H), 4.55-4.60 (m, 1H), 4.80 (s, 2H), 6.48 (t, J=9.5 Hz, 1H), 6.71 (d, J=11.0 Hz, 1H), 6.86-6.90 (m, 1H), 7.12 (d, J=9.5 Hz, 1H), 7.24-7.31 (m, 2H), 7.50-7.55 (m, 2H), 7.99 (s, 1H), 8.24-8.26 (m, 1H), 8.72-8.73 (m, 1H), 8.89 (d, J=9.0 Hz, 1H), 9.07 (s, 2H), 10.34 (s, 1H). LCMS found 524.1306 [M+H]$^+$, HPLC (254 nm, 99.0%).

Example 11

Synthesis of ST53

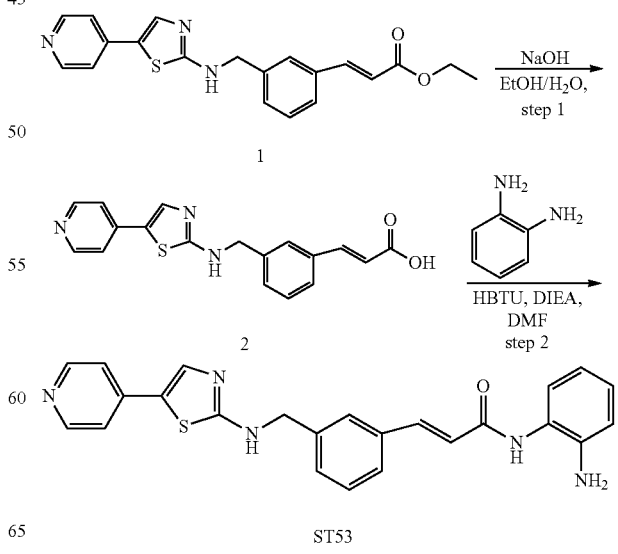

Step 1. Synthesis of (E)-3-(3-((5-(pyridin-4-yl)thiazol-2-ylamino)methyl)phenyl)acrylic acid

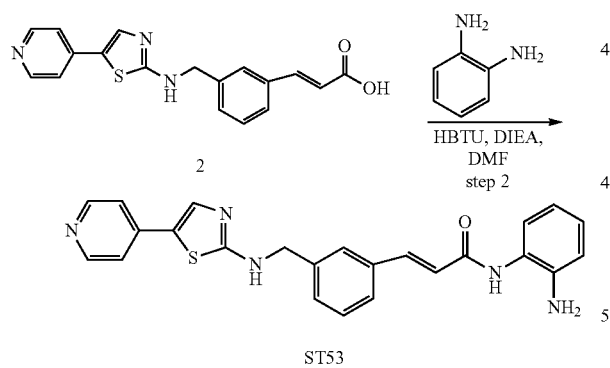

To a solution of (E)-ethyl 3-(3-((5-(pyridin-4-yl)thiazol-2-ylamino)methyl)phenyl)acrylate (250 mg, 0.68 mmol) in EtOH (5 mL) was added NaOH (5 mL, 1 mol/L). The mixture solution was stirred at room temperature for overnight. The mixture was diluted with water (5 mL) and concentrated under vacuum. The pH value of the resulting mixture was adjusted to 6-7 with HCl (1 mol/L). The resulting solid was collected by filtration and washed with water. The solid was dried under infrared light to give crude product (135 mg) as a yellow solid.

Step 2. Synthesis of (E)-N-(2-aminophenyl)-3-(3-((5-(pyridin-4-yl)thiazol-2-ylamino)methyl)phenyl)acrylamide (ST53)

To a solution of (E)-3-(3-((5-(pyridin-4-yl)thiazol-2-ylamino)methyl)phenyl)acrylic acid (135 mg, 0.40 mmol) in DMF (5 mL) were added HBTU (228 mg, 0.60 mmol) and DIEA (155 mg, 1.20 mmol). The mixture solution was stirred at 0° C. for 20 min. To the mixture was added benzene-1,2-diamine (130 mg, 1.20 mmol) and stirred at room temperature for overnight. The residue was diluted with water (20 mL). The solid was collected by filtration and washed with water. The crude product was re-crystallized from MeOH/H$_2$O in the ratio of 1:5 to give 140 mg product as a white solid (yield 82%).

$^1$H NMR (400 MHz, DMSO-d$_6$): δ 4.56 (d, J=4 Hz, 2H), 4.96 (s, 2H), 6.60-6.56 (m, 1H), 6.74-6.76 (m, 1H), 6.87-6.94 (m, 2H), 7.35-7.36 (m, 1H), 7.41-7.47 (m, 3H), 7.51-7.53 (m, 1H), 7.54-7.57 (m, 1H), 7.67 (s, 1H), 7.73-7.77 (m, 2H), 8.34-8.37 (m, 1H), 8.54-8.56 (m, 2H), 9.40 (s, 1H).

LCMS found 428.1645 [M+H]$^+$, HPLC (254 nm, 97%).

Example 12

Synthesis of ST49

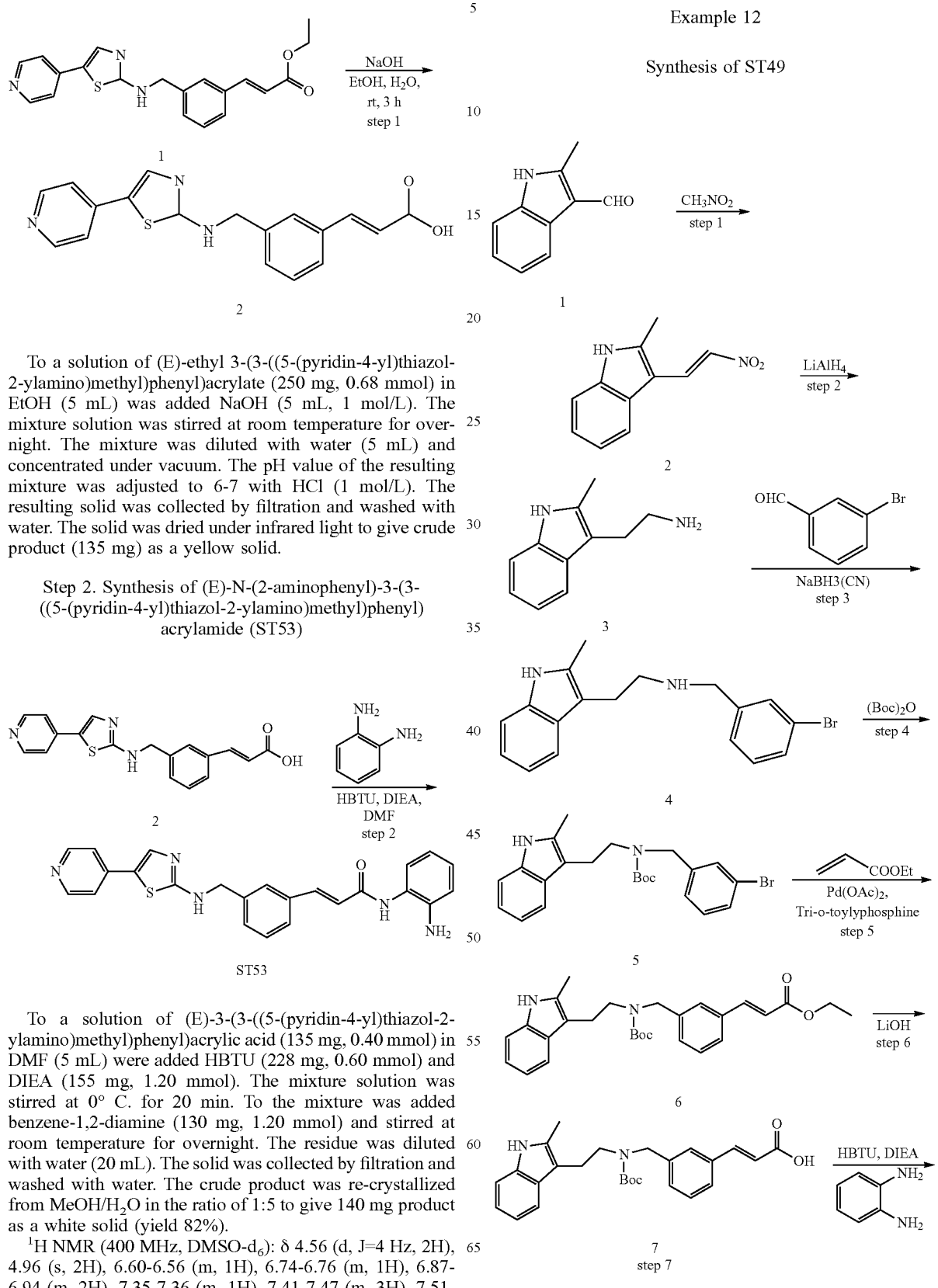

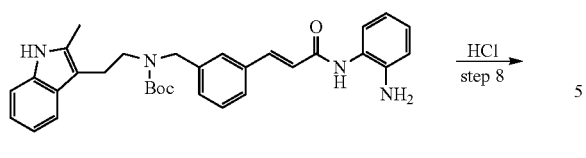

8

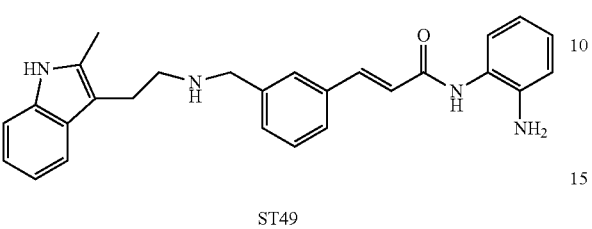

ST49

Step 1. Synthesis of (E)-2-methyl-3-(2-nitrovinyl)-1H-indole

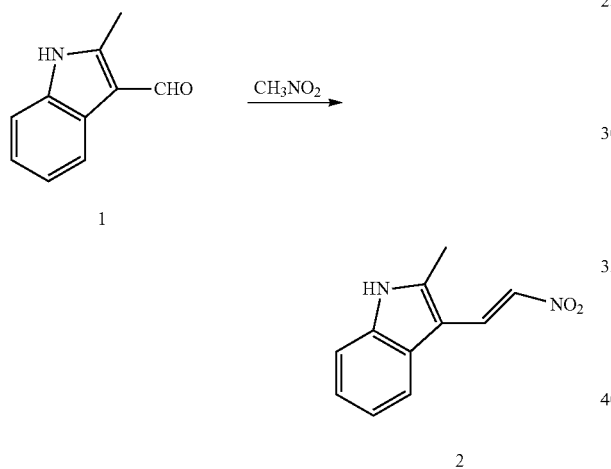

The mixture of 2-methyl-1H-indole-3-carbaldehyde (compound 1, 2.500 g, 15.704 mmol) and NH$_4$OAc (1.800 g, 23.346 mmol) in 5 mL MeNO$_2$ was heated at 100° C. for 3 h. When the reaction was completed, the mixture was concentrated and purified by column chromatography on silica gel to give the (E)-2-methyl-3-(2-nitrovinyl)-1H-indole 2.540 g (compound 2, yield 80.1%).

Step 2. Synthesis of 2-(2-methyl-1H-indol-3-yl)ethanamine

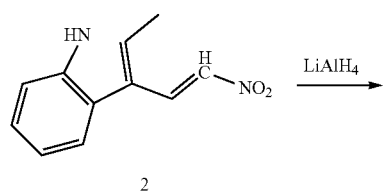

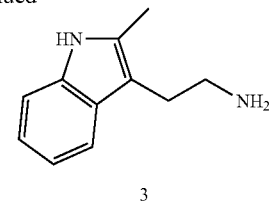

3

To a mixture of LiAlH$_4$ (0.483 g, 12.700 mmol) in 50 mL THF was added a solution of (E)-2-methyl-3-(2-nitrovinyl)-1H-indole (compound 2, 2.540 g, 12.562 mmol) in THF dropwise at 0° C. Then the mixture was stirred at RT overnight. When the reaction was completed, 10.000 g Na$_2$SO$_4$ was added. The reaction was quenched by water at 0° C. The mixture was filtered and filtrate was washed with brine and concentrated give 2-(2-methyl-1H-indol-3-yl)ethanamine 2.095 g without further purification (compound 3, yield 95.4%).

Step 3. Synthesis of N-(3-bromobenzyl)-2-(2-methyl-1H-indol-3-yl)ethanamine

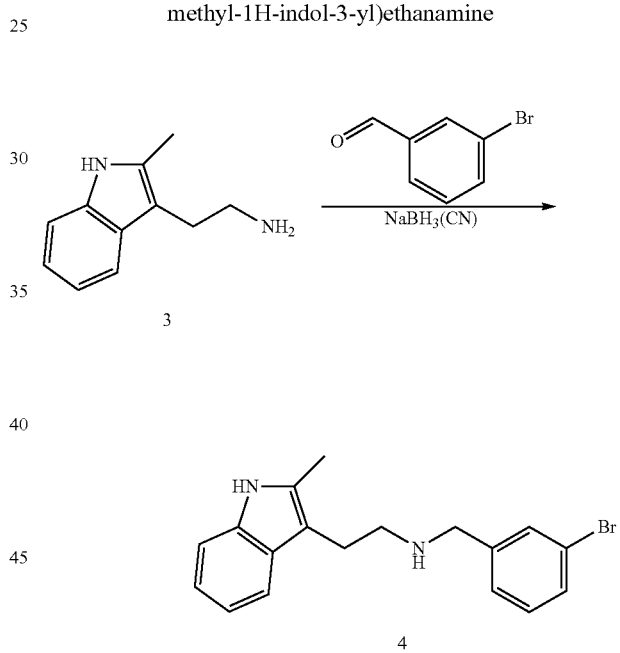

To a solution of 2-(2-methyl-1H-indol-3-yl)ethanamine (compound 3, 1.000 g, 5.741 mmol) in 20 mL CH$_2$Cl$_2$ was added 3-bromobenzaldehyde (1.280 g, 6.919 mmol). Then two drops of AcOH was added to. After 0.5 h, NaBH$_3$CN (1.800 g, 12.739 mmol) was added. The mixture was stirred at RT overnight. When the reaction was completed, the reaction mixture was quenched by sat. NaHCO$_3$ and extracted with EA. The organic layer was combined, washed with brine and concentrated and purified by column chromatography on silica gel to give N-(3-bromobenzyl)-2-(2-methyl-1H-indol-3-yl)ethanamine 0.833 g (compound 4, yield 42.3%).

Step 4. Synthesis of tert-butyl 3-bromobenzyl(2-(2-methyl-1H-indol-3-yl)ethyl)carbamate

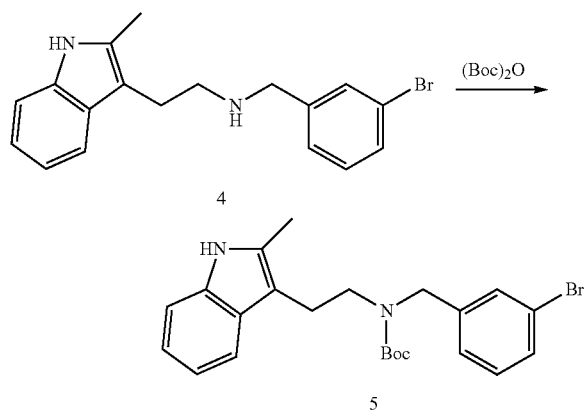

To a solution of N-(3-bromobenzyl)-2-(2-methyl-1H-indol-3-yl)ethanamine (compound 4, 1.590 g, 4.362 mmol) in 50 mL THF was added triethylamine (4.0 mL, 28.775 mmol) and Boc$_2$O (1.6 mL, 6.963 mmol) at 0° C. The solution was stirred at RT overnight. When the reaction was completed, the solution was concentrated and purified by column chromatography on silica gel to give tert-butyl 3-bromobenzyl (2-(2-methyl-1H-indol-3-yl)ethyl)carbamate 1.383 g (compound 5, yield 71.5%).

Step 5. Synthesis of (E)-ethyl 3-(3-(((tert-butoxycarbonyl)(2-(2-methyl-1H-indol-3-yl)ethyl)amino)methyl)phenyl)acrylate

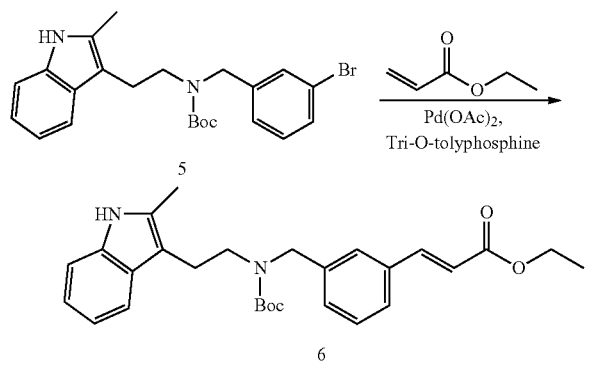

To a solution of tert-butyl 3-bromobenzyl(2-(2-methyl-1H-indol-3-yl)ethyl)carbamate (compound 5, 1.383 g, 3.119 mmol) in 50 mL Acetonitrile was added Pd(OAc)$_2$ (0.069 g, 0.307 mmol), Tri-o-tolyphosphine (0.097 g, 0.319 mmol) and triethylamine (0.70 mL, 5.036 mmol) under N$_2$. After the mixture was refluxed for 0.5 h, ethyl acrylate (0.40 mL, 3.680 mmol) was added to. The mixture was refluxed overnight. When the reaction was completed, the mixture was concentrated and purified by column chromatography on silica gel to give (E)-ethyl 3-(3-(((tert-butoxycarbonyl)(2-(2-methyl-1H-indol-3-yl)ethyl)amino)methyl)phenyl)acrylate 0.872 g (compound 6, yield 60.4%).

Step 6. Synthesis of (E)-3-(3-(((tert-butoxycarbonyl)(2-(2-methyl-1H-indol-3-yl)ethyl)amino)methyl)phenyl)acrylic acid

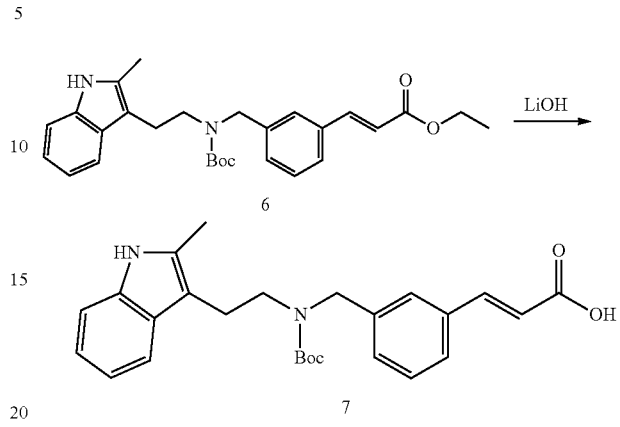

To a solution of (E)-ethyl 3-(3-(((tert-butoxycarbonyl)(2-(2-methyl-1H-indol-3-yl)ethyl)amino)methyl)phenyl)acrylate (compound 6, 0.872 g, 1.885 mmol) in 30 mL MeOH and 2 mL H$_2$O was added NaOH (0.377 g, 9.425 mmol). The solution was heated to reflux for 1 h. When the reaction was completed, the solution was concentrated and added 20 mL water. The mixture was adjusted to pH=5 by HCl solution. The mixture was extracted with EA. The organic layer was combined, washed with brine, dried over Na$_2$SO$_4$ and concentrated to give (E)-3-(3-(((tert-butoxycarbonyl)(2-(2-methyl-1H-indol-3-yl)ethyl)amino)methyl)phenyl)acrylic acid 0.656 g without further purification (compound 7, yield 80.1%).

Step 7. Synthesis of (E)-tert-butyl 3-(3-((2-aminophenyl)amino)-3-oxoprop-1-en-1-yl)benzyl(2-(2-methyl-1H-indol-3-yl)ethyl)carbamate

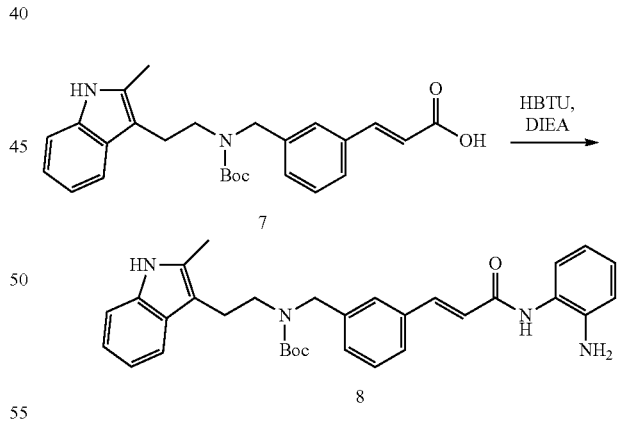

To a solution of (E)-3-(3-(((tert-butoxycarbonyl)(2-(2-methyl-1H-indol-3-yl)ethyl)amino)methyl)phenyl)acrylic acid (compound 7, 0.100 g, 0.230 mmol) in 20 mL DMF was added HBTU (0.131 g, 0.345 mmol) and DIEA (0.10 mL, 0.605 mmol). Then the benzene-1,2-diamine (0.030 g, 0.278 mmol) was added after 0.5 h. The solution was stirred at RT overnight. When the reaction was completed, the solution was quenched with 20 mL water and extracted with EA. The organic layer was combined, washed with brine, dried over Na$_2$SO$_4$, concentrated and purified by column chromatography on silica gel to give the (E)-tert-butyl 3-(3-((2-aminophenyl)amino)-3-oxoprop-1-en-1-yl)benzyl(2-(2-methyl-1H-indol-3-yl)ethyl)carbamate 0.092 g (compound 8, yield 76.0%).

Step 8. Synthesis of (E)-N-(2-aminophenyl)-3-(3-(((2-(2-methyl-1H-indol-3-yl)ethyl)amino)methyl)phenyl)acrylamide (ST49)

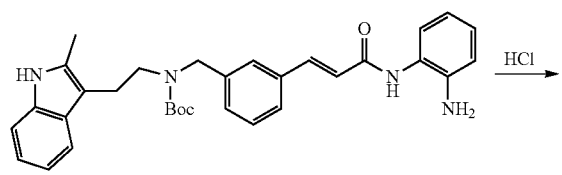

8

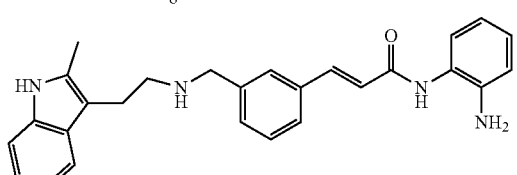

ST49

To a solution of (E)-tert-butyl 3-(3-((2-aminophenyl)amino)-3-oxoprop-1-en-1-yl)benzyl(2-(2-methyl-1H-indol-3-yl)ethyl)carbamate (compound 8, 0.092 g, 0.175 mmol) in 10 mL THF was saturated HCl (g) for 0.5 h at 0° C. When the reaction was completed, the saturated NaHCO$_3$ solution was added to adjusted pH=8. The mixture was extracted with EA for three times. The organic layer was combined, dried over Na$_2$SO$_4$, concentrated to give a residue, which was purified by column chromatography on silica gel to give (E)-N-(2-aminophenyl)-3-(3-(((2-(2-methyl-1H-indol-3-yl)ethyl)amino)methyl)phenyl)acrylamide 0.034 g (ST49, yield 45.9%)

$^1$H NMR (500 MHz, DMSO-d$_6$): δ 2.33 (s, 3H), 2.94-2.96 (m, 4H), 4.07 (s, 2H), 4.99 (m, 2H), 6.56-6.60 (m, 1H), 6.76 (dd, J=8.0, 1.0 Hz, 1H), 6.90-7.00 (m, 4H), 7.23 (d, J=8.0 Hz, 1H), 7.37 (d, J=7.5 Hz, 1H), 7.42 (d, J=7.5 Hz, 1H), 7.46-7.57 (m, 3H), 7.61 (d, J=7.5 Hz, 1H), 7.72 (s, 1H), 9.52 (s, 1H), 10.81 (s, 1H). *One —NH was not found.

LCMS found 475.1407 [M+H]$^+$, HPLC (254 nm, 95.81%).

Example 13

Synthesis of ST83

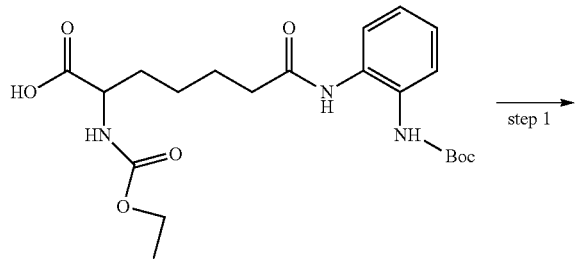

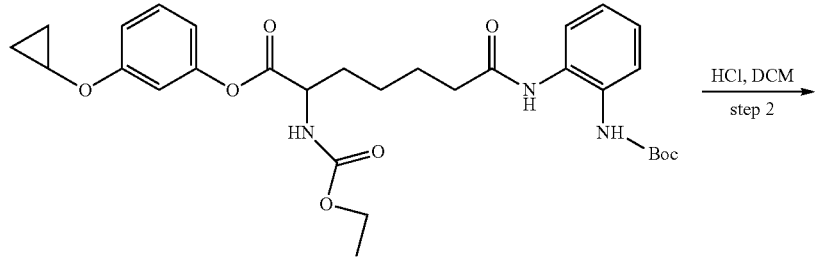

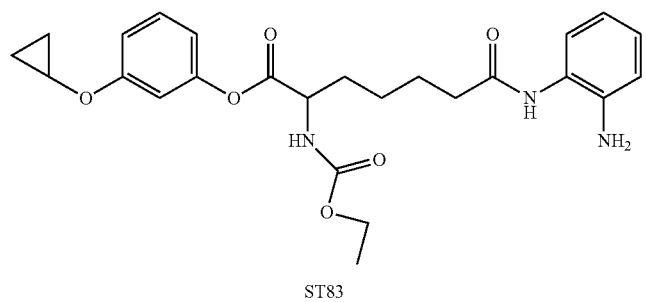

ST83

Step 1. The preparation of ethyl (7-((2-((tert-butoxycarbonyl)amino)phenyl)amino)-1-((3-cyclopropoxyphenyl)amino)-1,7-dioxoheptan-2-yl)carbamate

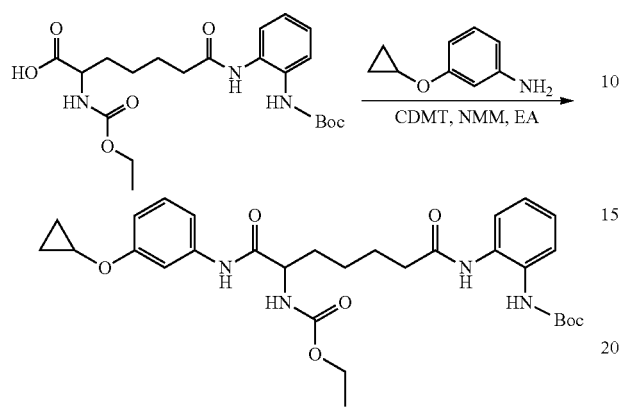

To a solution of 7-((2-((tert-butoxycarbonyl)amino)phenyl)amino)-2-((ethoxycarbonyl)amino)-7-oxoheptanoic acid (100 mg, 0.229 mmol) in 5 mL EA were added CDMT (82 mg, 0.344 mmol) and 3-cyclopropoxyaniline (68 mg, 0.472 mmol). Then NMM (0.09 mL, 0.824 mmol) was added. The solution was stirred at RT for overnight. When the reaction was completed, the solution was concentrated and purified by column chromatography on silica gel to give a yellow semisolid (100 mg, yield 76%).

Step 2. The preparation of ethyl (7-((2-aminophenyl)amino)-1-((3-cyclopropoxyphenyl)amino)-1,7-dioxoheptan-2-yl)carbamate (ST83)

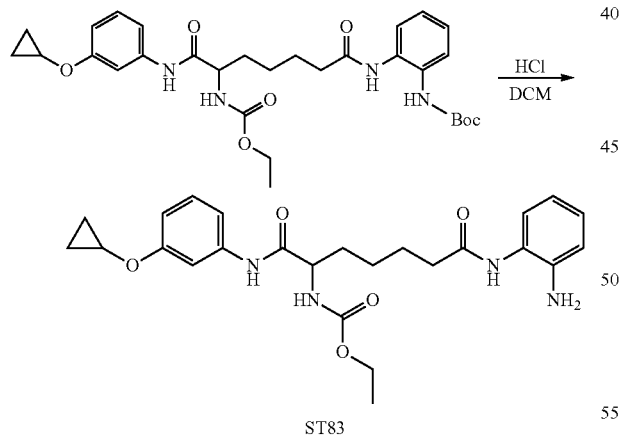

To a solution of ethyl (7-((2-((tert-butoxycarbonyl)amino)phenyl)amino)-1-((3-cyclopropoxyphenyl)amino)-1,7-dioxoheptan-2-yl)carbamate (100 mg, 0.176 mmol) in 10 mL DCM was saturated HCl (g) for 0.5 h at 0° C. When the reaction was completed, the saturated NaHCO$_3$ solution was added to adjusted pH=8. The mixture was extracted with EA for three times. The organic layer was combined, dried over Na$_2$SO$_4$, concentrated to give a residue, which was purified by column chromatography on silica gel to give a light yellow solid (ST83) (20 mg, yield 24%).

$^1$H NMR (500 MHz, DMSO-d$_6$) δ 0.60-0.67 (m, 2H), 0.71-0.80 (m, 2H), 1.16 (t, J=7.1 Hz, 3H), 1.30-1.51 (m, 2H), 1.62 (dtd, J=20.9, 13.5, 12.5, 6.4 Hz, 4H), 2.31 (t, J=7.5 Hz, 2H), 3.78 (tt, J=6.1, 3.0 Hz, 1H), 3.98 (q, J=7.1 Hz, 2H), 4.11 (td, J=8.6, 5.3 Hz, 1H), 4.80 (s, 2H), 6.51 (td, J=7.5, 1.4 Hz, 1H), 6.67-6.76 (m, 2H), 6.88 (td, J=7.6, 1.5 Hz, 1H), 7.11-7.23 (m, 3H), 7.35 (d, J=8.0 Hz, 1H), 7.44 (t, J=2.2 Hz, 1H), 9.07 (s, 1H), 10.01 (s, 1H). LCMS: [M+H]$^+$=469.2370

Example 14

Synthesis of ST1

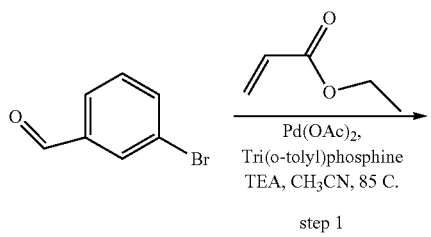

step 1

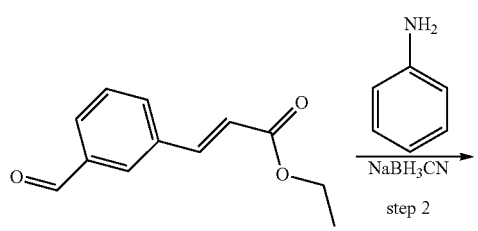

ST-117-1

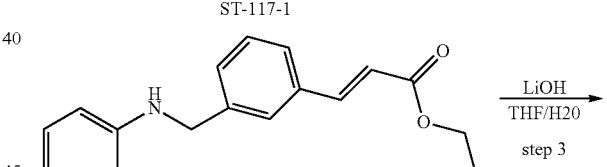

ST-117-2

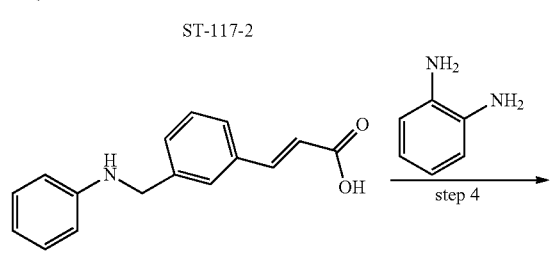

ST-117-3

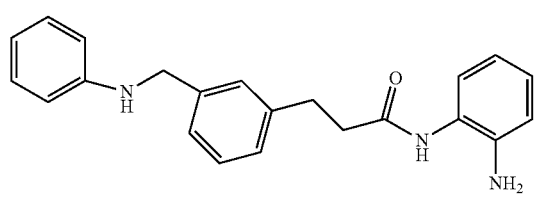

ST1

Step 1. The synthesis of (E)-ethyl 3-(3-formylphenyl)acrylate (ST-117-1)

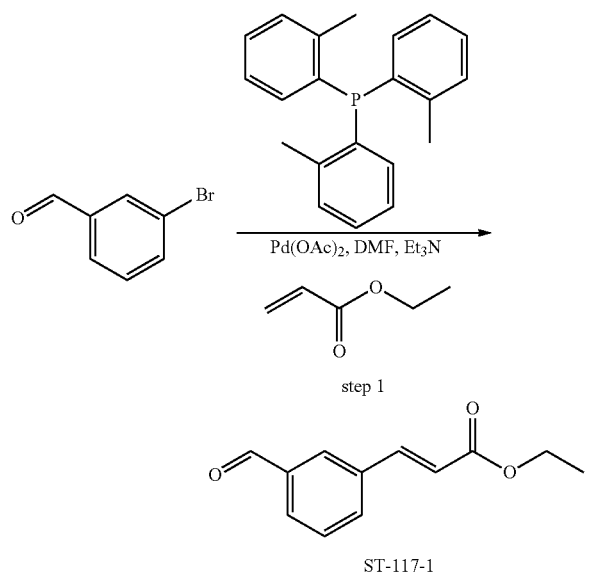

To a solution of 3-bromobenzaldehyde (2.0 g, 11 mmol, 1.0 equiv.) in DMF (40 mL) was added ethyl acrylate (1.360 g, 13.59 mmol, 1.25 equiv.), tri-o-tolylphosphine (132 mg, 0.435 mmol, 0.04 equiv.), triethylamine (2.2 g, 22 mmol, 2 equiv.), palladium acetate (49 mg, 0.22 mmol, 0.02 equiv.). The mixture was pump-filled with N₂ for four times, and then heated to 110° C. and stirred for overnight. When the reaction was completed, the reaction mixture was diluted with EA (100 mL), and was washed with water and saturated brine. The organic phase was dried, concentrated and purified by column chromatography to give the desired product as yellow oil (1.589 g, Yield: 72%).

Step 2. The synthesis of (E)-ethyl 3-(3-((phenylamino)methyl)phenyl)acrylate (ST-117-2)

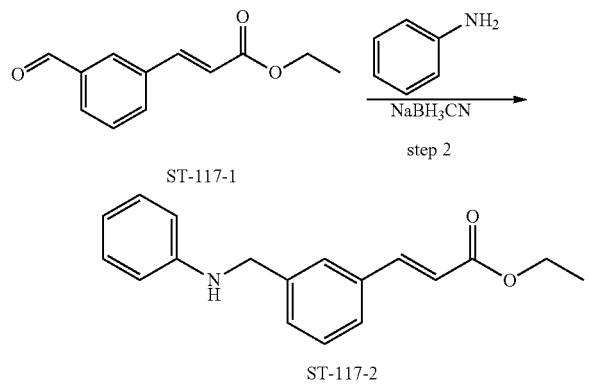

To a solution of ST-117-1 (400 mg, 1.96 mmol, 1.0 equiv.) in DMF (5 mL) was added aniline (200 mg, 2.16 mmol, 1.1 equiv.), NaBH₃CN (494 mg, 7.84 mmol, 4.0 equiv.) and AcOH (0.5 mL). After stirring at 110° C. for 2 h, the solvent was diluted with EA (100 mL), washed with water and saturated brine. The organic phase was dried, concentrated and purified by column chromatography to give the desired product as off-white solid (403 mg, Yield: 73.1%). LC-MS: m/z=282.1527 ([M+H]⁺).

Step 3. The Synthesis of (E)-3-(3-((phenylamino)methyl)phenyl)acrylic acid (ST117-3)

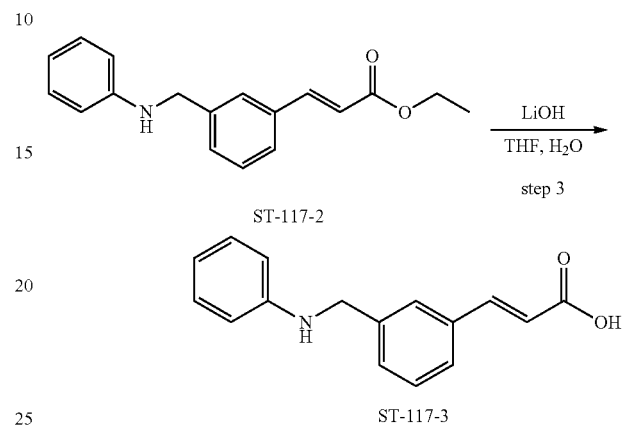

To a solution of ST-117-2 (403 mg, 1.43 mmol, 1.0 equiv.) in THF (5 mL) was added water (5 mL) and LiOH.H₂O (138 mg, 3.29 mmol, 2.3 equiv.), and the mixture was stirred for overnight at room temperature. When the reaction was completed, the solvent was removed and the residual solid was re-dissolved in water. After washing with EA, the aqueous phase was collected, and adjust to pH=3-4. The solid was filtered, and dried to give the desired product as white solid (70 mg, Yield: 19.44%). LC-MS: m/z=254.1212 [M+H]⁺.

Step 4. The synthesis of ((E)-N-(2-aminophenyl)-3-(3-((phenylamino)methyl)phenyl)acrylamide (ST1)

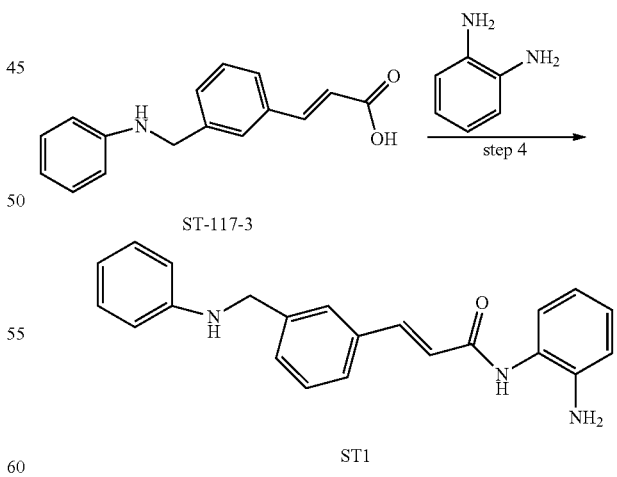

To a solution of ST-117-3 (70 mg, 0.28 mmol, 1.0 equiv.) in DMF (5 mL) was added benzene-1,2-diamine (36 mg, 0.33 mmol, 1.2 equiv.), HBTU (210 mg, 0.553 mmol, 2.0 equiv.) and DIEA (53 mg, 0.42 mmol, 1.5 equiv.). The mixture was stirred at room temperature overnight. When the reaction was completed, the solvent was diluted with EA (100 mL), washed with water and saturated brine. The organic phase was dried, concentrated and purified by column chromatography to give the desired product (ST1) as off-white solid (29 mg, Yield: 31%).

$^1$H NMR (500 MHz, DMSO-d$_6$) δ 4.30 (d, J=5.9 Hz, 2H), 4.94 (s, 2H), 6.26 (t, J=6.0 Hz, 1H), 6.52 (t, J=7.2 Hz, 1H), 6.56-6.59 (m, 3H), 6.75 (dd, J=8.0, 1.4 Hz, 1H), 6.86-6.95 (m, 2H), 7.05 (t, J=8.0 Hz, 2H), 7.35 (dd, J=7.5 Hz, 1H), 7.37-7.41 (m, 2H), 7.45-7.49 (m, 1H), 7.53 (d, J=15.7 Hz, 1H), 7.63 (s, 1H), 9.39 (s, 1H).

LC-MS: m/z=344.1778 [M+H]$^+$.

Example 15

Synthesis of ST55

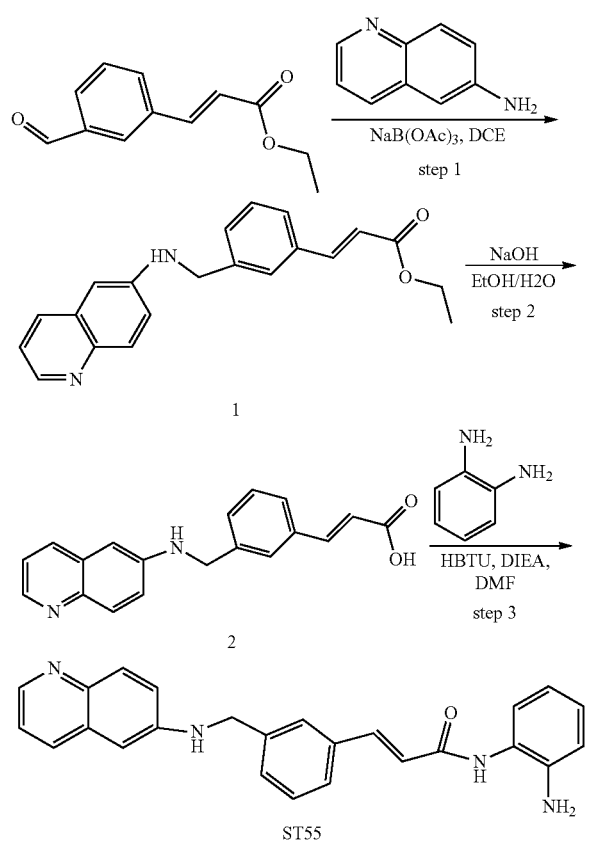

Step 1. Synthesis of (E)-ethyl 3-(3-((quinolin-6-ylamino)methyl)phenyl)acrylate

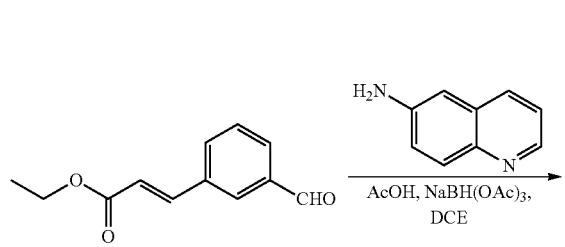

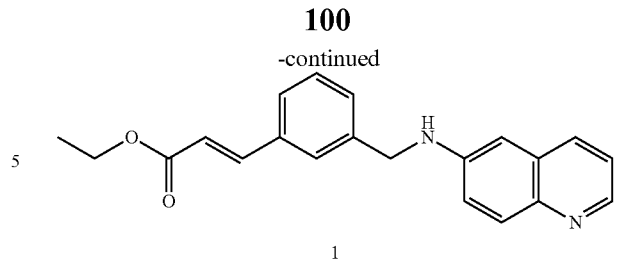

A mixture solution of (E)-ethyl 3-(3-formylphenyl)acrylate (200 mg, 1.0 mmoL), quinolin-6-amine (142 mg, 1.0 mmoL), NaBH(OAc)$_3$ (623 mg, 3.0 mmoL) and AcOH (3 drops) in DCE (10 mL) was stirred at rt for 5 hrs. The solution was concentrated under vacuum and purified by flash chromatography eluted with 30-50% ethyl acetate in petroleum ether to afford (E)-ethyl 3-(3-((quinolin-6-ylamino)methyl)phenyl)acrylate as a yellow brown oil (320 mg, yield 98%).

Step 2. Synthesis of (E)-3-(3-((quinolin-6-ylamino)methyl)phenyl)acrylic acid

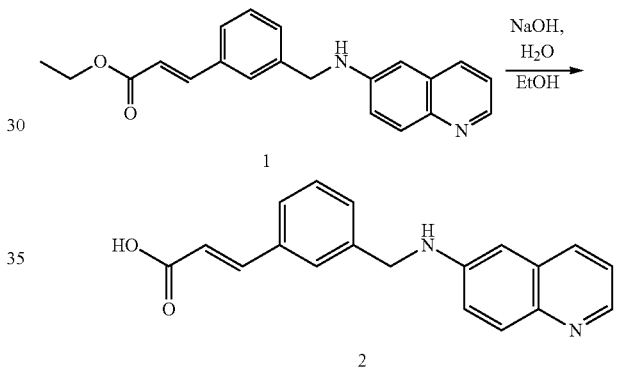

To a solution of (E)-ethyl 3-(3-((quinolin-6-ylamino)methyl)phenyl)acrylate (320 mg, 0.96 mmoL) in EtOH (10 mL) and water (9 mL) was added NaOH (400 mg) and the mixture solution was stirred overnight at room temperature. The solution was concentrated under vacuum. The pH value of the residue was adjusted to 4-5 with 1N HCl solution, and an amount of precipitation was produced, filtered and collected the precipitation to afford (E)-3-(3-((quinolin-6-ylamino)methyl)phenyl)acrylic acid as a yellow solid (249 mg, yield 85%).

Step 3. Synthesis of (E)-N-(2-aminophenyl)-3-(3-((quinolin-6-ylamino)methyl)phenyl)acrylamide (ST55)

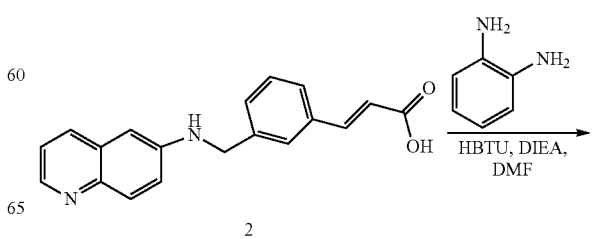

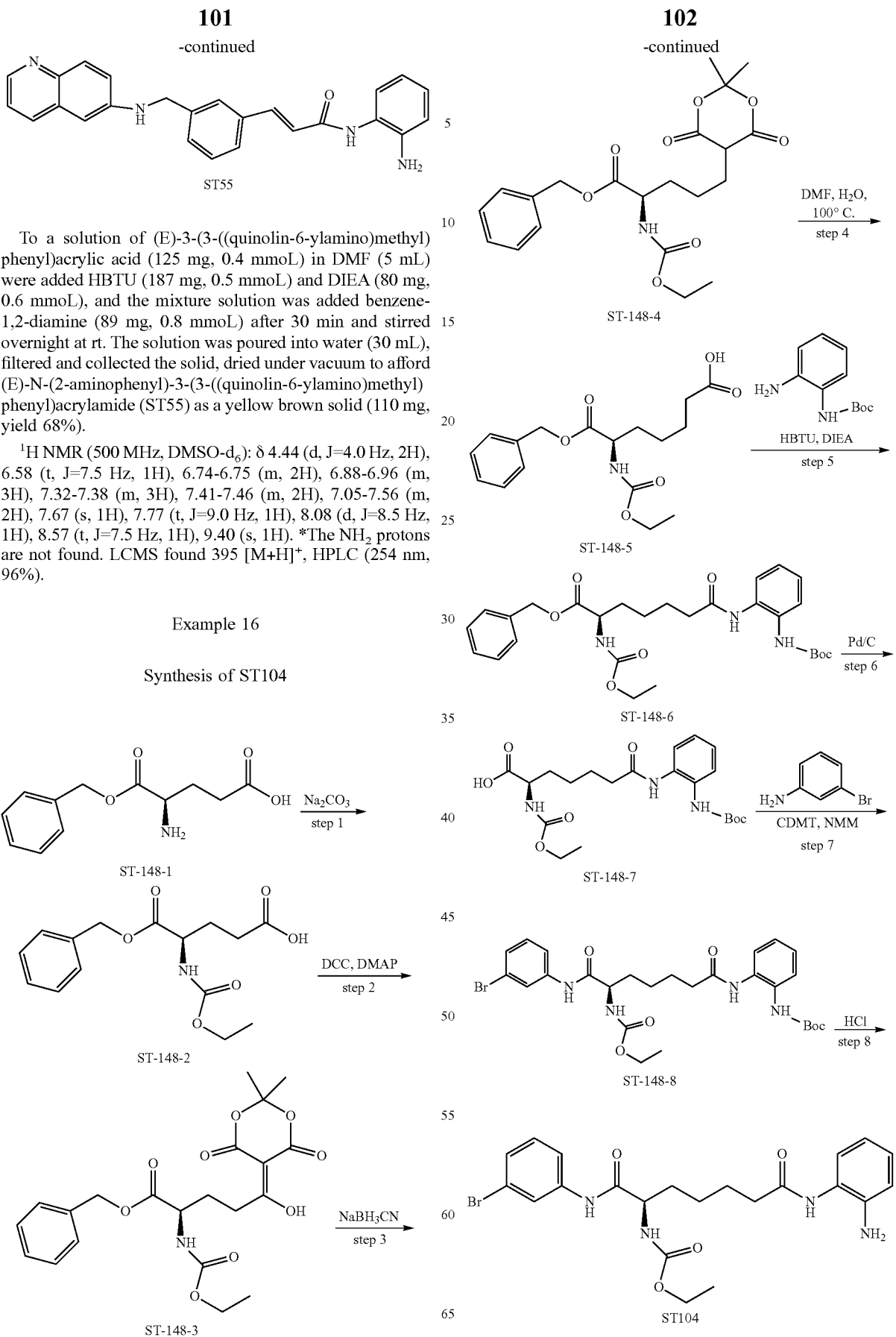

To a solution of (E)-3-(3-((quinolin-6-ylamino)methyl) phenyl)acrylic acid (125 mg, 0.4 mmoL) in DMF (5 mL) were added HBTU (187 mg, 0.5 mmoL) and DIEA (80 mg, 0.6 mmoL), and the mixture solution was added benzene-1,2-diamine (89 mg, 0.8 mmoL) after 30 min and stirred overnight at rt. The solution was poured into water (30 mL), filtered and collected the solid, dried under vacuum to afford (E)-N-(2-aminophenyl)-3-(3-((quinolin-6-ylamino)methyl) phenyl)acrylamide (ST55) as a yellow brown solid (110 mg, yield 68%).

$^1$H NMR (500 MHz, DMSO-$d_6$): δ 4.44 (d, J=4.0 Hz, 2H), 6.58 (t, J=7.5 Hz, 1H), 6.74-6.75 (m, 2H), 6.88-6.96 (m, 3H), 7.32-7.38 (m, 3H), 7.41-7.46 (m, 2H), 7.05-7.56 (m, 2H), 7.67 (s, 1H), 7.77 (t, J=9.0 Hz, 1H), 8.08 (d, J=8.5 Hz, 1H), 8.57 (t, J=7.5 Hz, 1H), 9.40 (s, 1H). *The NH$_2$ protons are not found. LCMS found 395 [M+H]$^+$, HPLC (254 nm, 96%).

Example 16

Synthesis of ST104

Step 1. Synthesis of (S)-5-(benzyloxy)-4-((ethoxycarbonyl)amino)-5-oxopentanoic acid (ST-148-2)

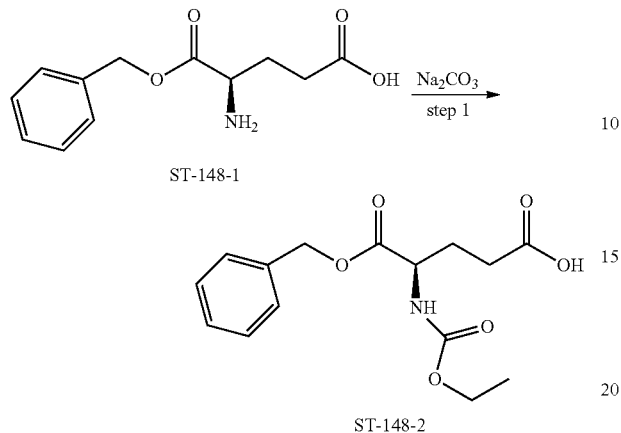

ST-148-1

ST-148-2

To a solution of ST-148-1 (1.111 g, 4.682 mmol) in 1,4-dioxane (30 mL) was added Na₂CO₃ (2.482 g, 23.415 mmol) and ethyl carbonochloridate (0.55 mL, 5.792 mmol). The mixture was stirred at RT overnight. When the reaction was completed, the solution was concentrated and 30 mL water added. Then the mixture was adjusted to pH=5 by HCl solution and was extracted with EA. The organic layer was combined, washed with brine, dried over Na₂SO₄ and concentrated give the crude product of ST-148-2 as colorless oil. (1.311 g, yield 90.5%).

Step 2. Synthesis of (S)-benzyl 5-(2,2-dimethyl-4,6-dioxo-1,3-dioxan-5-ylidene)-2-((ethoxycarbonyl)amino)-5-hydroxypentanoate (ST-148-3)

To a solution of ST-148-2 (1.311 g, 4.239 mmol) in DCM (30 mL) was added DMAP (0.155 g, 1.272 mmol), DCC (1.049 g, 5.087 mmol) and meldrum's acid (0.733 g, 5.087 mmol). The mixture was stilled at RT overnight. When the reaction was completed, 30 mL water was added and was extracted with DCM. The organic layer was combined, washed with brine, dried over Na₂SO₄, concentrated and purified by column chromatography on silica gel to give ST-148-3 as white solid. (0.880 g, yield 47.7%).

Step 3. Synthesis of (S)-benzyl 5-(2,2-dimethyl-4,6-dioxo-1,3-dioxan-5-yl)-2-((ethoxycarbonyl)amino)pentanoate (ST-148-4)

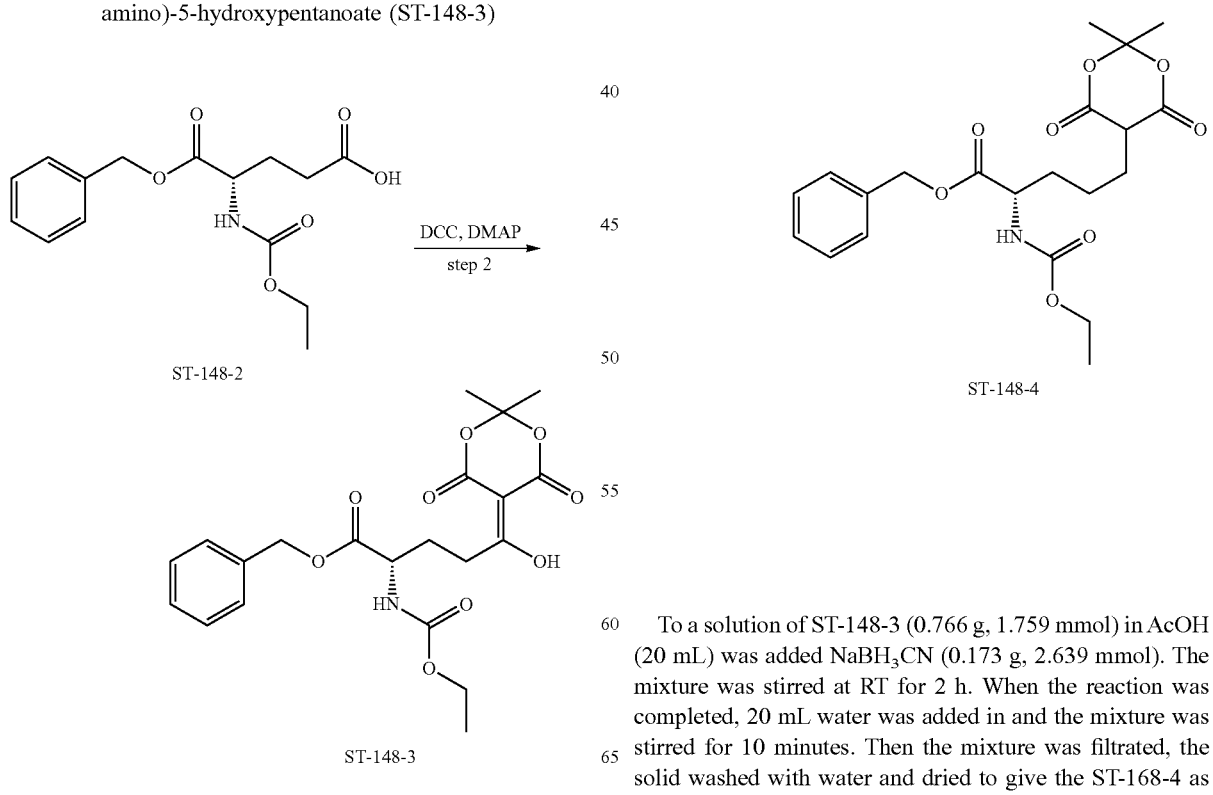

ST-148-2

ST-148-3

ST-148-3

ST-148-4

To a solution of ST-148-3 (0.766 g, 1.759 mmol) in AcOH (20 mL) was added NaBH₃CN (0.173 g, 2.639 mmol). The mixture was stirred at RT for 2 h. When the reaction was completed, 20 mL water was added in and the mixture was stirred for 10 minutes. Then the mixture was filtrated, the solid washed with water and dried to give the ST-168-4 as yellow solid. (0.311 g, yield 41.9%).

Step 4. Synthesis of (S)-7-(benzyloxy)-6-((ethoxy-carbonyl)amino)-7-oxoheptanoic acid (ST-148-5)

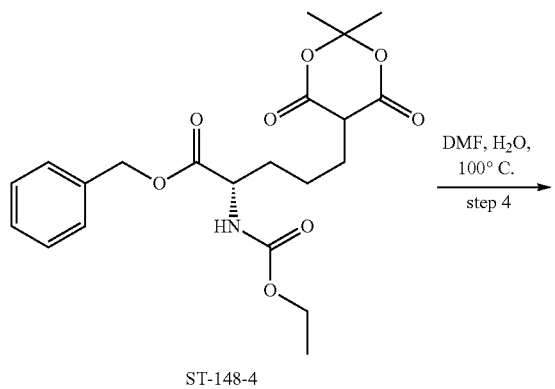

ST-148-4

A solution of ST-148-4 (0.311 g, 0.738 mmol) in DMF (9 mL) and H₂O (1.0 mL) was stirred at 100° C. for 1 hour. When the reaction was completed, 20 mL water was added in and the solution was adjusted to pH=3 by HCl solution. Then the solution was extracted with EA. The organic layer was combined, washed with brine, dried over Na₂SO₄ and concentrated give the ST-148-5 as yellow oil (0.133 g, yield: 53.4%).

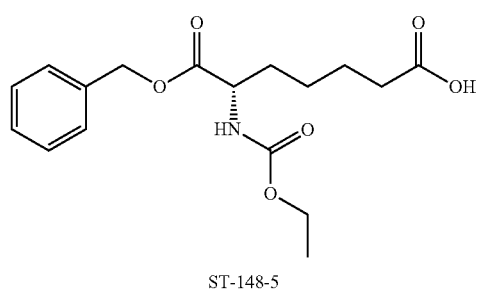

ST-148-5

Step 5. Synthesis of (S)-benzyl 7-((2-((tert-butoxy-carbonyl)amino)phenyl)amino)-2-((ethoxycarbonyl)amino)-7-oxoheptanoate (ST-148-6)

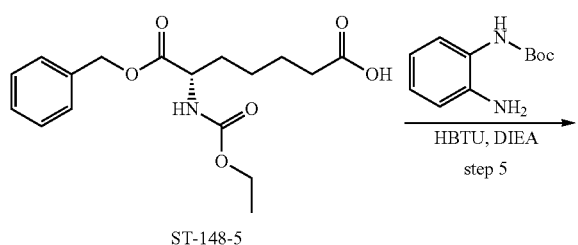

ST-148-5

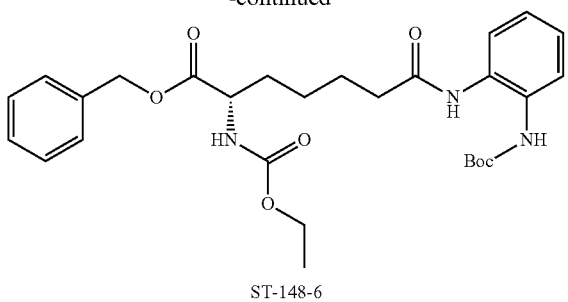

ST-148-6

To a solution of ST-148-5 (0.133 g, 0.394 mmol) was added HBTU (0.224 g, 0.591 mmol) and DIEA (0.15 mL, 0.788 mmol). Then the tert-butyl (2-aminophenyl)carbamate (0.099 g, 0.475 mmol) was added after 0.5 h. The solution was stirred at RT overnight. When the reaction was completed, the solution was quenched with 20 mL water and extracted with EA. The organic layer was combined, washed with brine, dried over Na₂SO₄, concentrated and purified by column chromatography on silica gel to give ST-148-6 as yellow solid. (0.151 g, yield 72.6%).

Step 6. Synthesis of (S)-7-((2-((tert-butoxycarbonyl)amino)phenyl)amino)-2-((ethoxycarbonyl)amino)-7-oxoheptanoic acid (ST-148-7)

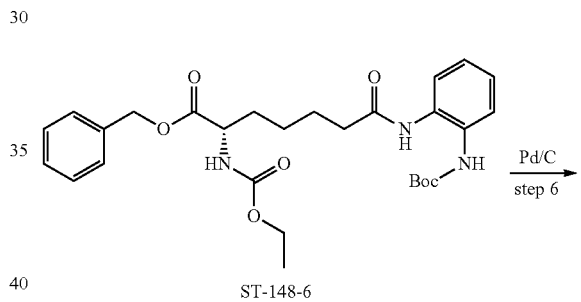

ST-148-6

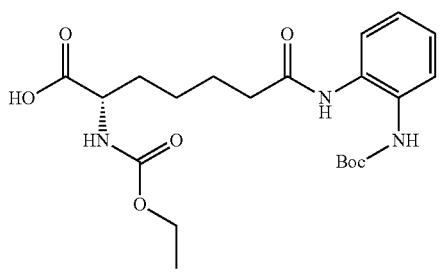

ST-148-7

To a solution of ST-148-6 (0.151 g, 0.286 mmol) in 20 mL MeOH was added Pd/C (0.030 g). The solution was stirred at RT overnight in H₂. When the reaction was completed, the mixture was filtered and the organic layer was concentrated to give ST-148-7 as colorless oil. (0.100 g, yield 80.0%).

Step 7. Synthesis of ST-148-8

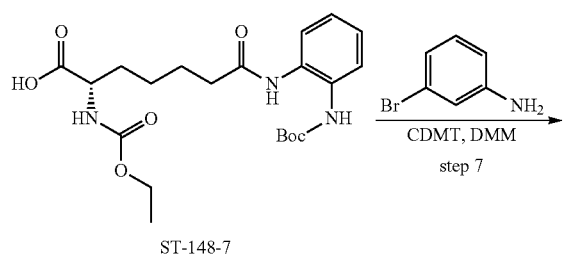

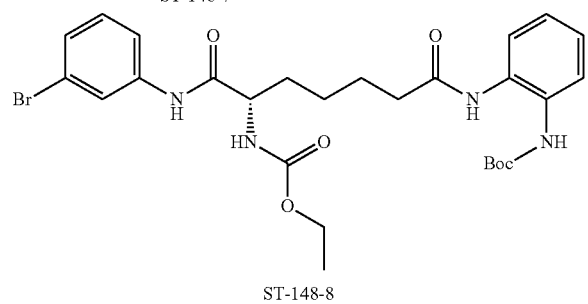

To a solution of ST-148-7 (0.100 g, 0.229 mmol) in 20 mL EA was added CDMT (0.060 g, 0.342 mmol), NMM (0.05 mL, 0.458 mmol) and 3-bromoaniline (0.03 mL, 0.275 mmol). The solution was stirred at RT overnight. When the reaction was completed, the solution was concentrated and purified by column chromatography on silica gel to give ST-148-8 (0.110 g, yield 81.5%).

Step 8. Synthesis of (S)-ethyl (7-((2-aminophenyl)amino)-1-((3-bromophenyl)amino)-1,7-dioxoheptan-2-yl)carbamate (ST104)

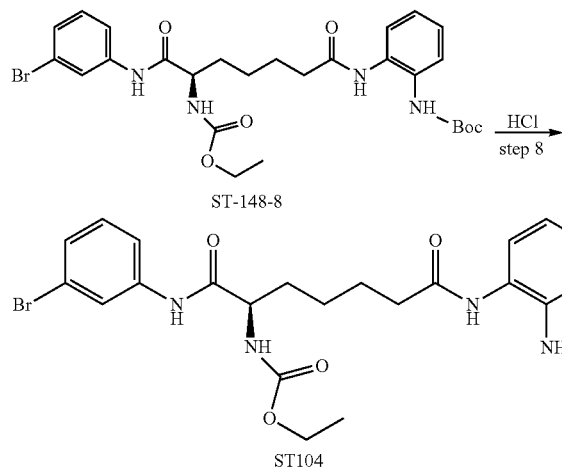

To a solution of ST-148-8 (0.110 g, 0.186 mmol) in 10 ml THF in 10 mL saturated by HCl(g) for 0.5 h at 0° C. When the reaction was completed, the saturated NaHCO₃ solution was added to adjusted pH=8. The mixture was extracted with EA for three times. The organic layer was combined, dried over Na₂SO₄, concentrated and purified by column chromatography on silica gel to give ST104 as yellow solid (0.061 g, yield 67.0%).

Purity: 94.9% (LC-MS, 254 nm)

¹H NMR (400 MHz, DMSO-d₆): δ 1.17 (t, J=7.2 Hz, 3H), 1.33-1.45 (m, 2H), 1.57-1.73 (m, 4H), 2.31 (t, J=7.2 Hz, 2H), 3.99 (q, J=7.2 Hz, 2H), 4.06-4.12 (m, 1H), 4.79 (s, 2H), 6.50-6.53 (m, 1H), 6.71 (d, J=0.8, 8.0 Hz, 1H), 6.86-6.90 (m, 1H), 7.13 (d, J=8.0 Hz, 1H), 7.23-7.29 (m, 2H), 7.41 (d, J=7.6 Hz, 1H), 7.50 (d, J=7.6 Hz, 1H), 7.97 (s, 1H), 9.06 (s, 1H), 10.19 (s, 1H).

LC-MS: m/z=491.1311 ([M+H]⁺).

Example 17

Synthesis of ST4

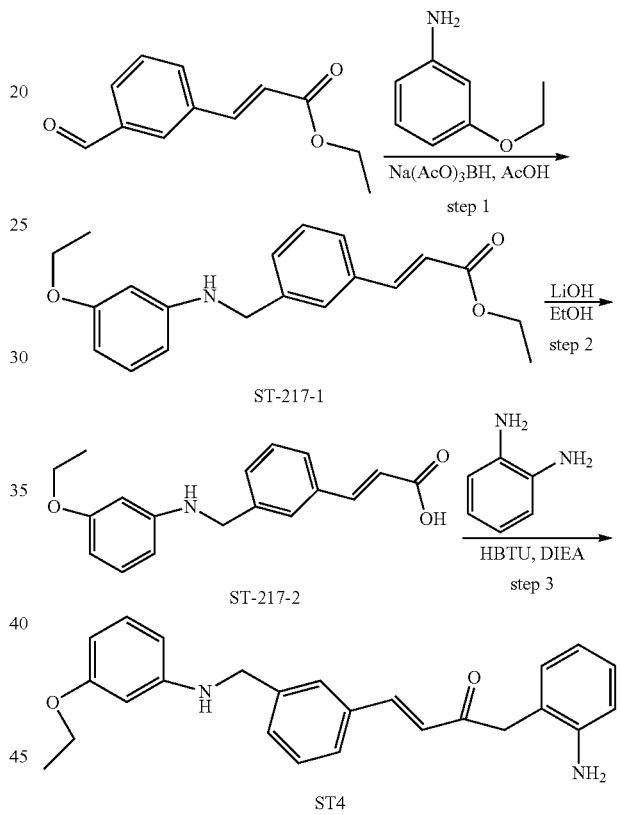

Step 1. The sythesis of ST-217-1

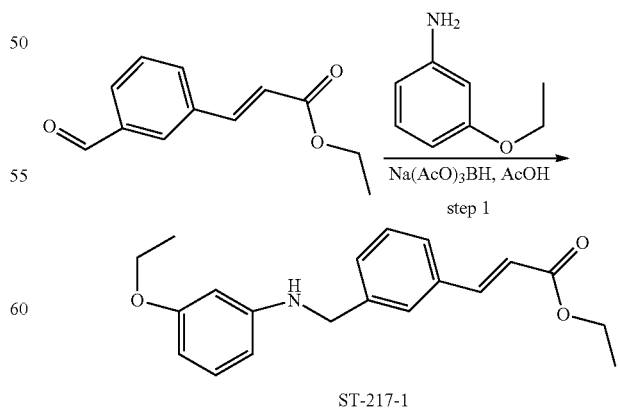

To a solution of SM (0.340 g, 1.67 mmol) in DCE (8 mL) were added 4-ethoxyaniline (0.251 g, 1.83 mmol), NaBH (AcO)₃ (1.061 g, 5.01 mmol) and AcOH (0.5 mL, 0.01 mmol). The mixture was stirred at RT about 3 hours. LC-MS showed completion of the reaction. The reaction was diluted with saturated aqueous sodium bicarbonate and extracted with EA (10 mL) three times. The organic layers were combined, washed with water and brine (twice), dried over magnesium sulfate, filtered, and concentrated under reduced pressure and purified by column chromatography. The desired product ST-217-1 (0.430 g, 1.32 mmol. Yield: 79%).

Step 2. The synthesis of (E)-3-(3-(((3-ethoxyphenyl)amino)methyl)phenyl)acrylic acid (ST-217-2)

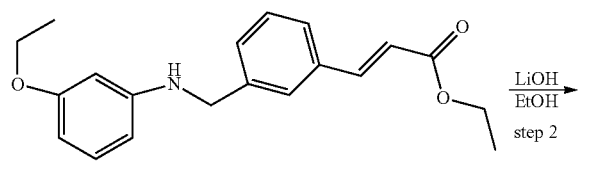

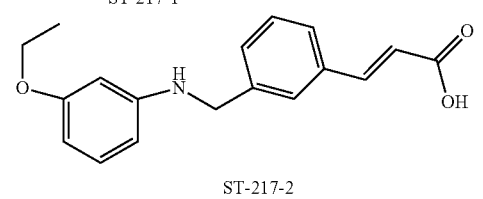

To a solution of ST-217-1 (0.430 g, 1.32 mmol) in ethanol (10 mL) and H₂O (1 mL) was added LiOH (0.080 g, 3.306 mmol). The mixture was stirred at RT for 1 hour. The mixture was concentrated and water (10 mL) was added. The mixture was adjusted to pH=5 by HCl solution and then extracted with ethyl acetate (10 mL×3). The organic layer was combined and then dried over sodium sulfate The mixture was filtered out. The filtrate was concentrated under vacuum to give ST-217-2 without further purification. (0.136 g, 0.46 mmol, Yield: 35%).

Step 3. The synthesis of (E)-N-(2-aminophenyl)-3-(3-(((3-ethoxyphenyl)amino)methyl)phenyl)acrylamide (ST4)

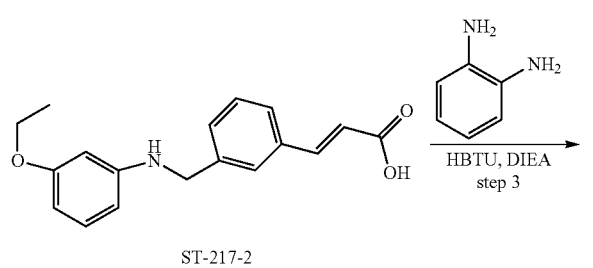

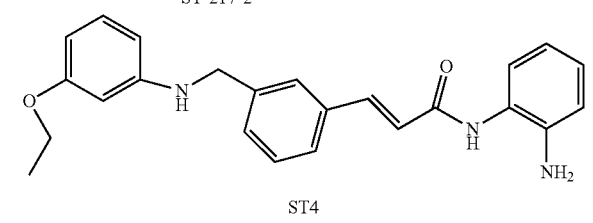

To a solution of ST-217-2 (0.136 g, 0.46 mmol) in DMF (5 mL) were added HBTU (0.225 g, 0.595 mmol) and DIEA (0.1 mL, 0.788 mmol). Then the benzene-1, 2-diamine (0.059 g, 0.550 mmol) was added after 0.5 h. The solution was stirred at RT for 4 h. When the reaction was completed, the solution was quenched with water (50 mL) and extracted with EA. The organic layer was combined, washed with brine, dried over Na₂SO₄, concentrated and purified by prep-HPLC to give ST4. (0.045 g, 0.12 mmol, Yield: 26%).

Purity: 95% (LC-MS, 254 nm); LC-MS: m/z=388.2174 ([M+H]⁺).

¹H NMR (400 MHz, DMSO-d₆) δ1.33-1.13 (m, 3H), 3.89 (q, J=6.9 Hz, 2H), 4.28 (d, J=5.7 Hz, 2H), 4.95 (s, 1H), 6.10 (d, J=5.7 Hz, 2H), 6.19 (dd, J=8.0, 1.9 Hz, 1H), 6.27 (t, J=6.1 Hz, 1H), 6.57 (td, J=7.5, 1.4 Hz, 1H), 6.75 (dd, J=8.0, 1.5 Hz, 1H), 6.98-6.84 (m, 3H), 7.57-7.30 (m, 4H), 7.61 (s, 1H), 9.39 (s, 1H).

Example 18

Synthesis of ST116

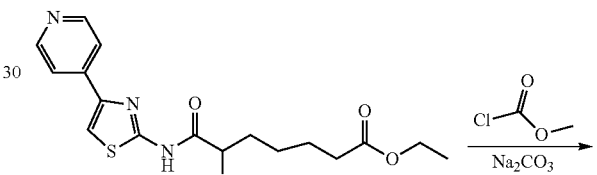

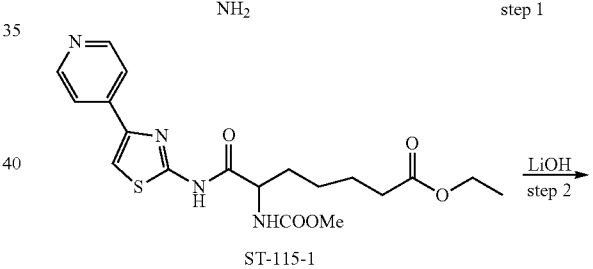

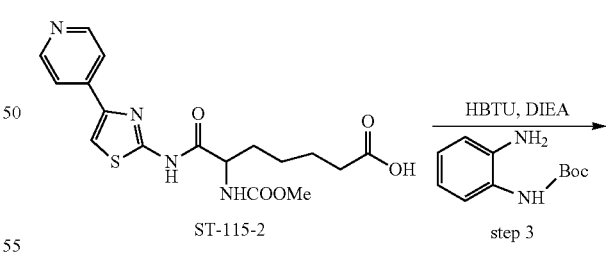

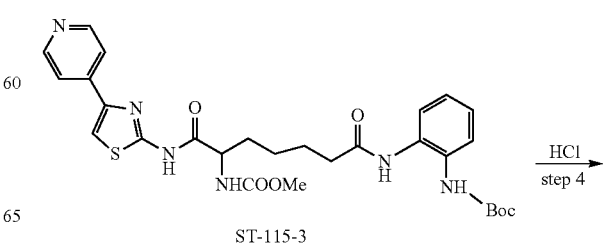

111

-continued

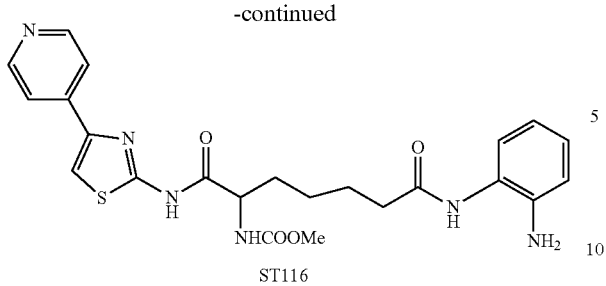
ST116

Step 1. The Synthesis of ethyl 6-((methoxycarbonyl)amino)-7-oxo-7-((4-(pyridin-4-yl)thiazol-2-yl)amino)heptanoate (ST-115-1)

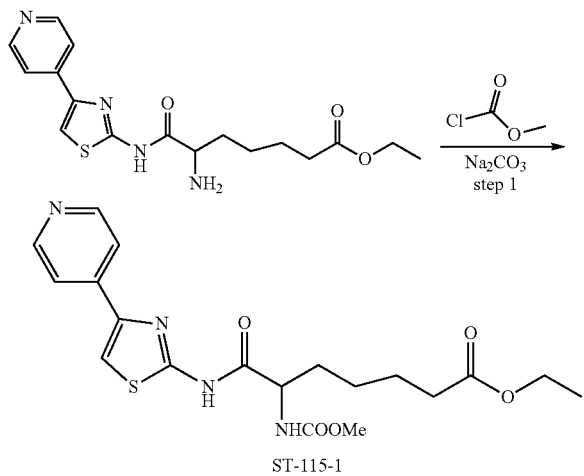

To a solution of ethyl 6-amino-7-oxo-7-((4-(pyridin-4-yl)thiazol-2-yl)amino)heptanoate (500 mg, 1.380 mmol) in 1,4-dioxane (10 mL) and water (2 mL) was added $Na_2CO_3$ (439 mg, 4.139 mmol). Then the methyl carbonochloridate (196 mg, 2.070 mmol) was added dropwise at 0° C. The solution was stirred at room temperature overnight. When the reaction was completed, the solution was concentrated and water (50 mL) was added. The solution was extracted with EA (50 mL×2). The organic layer was combined, washed with brine, dried over $Na_2SO_4$. The mixture was purified by column chromatography on silica gel to give the product of ST-115-1 (300 mg, yield 517%).

Step 2. The synthesis of 6-((methoxycarbonyl)amino)-7-oxo-7-((4-(pyridin-4-yl)thiazol-2-yl) amino)heptanoic acid (ST-115-2)

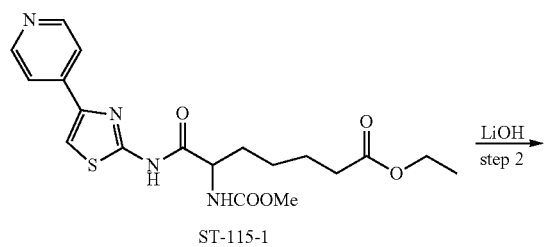

112

-continued

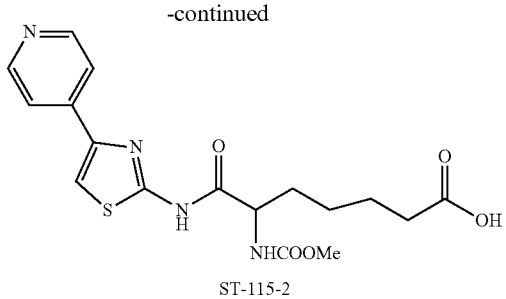
ST-115-2

To a solution of ST-115-1 (300 mg, 0.713 mmol) in EtOH (10 mL) was added $LiOH \cdot H_2O$ (150 mg, 3.567 mmol). The solution was stirred at room temperature overnight. When the reaction was completed, the solution was concentrated and water (50 mL) was added. The mixture was adjusted to pH=5 with HCl (1 mol/L) solution. The mixture was filtered and the solid ST-115-2 was used for next step without further purification (200 mg, yield 71.4%).

Step 3. The synthesis of methyl (7-((2-(((tert-butoxycarbonyl) amino)phenyl)amino)-1,7-dioxo-1-((4-(pyridin-4-yl)thiazol-2-yl)amino)heptan-2-yl) carbamate (ST-115-3)

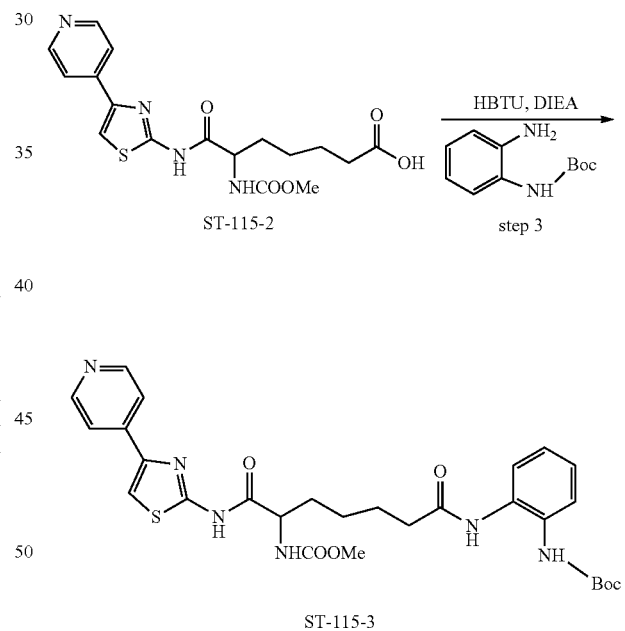

To a solution of ST-115-2 (200 mg, 0.510 mmol) in DMF (5 mL) were added HBTU (290 mg, 0.765 mmol) and DIEA (99 mg, 0.765 mmol). Then the tert-butyl (2-aminophenyl) carbamate (125 mg, 0.601 mmol) was added after 0.5 h. The solution was stirred at room temperature overnight. When the reaction was completed, the solution was quenched with water (20 mL) and extracted with EA (50 mL×2). The organic layer was combined, washed with brine, dried over $Na_2SO_4$, concentrated and purified by column chromatography on silica gel to give ST-115-3 (160 mg, yield 53.9%).

Step 4. The synthesis of methyl (7-((2-aminophenyl) amino)-1,7-dioxo-1-((4-(pyridin-4-yl)thiazol-2-yl)amino)heptan-2-yl)carbamate (ST116)

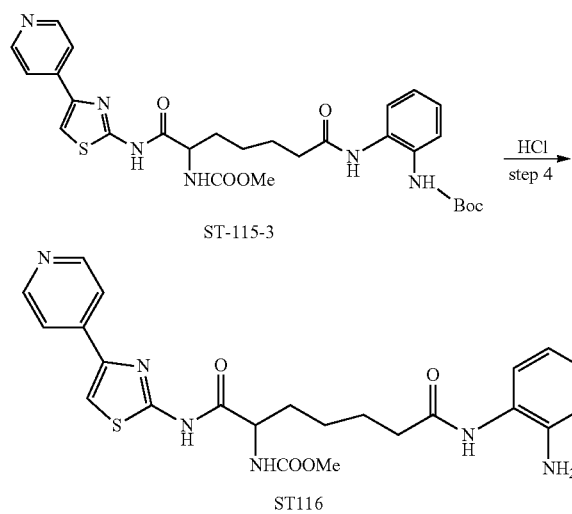

To a solution of ST-115-3 (160 mg, 0.275 mmol) in 5 mL DCM was saturated with HCl(g) for 0.5 h at 0° C. When the reaction was completed, the saturated NaHCO₃ solution was added to adjust pH=8. The mixture was purified by prep-HPLC to give ST116 (20 mg, yield 15.1%).

LC-MS: m/z=483.1820 ([M+H]$^+$).

$^1$H NMR (400 MHz, DMSO-d6) δ 1.28-1.50 (m, 2H), 1.51-1.83 (m, 4H), 2.32 (t, J=7.4 Hz, 2H), 3.55 (s, 3H), 4.25 (s, 1H), 4.82 (s, 2H), 6.45-6.58 (m, 1H), 6.70 (dd, J=8.0, 1.4 Hz, 1H), 6.79-6.93 (m, 1H), 7.15 (dd, J=7.9, 1.6 Hz, 1H), 7.50 (s, 1H), 7.81-7.88 (m, 2H), 7.94 (s, 1H), 8.61 (d, J=5.2 Hz, 2H), 9.12 (s, 1H), 12.50 (s, 1H).

Example 19

Synthesis of ST102

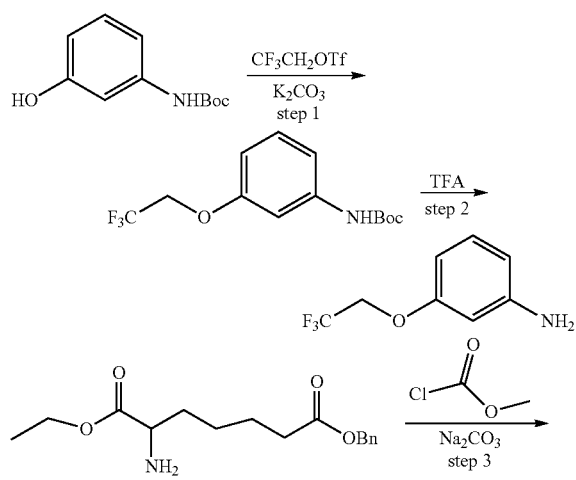

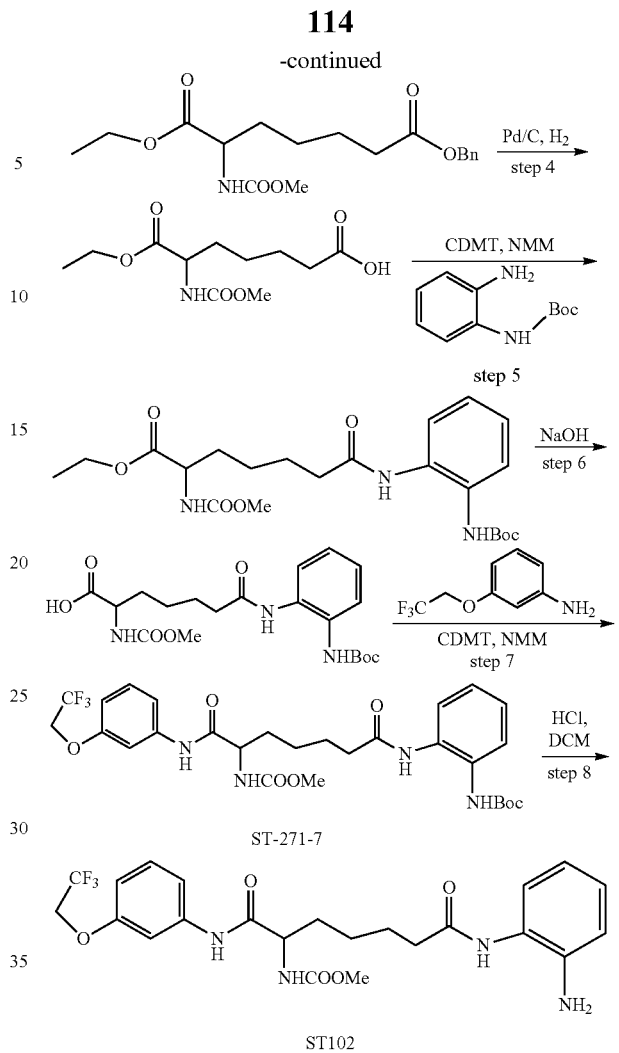

Step 1. The synthesis of tert-butyl (3-(2,2-trifluoroethoxy)phenyl)carbamate

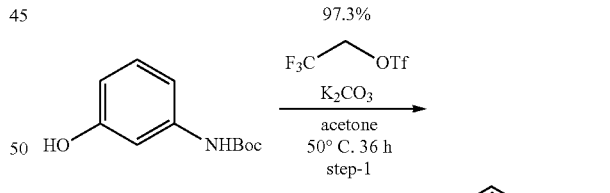

To a solution of tert-butyl (3-hydroxyphenyl)carbamate (600 mg, 2.87 mmol, 1 eq.) in acetone (20 mL) was added 2,2,2-trifluoroethyl trifluoromethanesulfonate (1000 mg, 4.31 mmol, 1.5 equiv.) and K₂CO₃ (800 mg, 5.79 mmol, 2 eq.). After stirring at 50° C. for 36 hours, the resulting mixture was cooled to the room temperature, and the solid was filtered out. The filtrate was concentrated and purified by column chromatography (EA:PE=1:20-1:5) to give tert-butyl (3-(2,2,2-trifluoroethoxy)phenyl)carbamate as a light yellow solid (813 mg, 2.79 mmol, yield: 97.3%).

Step 2. The synthesis of 3-(2,2,2-trifluoroethoxy)aniline

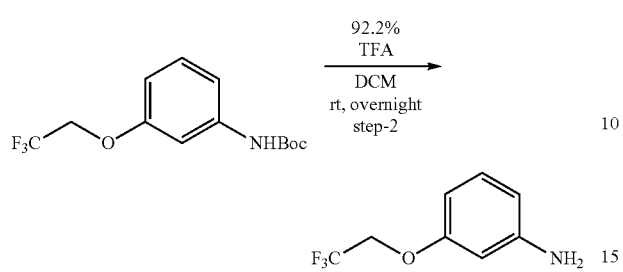

To a solution of tert-butyl (3-(2,2,2-trifluoroethoxy)phenyl)carbamate (813 mg, 2.79 mmol, 1 eq.) in DCM (10 mL) was added 3 ml of TFA. The resulting mixture was stirred at room temperature overnight. To the mixture was added 10 ml of ice/water and the pH value was adjusted to 8-9 with NaHCO$_3$ (sat. aq). The organic layer was collected and the water phase was extracted with 3×30 ml of DCM. The combined organic phase was dried over anhydrous sodium sulfate and concentrated under vacuum to give 3-(2,2,2-trifluoroethoxy)aniline as a yellow solid (492 mg, 2.57 mmol; yield: 92.2%).

Step 3. The synthesis of 7-benzyl 1-ethyl 2-((methoxycarbonyl)amino)heptanedioate

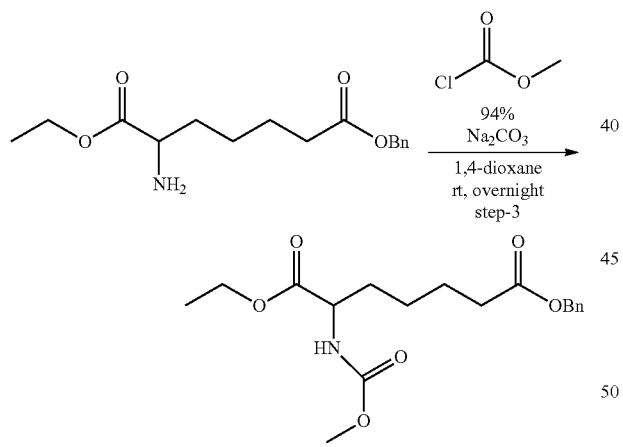

To a solution of 7-benzyl 1-ethyl 2-aminoheptanedioate (300 mg, 1.02 mmol, 1 eq.) in 1,4-dioxane (6 mL) was added methyl carbonochloridate (145 mg, 1.53 mmol, 1.5 eq.) and then Na$_2$CO$_3$ (325 mg, 3.06 mmol, 3 eq.). The resulting mixture was stirred at room temperature overnight. The mixture was concentrated under vacuum to remove 1,4-dioxane and then diluted with 30 ml of water and extracted with 3×30 ml of EA. The organic layers were combined and dried over anhydrous sodium sulfate and concentrated under vacuum. The residue was purified by column chromatography (EA:PE=1:20-1:2) to give 7-benzyl 1-ethyl 2-((methoxycarbonyl)amino)heptanedioate as a yellow oil (340 mg, 0.97 mmol; yield: 94%).

Step 4. The synthesis of 7-ethoxy-6-((methoxycarbonyl)amino)-7-oxoheptanoic acid

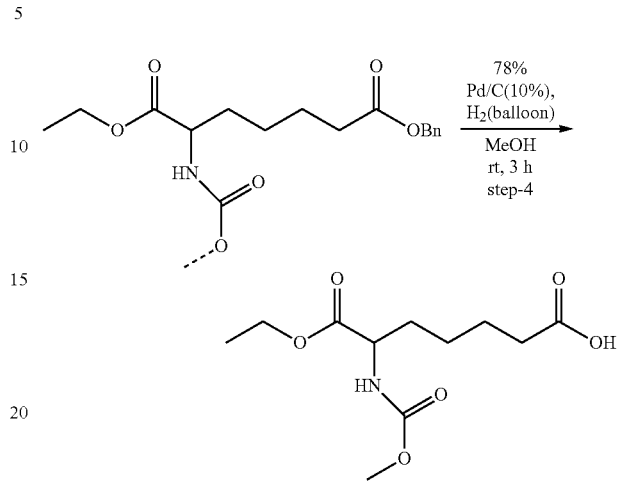

To a solution of 7-benzyl 1-ethyl 2-((methoxycarbonyl)amino)heptanedioate (340 mg, 0.97 mmol, 1 eq.) in MeOH (15 mL) was added 10% Pd/C (340 mg). The mixture was stirred under hydrogen (balloon) at room temperature for 3 h. The reaction mixture was filtered through Celite. The filtrate was concentrated to give 7-ethoxy-6-((methoxycarbonyl)amino)-7-oxoheptanoic acid as a yellow oil (196 mg, 0.91 mmol; yield: 78%).

Step 5. The synthesis of ethyl 7-((2-((tert-butoxycarbonyl)amino)phenyl)amino)-2-((methoxycarbonyl)amino)-7-oxoheptanoate

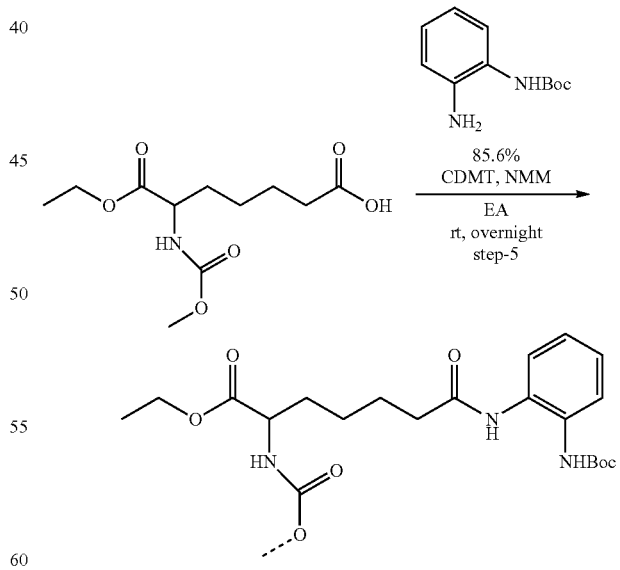

To a mixture of 7-ethoxy-6-((methoxycarbonyl)amino)-7-oxoheptanoic acid (196 mg, 0.91 mmol, 1 eq.), CDMT (239 mg, 1.36 mmol, 1.5 equiv.) and tert-butyl (2-aminophenyl)carbamate (208 mg, 1.00 mmol, 1.1 equiv.) in EA (15 mL) was added NMM (343 mg, 3.36 mmol, 3.7 equiv.) dropwise with stirring at room temperature. After stirring at room temperature overnight, LCMS showed completion of the reaction. The reaction mixture was diluted with 35 ml of EA, and washed with 30 ml of 5% citric acid (aq.), 30 ml of NaHCO$_3$ (sat. aq.) successively. The organic phase was dried over anhydrous sodium sulfate and concentrated under vacuum. The residue was purified by column chromatography (EA:PE=1:10 to 1:5 to 1:2) to give ethyl 7-((2-((tert-butoxycarbonyl)amino)phenyl)amino)-2-((methoxycarbonyl)amino)-7-oxoheptanoate as a yellow oil (322 mg, 0.71 mmol; yield: 85.6%).

Step 6. The synthesis of 7-((2-((tert-butoxycarbonyl)amino)phenyl)amino)-2-((methoxycarbonyl)amino)-7-oxoheptanoic acid

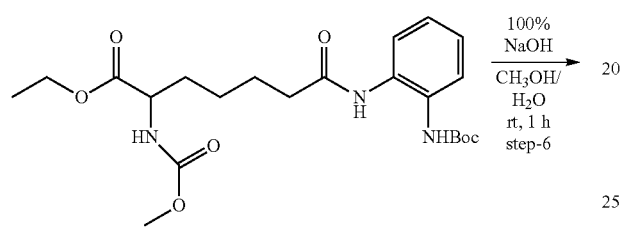

To a solution of ethyl 7-((2-((tert-butoxycarbonyl)amino)phenyl)amino)-2-((methoxycarbonyl)amino)-7-oxoheptanoate (322 mg, 0.71 mmol, 1 eq.) in MeOH (8 mL) was added NaOH (114 mg, 2.85 mmol, 4 equiv.) (in 3 ml of water) dropwise with stirring at 0° C. After stirring at room temperature for 1 hour, the MeOH was removed, and the residue was diluted with 30 ml of ice/water. The resulting mixture was acidified to pH=5-6 with HCl (1 M) and extracted with 3×30 ml of EA. The combined organic phase was washed with water and dried over anhydrous sodium sulfate and concentrated under vacuum to give 7-((2-((tert-butoxycarbonyl)amino)phenyl)amino)-2-((methoxycarbonyl)amino)-7-oxoheptanoic acid as a yellow solid (302 mg, 0.71 mmol; yield: 100%).

Step 7. The Synthesis of ST-271-7

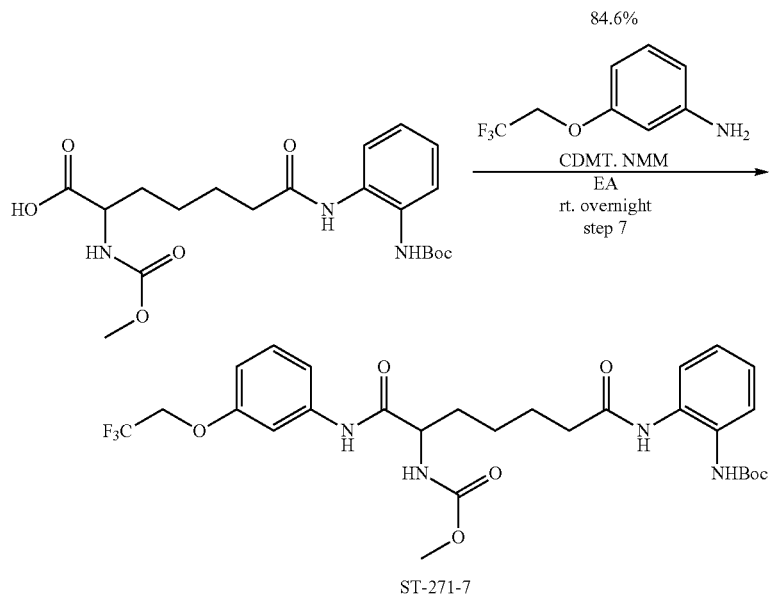

-continued

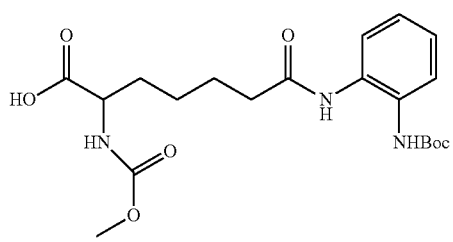

To a mixture of crude 7-((2-((tert-butoxycarbonyl)amino)phenyl)amino)-2-((methoxycarbonyl)amino)-7-oxoheptanoic acid (302 mg, 0.71 mmol, 1 eq.), CDMT (200 mg, 1.139 mmol, 1.6 equiv.) and 3-(2,2,2-trifluoroethoxy)aniline (164 mg, 0.858 mmol, 1.2 equiv.) in EA (15 mL) was added NMM (357 mg, 3.495 mmol, 4.9 equiv.) dropwise. After stirring at room temperature overnight, LCMS showed completion of the reaction. The reaction mixture was quenched with 50 ml of ice/water, and extracted with 3×30 ml of EA. The organic layers were combined and dried over anhydrous sodium sulfate and concentrated under vacuum. The residue was purified by column chromatography (EA:PE=1:20-1:1) to give ST-271-7 as a yellow oil (360 mg, 0.603 mmol; yield: 84.6%).

Steps 8. The synthesis of methyl (7-((2-aminophenyl)amino)-1,7-dioxo-1-((3-(2,2,2-trifluoroethoxy)phenyl)amino)heptan-2-yl)carbamate hydrochloride (ST102)

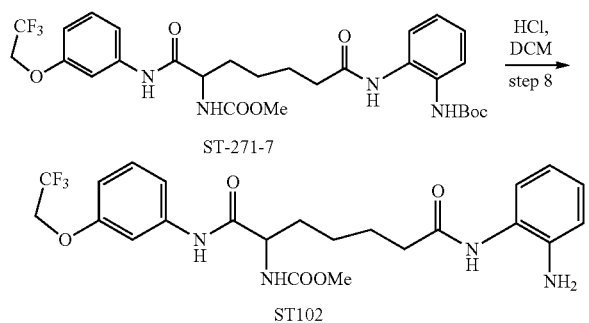

A solution of ST-271-7 (42 mg, 0.051 mmol) in DCM (20 mL) was stirred for 2 hours under HCl (g). The solid formed was collected by filtration and washed with 2×2 ml DCM. The desired product methyl (7-((2-aminophenyl)amino)-1,7-dioxo-1-((3-(2,2,2-trifluoroethoxy)phenyl)amino)heptan-2-yl) carbamate hydrochloride (ST102) was isolated as an off-white solid (162 mg, yield: 50.4%).

$^1$H NMR (500 MHz, MeOD) δ 7.39 (d, J=2.0 Hz, 1H), 7.24 (t, J=8.2 Hz, 1H), 7.18-7.12 (m, 1H), 7.07-6.99 (m, 2H), 6.84 (d, J=7.9 Hz, 1H), 6.75 (dd, J=8.2, 2.3 Hz, 1H), 6.70 (t, J=7.6 Hz, 1H), 4.49 (q, J=8.5 Hz, 2H), 4.23 (dd, J=8.3, 5.7 Hz, 1H), 3.65 (s, 3H), 2.44 (q, J=7.1 Hz, 2H), 1.91-1.81 (m, 1H), 1.80-1.69 (m, 3H), 1.61-1.44 (m, 2H).

LC-MS: m/z=497 [M−Cl]$^+$

Example 20

Mammalian Two-Hybrid Assay Used to Determine the Inhibitory Effects of the Compounds on MEF2D and HDAC4 Protein Interactions Methods Detection of MEF2D and HDAC4 interactions. In this mammalian two-hybrid assay, HDAC4 and MEF2D proteins were used. Two separate DNA constructs were made with MEF2D fused with the GAL4 DNA binding domain (GAL4-MEF2D) and with the MEF2-binding motif of HDAC4 (AA 155-220) fused with the viral transactivator VP-16 (HDAC4-VP16). Human epithelial carcinoma cells (HeLa) were co-transfected with the two DNA constructs (GAL4-MEF2D and HDAC4-VP16) and a reporter plasmid (Gal4Luc). The DNA constructs resulted in expression of the GAL4-MEF2D and HDAC4-VP16 fusion proteins within the cell. MEF2D and HDAC4 protein interactions were detected as a result of the GAL4-MEF2D and HDAC4-VP16 protein complex binding a DNA promoter on the reporter plasmid (Gal4Luc) and driving cellular expression of a luciferase gene. The measured luciferase protein signal was proportional to the amount of MEF2D and HDAC4 protein interactions occurring with the cell.

Co-expression of GAL4-MEF2 and HDAC4-VP16 DNA constructs produced a luciferase response comparable to that generated by the positive control GAL4-VP16 fusion (GAL4VP16) in HeLa cells. The relatively stronger signal from the GAL4VP16 positive control construct was probably due to the fact that the activation domain of VP16 was covalently linked to GAL4, whereas in the mammalian two-hybrid assay it was recruited by protein-protein interactions between HDAC4 and MEF2. This assay permitted the detection of the interactions between HDAC4 and MEF2D with minimal interference from endogenous factors. The HDAC4 fragment lacked the catalytic domain so that the deacetylase activity was excluded from the assay.

Detection of inhibition of MEF2D and HDAC4 interactions. Next, the assay was used to test whether the compounds could disrupt the interactions between MEF2D and HDAC4. After co-expressing the GAL4-MEF2D and HDAC4-VP16 DNA constructs and reporter plasmid, the HeLa cells were treated with a test compound (10 µM) overnight. Cells transfected with the positive control GAL4VP16 fusion construct and reporter plasmid were also treated with the test compound (10 µM) overnight. As another control, DMSO was added (but kept below 0.2% V/V) to cells transfected with the positive GAL4VP16 fusion construct or the GAL4-MEF2D and HDAC4-VP16 DNA constructs. A luciferase assay was performed as described above according to the manufacturer's protocol (Promega). The luciferase response was normalized against the Renilla Luciferase as an internal control.

The relative activity and $IC_{50}$ calculations. The test compound, at a concentration of 10 µM, decreased the reporter signal driven by GAL4-MEF2D and HDAC4-VP16 protein complex by X fold, while the control solution, which was DMSO, also decreased the reporter signal by Y fold. The relative activity, I, was the ratio of former to later, i.e. X/Y, expressed in percentile. The relative activity for compounds showing the strongest inhibition was low compared with those compounds that showed little to no inhibition of MEF2D and HDAC4 interactions. The $IC_{50}$ was the concentration of the compounds when X/Y equals 50.

Results

Table 5 shows the $IC_{50}$ result for each compound tested. The lower the $IC_{50}$, the greater the inhibition of protein/protein interactions between MEF2 and the tested co-factor.

TABLE 6

Inhibition of MEF2D/HDAC4 protein-protein interactions

| No. | IC50 (µM) |
| --- | --- |
| ST1 | 9.4 |
| ST2 | 5.94 |
| ST3 | 4.87 |
| ST4 | 1.07 |
| ST5 | 191 |
| ST6 | 2.46 |
| ST7 | 1.6 |
| ST8 | 2.4 |
| ST9 | 3.53 |
| ST10 | 2.51 |
| ST11 | 18.0 |
| ST12 | 3.36 |
| ST13 | 1.52 |
| ST14 | 1.52 |
| ST15 | 0.92 |
| ST16 | 0.38 |
| ST17 | 0.99 |
| ST18 | 1.03 |
| ST19 | 0.32 |
| ST20 | 0.32 |
| ST21 | 0.35 |
| ST22 | 0.54 |
| ST23 | 0.42 |
| ST24 | 1.02 |
| ST25 | 0.95 |
| ST26 | 0.79 |
| ST27 | 0.35 |

TABLE 6-continued

Inhibition of MEF2D/HDAC4 protein-protein interactions

| No. | IC50 (μM) |
|---|---|
| ST28 | 0.67 |
| ST29 | 1.18 |
| ST30 | >20 |
| ST31 | 0.56 |
| ST32 | 0.25 |
| ST33 | 0.37 |
| ST34 | 2.03 |
| ST35 | 4.72 |
| ST36 | 1.88 |
| ST37 | 0.59 |
| ST38 | 0.26 |
| ST39 | 0.31 |
| ST40 | 0.26 |
| ST41 | 1.16 |
| ST42 | 0.07 |
| ST43 | 0.27 |
| ST44 | 0.38 |
| ST45 | 0.56 |
| ST46 | 0.67 |
| ST47 | 1.49 |
| ST48 | >20 |
| ST49 | 0.51 |
| ST50 | 2.55 |
| ST51 | >20 |
| ST52 | >20 |
| ST53 | 1.83 |
| ST54 | 7.27 |
| ST55 | 4.53 |
| ST56 | 5.22 |
| ST57 | >20 |
| ST58 | 3.01 |
| ST59 | 3.13 |
| ST60 | 5.04 |
| ST61 | 8.03 |
| ST62 | 3.04 |
| ST63 | 1.85 |
| ST64 | Not tested |
| ST65 | 5.37 |
| ST66 | 2.48 |
| ST67 | 3.06 |
| ST68 | 2.1 |
| ST69 | 0.98 |
| ST70 | 0.14 |
| ST71 | 0.27 |
| ST72 | 1.55 |
| ST73 | 1.15 |
| ST74 | 0.32 |
| ST75 | 0.41 |
| ST76 | >10 |
| ST77 | 0.64 |
| ST78 | >20 |
| ST79 | 0.28 |
| ST80 | 0.56 |
| ST81 | 0.85 |
| ST82 | 0.5 |
| ST83 | 0.84 |
| ST84 | 0.93 |
| ST85 | 0.47 |
| ST86 | >20 |
| ST87 | 3.06 |
| ST88 | 7.32 |
| ST89 | 0.77 |
| ST90 | 0.46 |
| ST91 | 1.46 |
| ST92 | 0.81 |
| ST93 | 0.61 |
| ST94 | 0.80 |
| ST95 | 1.04 |
| ST96 | 1.37 |
| ST97 | 0.45 |
| ST98 | 0.32 |
| ST99 | 0.59 |
| ST100 | 0.21 |
| ST101 | 0.35 |
| ST102 | 0.94 |
| ST103 | 0.35 |
| ST104 | 0.47 |
| ST105 | 1.48 |
| ST106 | 1.11 |
| ST107 | 0.44 |
| ST108 | 0.40 |
| ST109 | 0.68 |
| ST110 | 0.42 |
| ST111 | 0.94 |
| ST112 | 0.61 |
| ST113 | 0.26 |
| ST114 | 1.25 |
| ST115 | 0.54 |
| ST116 | 0.57 |
| ST117 | 0.94 |
| ST118 | 0.490 |
| ST119 | 0.390 |
| ST120 | 1.56 |
| ST121 | 2.75 |
| ST122 | 1.62 |
| ST123 | 2.0 |
| ST124 | 1.53 |
| ST125 | 2.44 |
| ST126 | 3.68 |
| ST127 | 1.84 |
| ST128 | 2.51 |
| ST129 | 20 |

Example 21

Mammalian Two-Hybrid Assay Used to Determine the Inhibitory Effects of the Compounds on MEF2D and P300 Protein Interactions Method Detection of MEF2D and P300 interactions. The same system that was used in Example 19 is used in here to detect MEF2D and P300 interactions. In this assay, two separate DNA constructs were made with MEF2D fused with the GAL4 DNA binding domain (GAL4-MEF2D) and P300 fused with the viral transactivator VP-16 (HDAC4-VP16). Human epithelial carcinoma cells (HeLa) were co-transfected with the two DNA constructs (GAL4-MEF2D and P300-VP16) and a reporter plasmid (Gal4Luc). The DNA constructs resulted in expression of the GAL4-MEF2D and P300-VP16 fusion proteins within the cell. MEF2D and P300 protein interactions were detected as a result of the GAL4-MEF2D and P300-VP16 protein complex binding a DNA promoter on the reporter plasmid (Gal4Luc) and driving cellular expression of a luciferase gene. The measured luciferase protein signal was proportional to the amount of MEF2D and P300 protein interactions occurring with the cell.

The relative activity and $IC_{50}$ calculations. The $IC_{50}$ concentrations were calculated in the same manner as described for Example 19. Results are shown below in Table 6.

Results

Table 6 shows the $IC_{50}$ results for each compound tested. The lower the $IC_{50}$, the greater the inhibition of protein/protein interactions between MEF2 and p300.

TABLE 7

Inhibition of MEF2D/p300 protein-protein interactions

| Compound No. | IC50 (μM) |
|---|---|
| ST49 | 0.27 |
| ST83 | 0.44 |
| ST119 | 0.14 |
| ST116 | 0.27 |
| ST85 | <0.15 |
| ST1 | 0.38 |
| ST53 | 3.6 |
| ST54 | 0.72 |
| ST55 | 0.51 |
| ST89 | 0.071 |
| ST104 | 0.38 |
| ST94 | 0.7 |
| ST92 | 0.47 |
| ST93 | 1.08 |
| ST4 | 1.1 |
| ST7 | 1.6 |
| ST66 | 1.69 |
| ST63 | 2.73 |
| ST102 | 1.2 |
| ST129 | 20 |
| ST13 | 0.79 |
| ST14 | 0.94 |

Example 22

Inhibition of Fetal Calf Serum Induced Cardiomyocyte Hypertrophy

Method

To evaluate the ability of the test compounds to inhibit cardio myocyte hypertrophy in vitro, serum-starved neonatal rat ventricular myocytes (NRVMs) were exposed to medium with 5% Fetal Calf Serum (FCS), a powerful activator of myoctye growth (hypertrophy) and treated with one of the compounds at doses ranging from 0.2-10 μM or with the vehicle (dimethyl sulfoxide (DMSO)). Control cells received fresh media without serum. The myocyte size was determined 48 hours after treatment. The results in Table 7 show the concentrations of the test compounds required to reduce the FCS-induced hypertrophy in the NRVMs by 50% ($IC_{50}$ μM).

Results

Table 7 shows the $IC_{50}$ results for each compound tested. The lower the $IC_{50}$, the greater the inhibition of hypertrophy induced by the FCS in NRVMs.

TABLE 8

Inhibition of Cardiomyocyte Hypertrophy in Vitro

| Compound NO. | IC50 (μM) |
|---|---|
| ST49 | 1.23 |
| ST83 | 3.85 |
| ST119 | 0.079 |
| ST116 | 4400 |
| ST1 | 0.81 |
| ST53 | 11.71 |
| ST54 | 1.16 |
| ST55 | 9.26 |
| ST104 | 2.89 |
| ST93 | 5500 |
| ST4 | 4.37 |
| ST7 | 0.46 |
| ST66 | 1420 |
| ST63 | 4.2 |
| ST102 | 0.71 |
| ST129 | no inhibition |
| ST13 | 0.12 |
| ST14 | 0.15 |

REFERENCES

The references, patents and published patent applications listed below, and all references cited in the specification above are hereby incorporated by reference in their entireties, as if fully set forth herein.

1. Physician's Desk Reference, 41st Ed., Publisher Edward R. Barnhart, N.J. (1987).
2. PCT/US93/0082948.
3. Remington: The Science and Practice of Pharmacy, 21st Edition, Univ. of Sciences in Philadelphia (USIP), Lippincott Williams & Wilkins, Philadelphia, Pa., 2005.
4. Wu, L., Smythe, A. M., Stinson, et. al. Multidrug-resistant Phenotype of Disease-oriented Panels of Human Tumor Cell Lines Used for Anticancer Drug Screening. (1992) Cancer Research 52: 3029-3034.
5. Han A, He J, Wu Y, Liu J O, Chen L. Mechanism of recruitment of class II histone deacetylases by myocyte enhancer factor-2. J. Mol. Biol. 2005; 345:91-102.
6. Han A, Pan F, Stroud J C, Youn H D, Liu J O, Chen L. Sequence-specific recruitment of transcriptional co-repressor Cabin1 by myocyte enhancer factor-2. Nature. 2003; 422:730-734.
7. Jayathilaka, et al., Nucleic Acids Res. 2012 July; 40(12): 5378-5388.
8. Potthoff, Mo., and Olson, E. N. Development. 2007 December; 134 (23): 4131-4140.

What is claimed is:

1. A compound of Structure I:

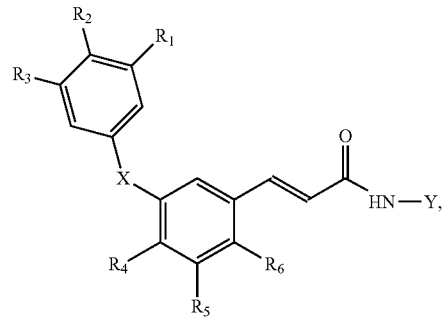

Structure I or a pharmaceutically acceptable solvate, pharmaceutically acceptable salt or pharmaceutically acceptable stereoisomer thereof, wherein:

Y is independently selected from the group consisting of 2-aminophenyl and hydroxyl;

X is independently selected from the group consisting of —NH—, —C(=O)NH—, —$(CH_2)_n$—NH—, —$(CH_2)_n$—NH—$(CH_2)_n$—, and —NH—$(CH_2)_n$—, wherein n is 1, 2, or 3;

$R_1$-$R_3$ are each independently selected from the group consisting of hydrogen, cyclopropyloxy, halogen, ethoxy, methoxy, methyl-mercaptan, ethoxy, ethyl, cyano, isopropyloxy, cyclobutyloxy, cyclopentyloxy, 3-oxetanyloxy, morpholinyl, 4-morpholinyl, dimethylamino, butyl, pyrrolidinyl, ethylmethylamino, piperidinyl, piperazinyl, diethylamino, dimethylaminomethyl, 3-oxetanyl, 2,2-difluoroethoxy, 1,1-difluoroethyl, methylsulfide, trifluoromethylsulfide, 2,2,2-trifluoroethoxy, and trifluoroethoxy, wherein at least one or two of $R_1$-$R_3$ are not hydrogen; and $R_4$-$R_6$ are each independently selected from the group consisting of hydrogen and halogen, wherein $R_4$ and $R_5$ are hydrogen and $R_6$ is a halogen.

2. The compound of claim 1, wherein the compound is

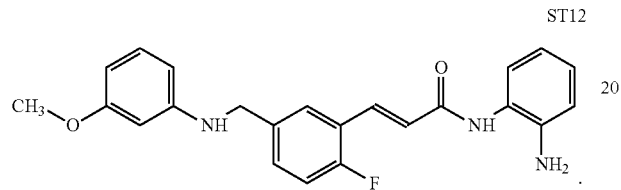

ST12

3. A compound of Structure I:

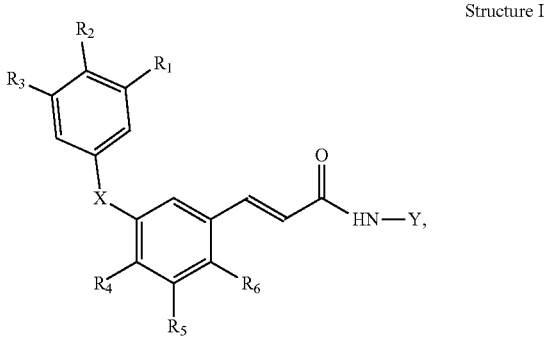

Structure I or a pharmaceutically acceptable solvate, pharmaceutically acceptable salt or pharmaceutically acceptable stereoisomer thereof, wherein:

Y is independently selected from the group consisting of 2-aminophenyl and hydroxyl;

X is independently selected from the group consisting of —NH—, —C(=O)NH—, —(CH$_2$)$_n$—NH—, —(CH$_2$)$_n$—NH—(CH$_2$)$_n$—, and —NH—(CH$_2$)$_n$—, wherein n is 1, 2, or 3;

$R_1$-$R_3$ are each independently selected from the group consisting of hydrogen, cyclopropyloxy, halogen, ethoxy, methoxy, methyl-mercaptan, ethoxy, ethyl, cyano, isopropyloxy, cyclobutyloxy, cyclopentyloxy, 3-oxetanyloxy, morpholinyl, 4-morpholinyl, dimethylamino, butyl, pyrrolidinyl, ethylmethylamino, piperidinyl, piperazinyl, diethylamino, dimethylaminomethyl, 3-oxetanyl, 2,2-difluoroethoxy, 1,1-difluoroethyl, methylsulfide, trifluoromethylsulfide, 2,2,2-trifluoroethoxy, and trifluoroethoxy, wherein at least one or two of $R_1$-$R_3$ are not hydrogen; and $R_4$-$R_6$ are each independently selected from the group consisting of hydrogen and halogen, wherein $R_4$ and $R_6$ are hydrogen and $R_5$ is a halogen.

4. The compound of claim 3, wherein the compound is

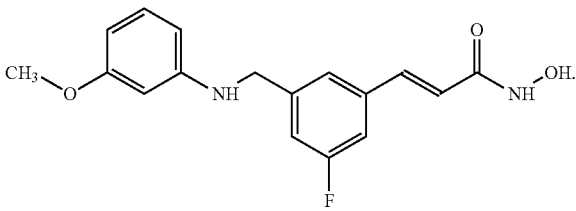

ST44

5. A compound of Structure I:

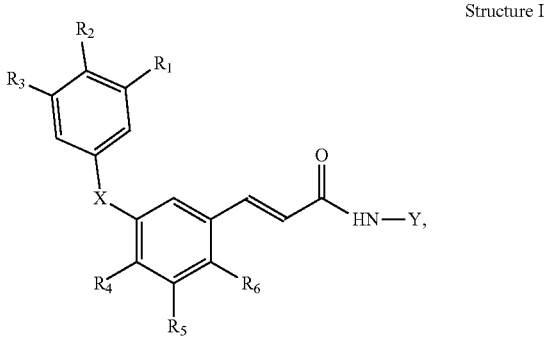

Structure I or a pharmaceutically acceptable solvate, pharmaceutically acceptable salt or pharmaceutically acceptable stereoisomer thereof, wherein:

Y is independently selected from the group consisting of 2-aminophenyl and hydroxyl;

X is independently selected from the group consisting of —NH—, —C(=O)NH—, —(CH$_2$)$_n$—NH—, —(CH$_2$)$_n$—NH—(CH$_2$)$_n$—, and —NH—(CH$_2$)$_n$—, wherein n is 1, 2, or 3;

$R_1$-$R_3$ are each independently selected from the group consisting of hydrogen, cyclopropyloxy, halogen, ethoxy, methoxy, methyl-mercaptan, ethoxy, ethyl, cyano, isopropyloxy, cyclobutyloxy, cyclopentyloxy, 3-oxetanyloxy, morpholinyl, 4-morpholinyl, dimethylamino, butyl, pyrrolidinyl, ethylmethylamino, piperidinyl, piperazinyl, diethylamino, dimethylaminomethyl, 3-oxetanyl, 2,2-difluoroethoxy, 1,1-difluoroethyl, methylsulfide, trifluoromethylsulfide, 2,2,2-trifluoroethoxy, and trifluoroethoxy, wherein at least one or two of $R_1$-$R_3$ are not hydrogen; and $R_4$-$R_6$ are each independently selected from the group consisting of hydrogen and halogen, wherein $R_5$ and $R_6$ are hydrogen and $R_4$ is a halogen.

6. The compound of claim 5, wherein the compound is

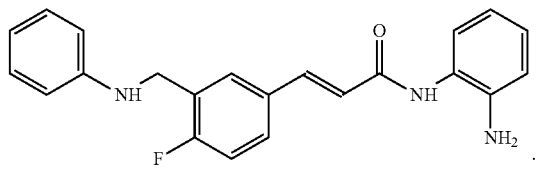

ST11

* * * * *